United States Patent
Corr et al.

(10) Patent No.: US 11,957,619 B2
(45) Date of Patent: Apr. 16, 2024

(54) HYPERTHERMIC VESSEL TREATMENT DEVICES AND METHODS AND KITS UTILIZING THE SAME

(71) Applicant: Baylor College of Medicine, Houston, TX (US)

(72) Inventors: Stuart James Corr, Houston, TX (US); Matthew James Ware, Houston, TX (US); Steven A. Curley, Missouri City, TX (US); Lam Nguyen, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 1440 days.

(21) Appl. No.: 16/301,042

(22) PCT Filed: May 12, 2017

(86) PCT No.: PCT/US2017/032521
§ 371 (c)(1),
(2) Date: Nov. 13, 2018

(87) PCT Pub. No.: WO2017/197339
PCT Pub. Date: Nov. 16, 2017

(65) Prior Publication Data
US 2019/0175397 A1 Jun. 13, 2019

Related U.S. Application Data

(60) Provisional application No. 62/335,759, filed on May 13, 2016.

(51) Int. Cl.
*A61F 7/12* (2006.01)
*A61B 18/04* (2006.01)
(Continued)

(52) U.S. Cl.
CPC ................ *A61F 7/12* (2013.01); *A61B 18/04* (2013.01); *A61B 18/08* (2013.01); *A61B 18/14* (2013.01);
(Continued)

(58) Field of Classification Search
CPC .......... A61B 18/08; A61B 18/14; A61B 5/01; A61B 5/425; A61F 2007/0071;
(Continued)

(56) References Cited

U.S. PATENT DOCUMENTS 5,336,221 A * 8/1994 Anderson .............. A61B 18/22
606/205
6,106,477 A 8/2000 Miesel et al.
(Continued)

*Primary Examiner* — Tigist S Demie
(74) *Attorney, Agent, or Firm* — Norton Rose Fulbright US LLP

(57) ABSTRACT

The present disclosure concerns hyperthermic devices for treating vascular involvements related to cancer therapies, such as surgery. In specific embodiments, the device is configured to provide therapeutic heating to destroy vessel-encasing tumors while still protecting the vessel itself. In particular embodiments, the devices utilize two opposing semi-cylindrical shells that encase the vessel in need of treatment of a tumor thereon. In other devices, a flexible substrate is guided under and around the vessel and tumor thereon.

14 Claims, 25 Drawing Sheets

(51) Int. Cl.
*A61B 18/08* (2006.01)
*A61B 18/14* (2006.01)
*A61F 7/00* (2006.01)
*A61N 1/40* (2006.01)
*A61N 5/06* (2006.01)
*A61B 5/00* (2006.01)
*A61B 5/01* (2006.01)
*A61N 5/00* (2006.01)

(52) U.S. Cl.
CPC .............. *A61F 7/007* (2013.01); *A61N 1/403* (2013.01); *A61N 5/0601* (2013.01); *A61N 5/0625* (2013.01); *A61B 5/01* (2013.01); *A61B 5/425* (2013.01); *A61F 2007/0071* (2013.01); *A61F 2007/0094* (2013.01); *A61F 2007/0096* (2013.01); *A61N 2005/007* (2013.01); *A61N 2005/0651* (2013.01)

(58) Field of Classification Search
CPC ...... A61F 2007/0094; A61F 2007/0096; A61F 7/007; A61F 7/12; A61N 1/403; A61N 2005/007; A61N 2005/0651; A61N 5/0601; A61N 5/0625
See application file for complete search history.

(56) References Cited

U.S. PATENT DOCUMENTS

| | | | |
|---|---|---|---|
| 6,159,207 A * | 12/2000 | Yoon | A61B 90/04 606/41 |
| 9,192,715 B2 | 11/2015 | Gelfand et al. | |
| 2002/0111386 A1* | 8/2002 | Sekins | A61M 16/0459 607/104 |
| 2002/0120261 A1* | 8/2002 | Morris | A61M 25/1002 606/41 |
| 2008/0262341 A1* | 10/2008 | Boyden | G16H 40/67 604/20 |
| 2010/0069904 A1* | 3/2010 | Cunningham | A61B 18/14 606/48 |
| 2010/0168567 A1 | 7/2010 | Kochavi et al. | |
| 2013/0324986 A1 | 12/2013 | Ott et al. | |

* cited by examiner

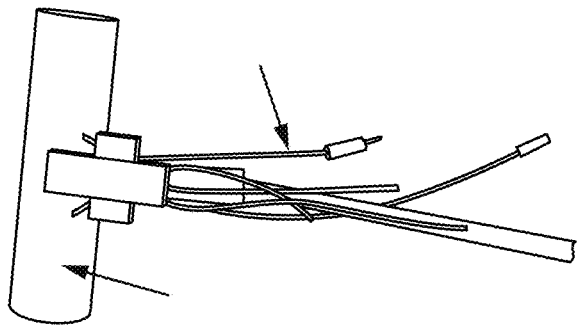
FIG. 2B1
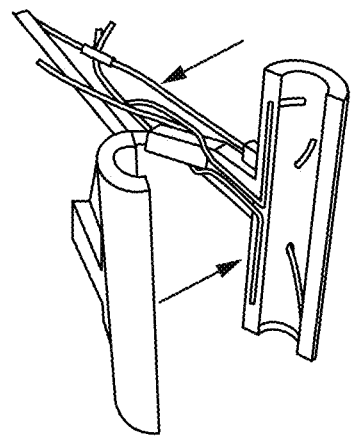
FIG. 2B3
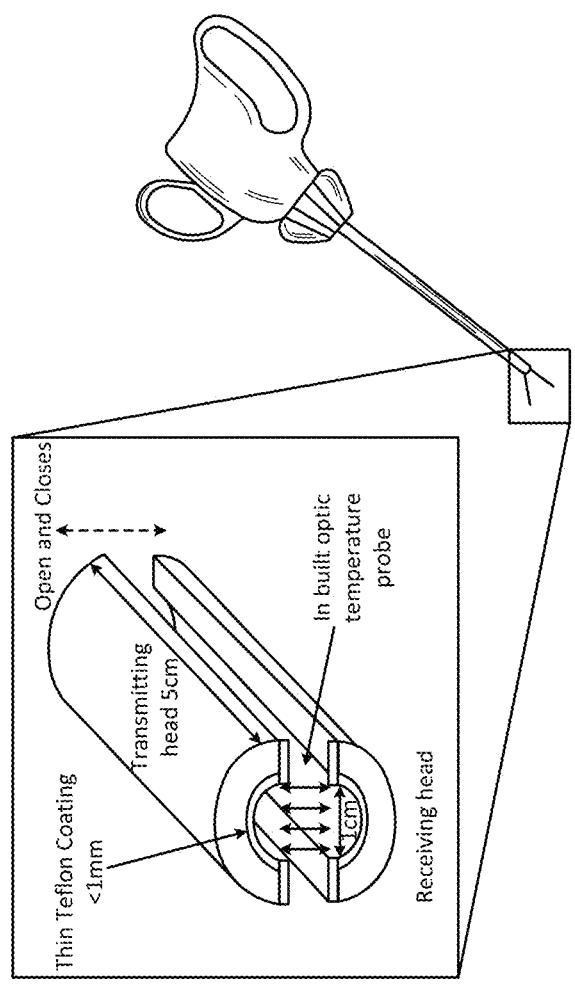
FIG. 2A
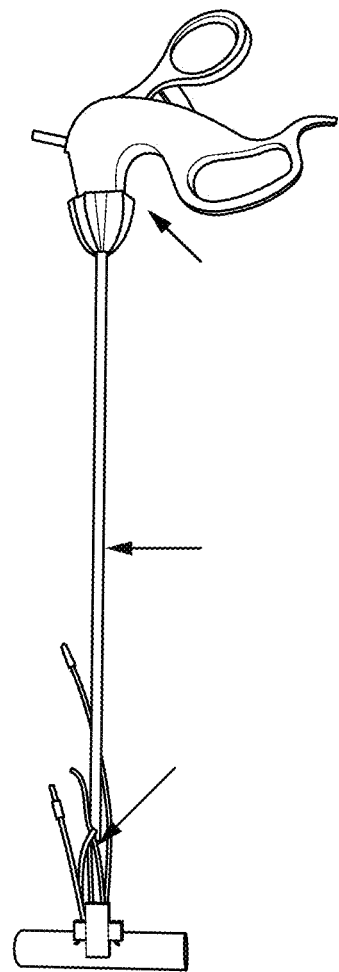
FIG. 2B2

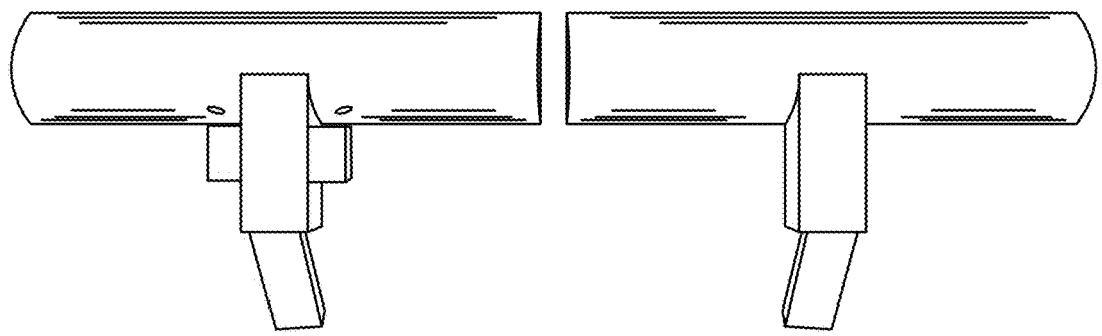
FIG. 2E1
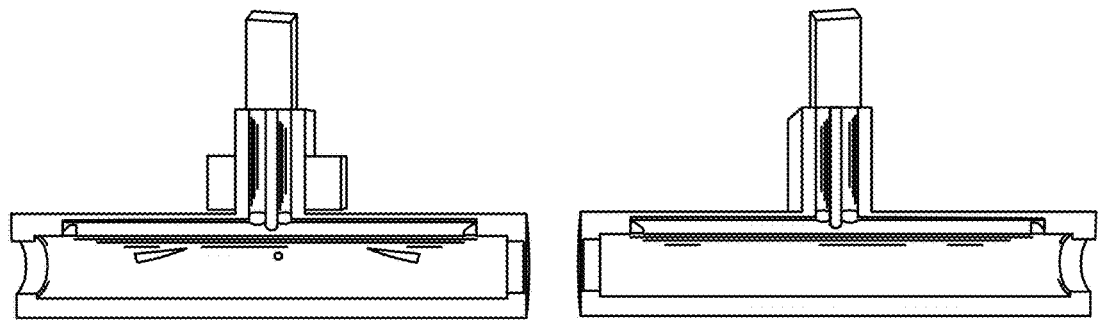
FIG. 2E2
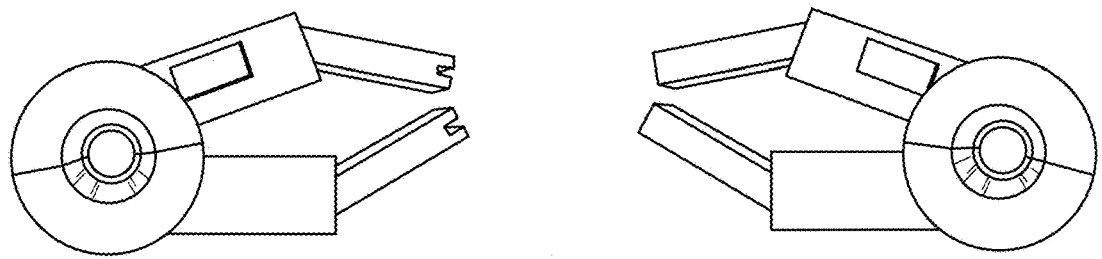
FIG. 2E3
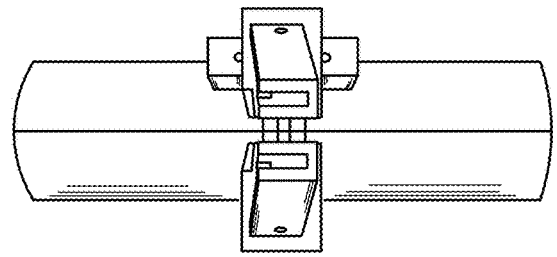
FIG. 2E4
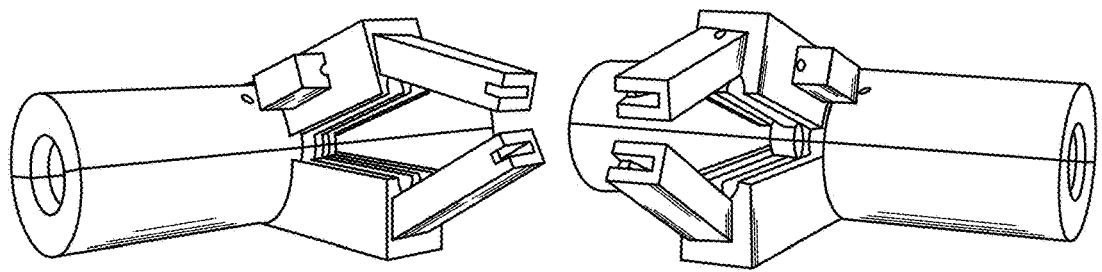
FIG. 2E5

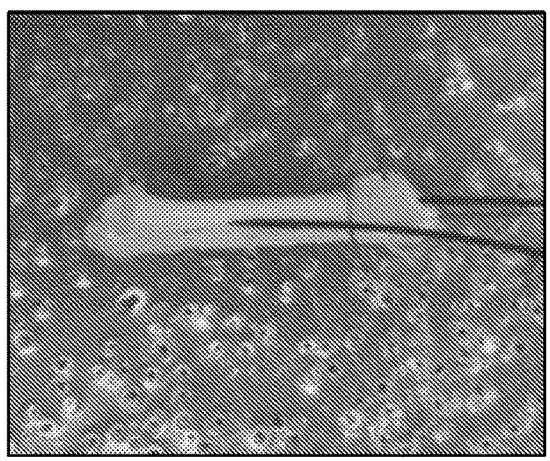
FIG. 5C (top right)
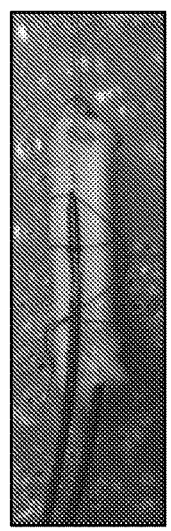
FIG. 5E
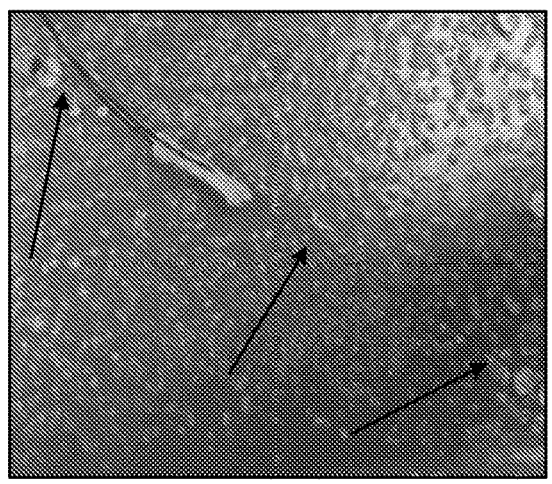
FIG. 5B
FIG. 5D
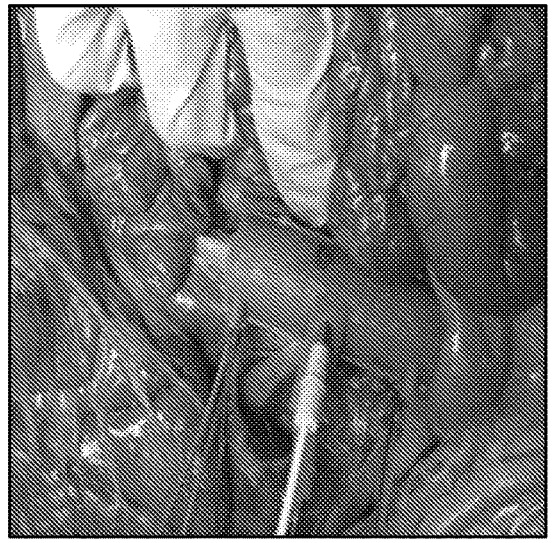
FIG. 5A
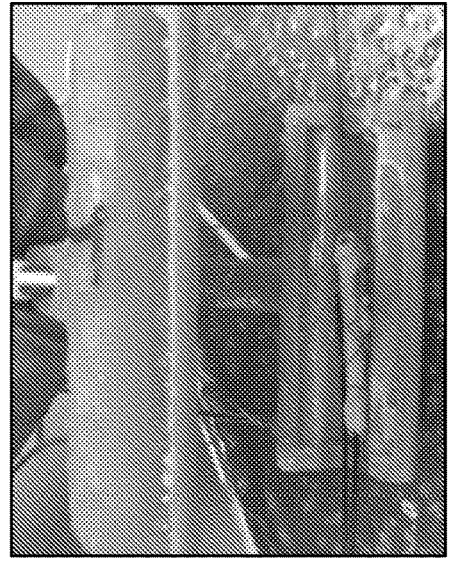
FIG. 5C (bottom left)

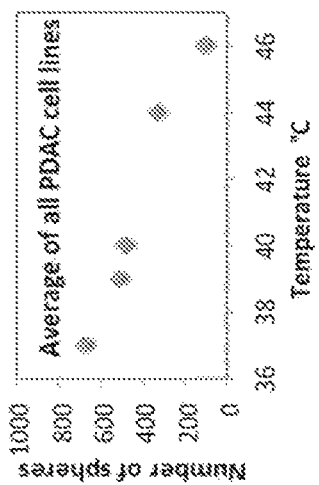
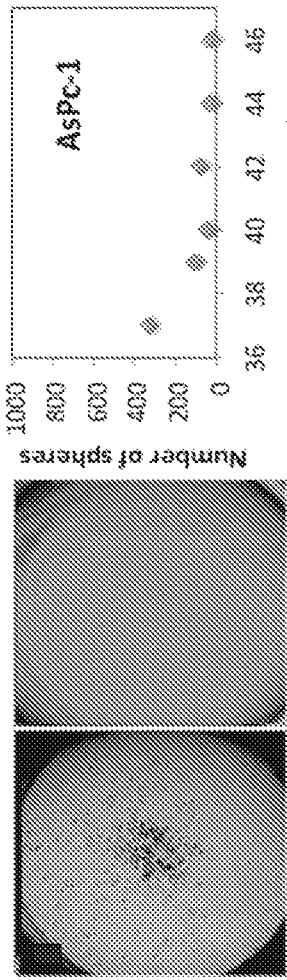
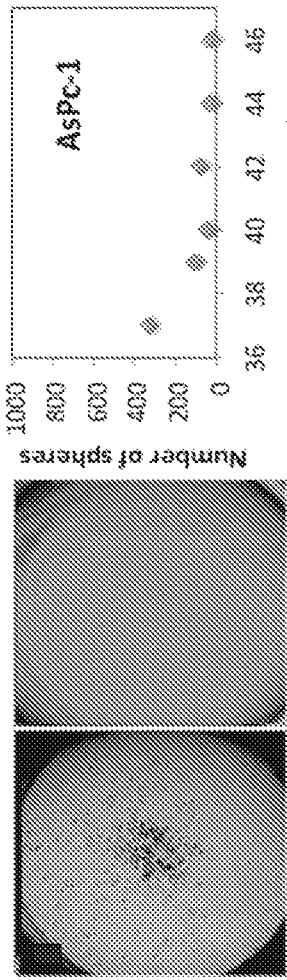
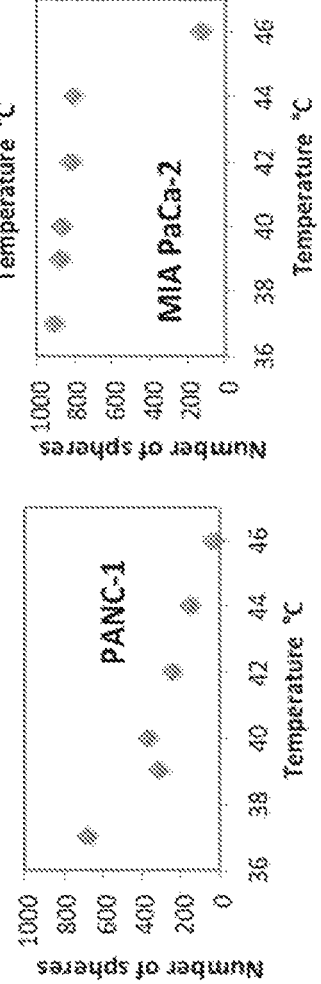
FIG. 11A  FIG. 11B  FIG. 11C  FIG. 11D  FIG. 11E

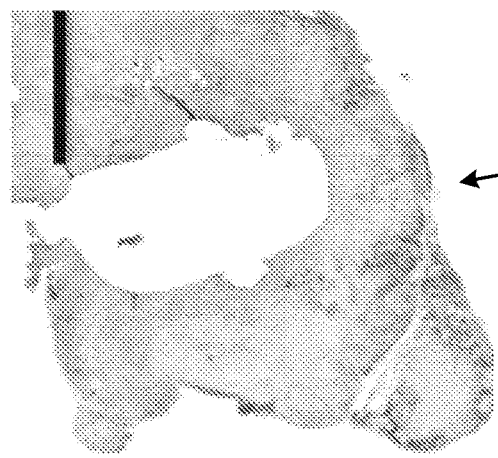
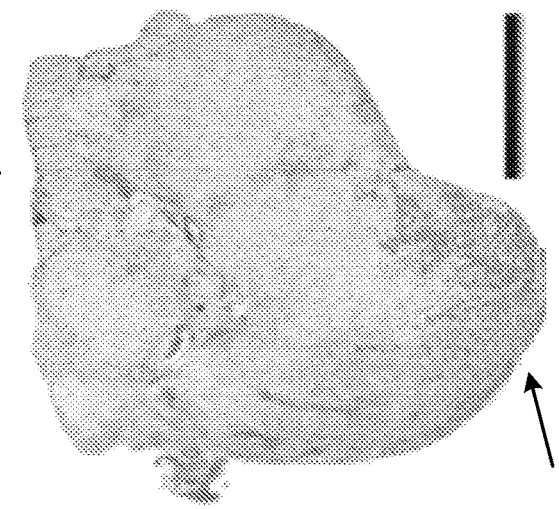
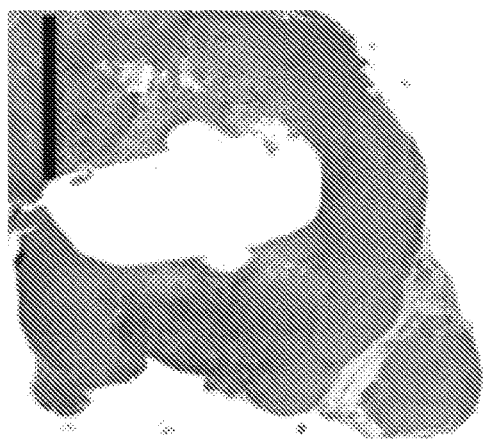
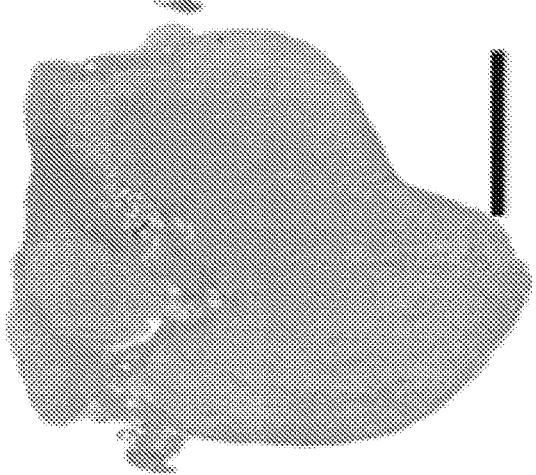
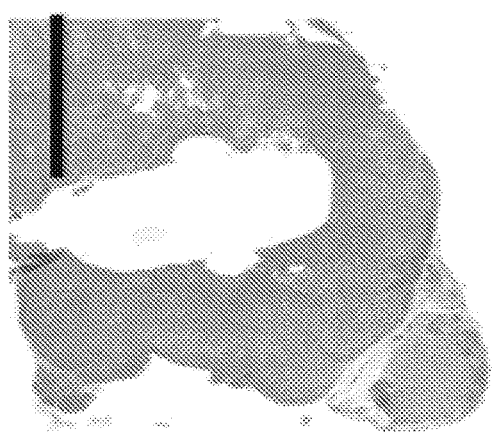
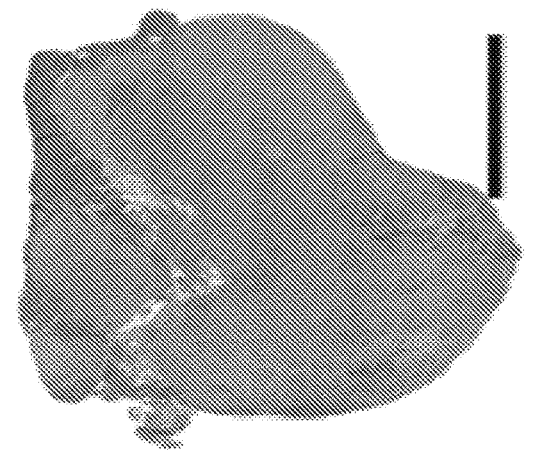
FIG. 12F
FIG. 12G

HYPERTHERMIC VESSEL TREATMENT DEVICES AND METHODS AND KITS UTILIZING THE SAME

The present application is a national phase application under 35 U.S.C. § 371 that claims priority to International Application No. PCT/US2017/032521 filed May 12, 2017, which claims priority to U.S. Provisional Patent Application Ser. No. 62/335,759, filed May 13, 2016, all of which are incorporated herein by reference in their entirety.

TECHNICAL FIELD

Embodiments of the disclosure include at least the fields of devices and cancer treatment.

BACKGROUND

The incidence of pancreatic ductal adenocarcinoma (PDAC) has gradually been increasing. Cancer of the pancreas is the sixth most common cancer and fourth most common cause of death from cancer. PDAC is associated with a poor prognosis, with a 5-year survival of around 6%. Surgical resection remains the only chance for curative therapy in patients with localized PDAC. Only 16% of patients initially present with disease confined to the pancreas (stage I). There is a subset of patients who are assessed to have locally advanced, unresectable disease because of abutment or encasement of the superior mesenteric artery (SMA). Patients who present with metastatic disease (Stage III or IV) are precluded from attempted resection with curative intent because of the aggressive nature and poor prognosis of metastatic PDAC.

In the absence of metastatic disease that precludes resection, vascular invasion is the main factor that deems PDAC unresectable. Various imaging modalities, i.e., computed tomography (CT) or magnetic resonance (MR), are used for the initial assessment of tumor location, as depicted in FIG. 1. Vascular invasion is a relatively frequent discovery in PDAC and is found in 21%-64% of patients. The invasion of the superior mesenteric vein or portal vein is not in itself a criterion of unresectability. However, contrary to venous involvement, a tumor infiltration of a large arterial trunk (i.e., celiac axis, superior mesenteric artery, or hepatic artery) currently constitutes a contraindication to surgery. Arterial resection and reconstruction is associated with high morbidity and mortality. Because of the risk of arterial injury or thrombosis, grossly positive margins are frequently present after surgical resection of such tumors, resulting in high tumor recurrence and poor patient survival benefit.

The present disclosure satisfies a long-felt need in the art to provide methods and multiple embodiments of compositions for treatment of any cancers or other diseases otherwise precluded from treatment because of the location of the tissue or region in need of treatment, such as tumors that are on, surround, or are adjacent to a vessel.

BRIEF SUMMARY

Embodiments of the disclosure encompass methods and devices for treating tumors. One embodiment of the disclosure utilizes devices that are able to be used when space is anatomically suitably available to maneuver the device around and near a vessel having a tumor. Other embodiments of the disclosure utilizes devices that are able to be used when space is anatomically limiting, such that the device will need to be able to be maneuvered in a compact setting. Embodiments of a variety of types and sizes of devices may or may not be able to be utilized in positive margins with various anatomical shapes and settings.

In one embodiment, there is a medical device comprising a first semi-cylindrical shell and a second semi-cylindrical shell, together defining an inner lumen adapted and configured to receive an anatomical vessel; one or more energy sources; and a controller programmed to control operation of the one or more energy sources to heat at least a portion of the anatomical vessel or a tumor adjacent thereto to a hyperthermic temperature sufficient to diminish or prevent future tumor growth. In specific cases, the medical device further comprises one or more diffusers located diametrically inward from the one or more heating elements. One or more diffusers may comprise gelatin, in certain cases. In specific embodiments, the device further comprises one or more temperature sensors located on an inner surface of the one or more diffusers and communicatively coupled to the controller. In specific embodiments, the one or more energy sources are resistive heating elements. The controller may be programmed to control operation of the one or more energy sources to heat at least a portion of the anatomical vessel or the tumor adjacent thereto to between about 37° C. and about 46° C. In specific embodiments, the controller is programmed to control operation of the one or more energy sources to heat at least a portion of the anatomical vessel or the tumor adjacent thereto to between about 44° C. and about 46° C. The controller may be programmed to control operation of the one or more energy sources to heat at least a portion of the anatomical vessel or the tumor adjacent thereto to about 46° C. In at least some cases, the device is about 3 cm to about 6 cm longitudinally in length.

In one embodiment, there is a medical device comprising a first semi-cylindrical shell and a second semi-cylindrical shell together; one or more energy sources mounted on one or more inner surfaces of the first semi-cylindrical shell and on one or more inner surfaces of the second semi-cylindrical shell; one or more diffusers located diametrically inward from the one or more energy sources; one or more temperature sensors located on an inner surface of the one or more diffusers; and a controller communicatively coupled to the one or more temperature sensors, the controller programmed to control operation of the one or more energy sources based on feedback from the one or more temperature sensors to heat at least a portion of the anatomical vessel or a tumor adjacent thereto to a hyperthermic temperature sufficient to diminish or prevent future tumor growth. In some cases, a surface of the device comprises one or more anti-cancer therapies, such as a chemotherapeutic drug, a hormone therapy, an immunotherapy, or a combination thereof.

In a particular embodiment, there is disclosed a method of treating an anatomical vessel, the method comprising positioning any medical device of the disclosure around the anatomical vessel and/or any unresected tumor adjacent thereto; and actuating the medical device to heat at least a portion of an anatomical vessel or any unresected tumor adjacent thereto to a hyperthermic temperature sufficient to diminish or prevent future tumor growth. The anatomical vessel may be a blood vessel, such as of the celiac axis, superior mesenteric artery, and/or hepatic artery. In specific embodiments, the tumor is a pancreatic ductal adenocarcinoma (PDAC).

In some cases, at least a portion of the vessel is heated for a range of time from 0.5-30 minutes. In particular embodiments, a hyperthermic temperature is between 37-46° C. In specific cases, one or more cooling agents are provided to the vessel upstream of the device, such as a cooling pack.

In one embodiment, there is a medical device, comprising a substrate comprising a heating area and at least one temperature sensor, wherein the heating area and the at least one temperature sensor are on or within a flexible material. In particular cases, the device is configured to be positioned transversal to the length of a vessel. The device may be configured to be positioned generally perpendicular to the length of a vessel. The temperature sensor may be configured to measure the temperature of a tumor upon or around which the device is placed. An example of a flexible material is a polymer, such as a silicone. In specific cases, the device further comprises at least one guiding mechanism, such as a wire, including the guiding mechanism being placed at one end of the device. In specific embodiments, the device comprises a first outer surface and a second outer surface that opposes the first outer surface, wherein the heating area and the at least one temperature sensor are positioned closer to the first outer surface of the device than to the second outer surface of the device.

In a certain embodiment, there is disclosed a method of treating an anatomical vessel, the method comprising positioning the medical device of any one of claims 22-31 around the anatomical vessel and/or any tumor tissue thereon; actuating the medical device to heat at least a portion of the anatomical vessel or the tumor tissue to a hyperthermic temperature sufficient to diminish or prevent future tumor growth. In specific cases, the positioning comprises inserting the device transversally under the vessel and holding or clamping the ends of the device together such that the device generally encircles the vessel at the site of the tumor. The positioning step may utilize a guiding mechanism at one end of the device. In particular embodiments, there is a range of sizes of the device. In some cases, a particular size of the device is selected prior to or after obtaining direct access to the tumor and/or directly visualizing the tumor. A particular size of the device may be selected using direct or indirect imaging. The imaging may comprise magnetic resonance imaging, CT scan, or both.

In some embodiments, there is a kit for treating an anatomical vessel, the kit comprising any medical device encompassed herein; and optionally, instructions for use thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIGS. 2A-2E5 depict further embodiments of one design of a hyperthermic vessel treatment device. FIG. 2A depicts a schematic design. FIGS. 2B1-2B3 provide images of a prototype. Red arrows denotes the electrical wires to power the heating element encased within a cylindrical head. White arrows denote the interior temperature probe wiring. Black arrows denotes the neck of the device, which can be clamped in position by the surgeon on a stand and holds all of the wiring away from the patient. The yellow arrow denotes the handle of the device, which can be used to position the device on the artery and to open, close, and/or lock the cylindrical head on the artery. FIGS. 2E1-2E4 and 2E5 provide computer renderings of a head of a hyperthermic vessel treatment device. Sizes and dimensions of any device design embodiment can be adjusted according to patient and tumor section size.

FIG. 3A) Heating curves FIG. 3B) Morphological changes in HUVEC cells 24 h after hyperthermia (44° C. for 10 min) are not observed via SEM. FIG. 3C) Percentage cell death of various cell lines of the pancreatic cancer microenvironment at 0 h after heat treatment at various temperatures FIG. 3D) % cell death of various cell lines of the PDAC microenvironment 24 h after heat treatment at various temperatures FIG. 3E) Viability of PANC-1 cells 48 h after gemcitabine exposure and hyperthermia pre-treatment, cancer cells are more susceptible to gemcitabine after heat pre-treatment. FIG. 3F) Migratory behavior of cancer cells after hyperthermia treatment as determined using the Boyden chamber assay (error bars represent standard deviation, experiment performed in triplicate). After hyperthermia there are cells which stay adhered to the substrate and there are cells which detach and are floating in the cell culture media, therefore this figure depicts both populations of cells after hyperthermia FIG. 4A depicts combined temperatures showing controllable and consistent heating across length of device (inset, image of black optical temperature probes placed either side of device in contact with gelatin bag to obtain measurements described in FIGS. 4A and 4B). FIG. 4B depicts temperature (40° C., 42° C., 44° C., 46° C., 48° C., and 50° C.) versus current (red and blue curve represent probes 1 and 2 respectively and black curve represents current passed through heating element in gelatin bag).

FIGS. 5A-5E depict ex vivo testing of some devices according to embodiments of the invention in swine. FIG. 5A depicts testing for its ability to fit around the aorta in an ex vivo swine model. FIG. 5B depicts an artery pulled taught using sutures and pins (white arrows) to simulate its position in vivo. FIG. 5C (top right) depicts an optical probe tethered to the outside surface of the aorta and another optical probe inserted into the lumen of the aorta. FIG. 5C (bottom left)

depicts positioning of the artery inside the device in readiness for heat treatment. FIG. 5D depicts closure of the device while current is passed through the device for heating. Heating can be controlled by adjusting the current passing into the device. FIG. 5E depicts an image of the artery after treatment. The artery was dehydrated after treatment. This was due its extracorporeal nature and exposure to higher temperatures for longer durations than needed for proof of principle exploration. This ex vivo set up explored the heat differential between the inside and outside of the artery without blood flow.

FIG. 6A depict the heating rate of the gelatin chamber inside the device (black curve), heating differential between the outside aorta surface (dark red curve), and inside the aorta lumen (blue curve). The bright red curve shows current adjustment throughout treatment to heat to 50° C. between 0-1000 seconds and then to produce constant 50° C. temperature between 1000-2650 seconds, before turning off the device. FIG. 6B depicts the difference in temperature between the outside and inside of the device during the heat treatment.

In FIG. 7A, the SMA is exposed in readiness for the device to be fitted. In FIG. 7B, an optical probe is placed inside the lumen of the SMA and the second probe is tethered to the surface of the SMA via surgical stitch. In FIG. 7C, the device is fitted around the SMA with probes positioned. In FIG. 7D, the device is closed and current is passed through the device for heating to occur. Heating can be controlled by adjusting the current passing into the device. FIG. 7E depicts the SMA after treatment (box) indicating the portion of SMA that was inside the device.

In FIGS. 9A and 9B, the femoral artery of a swine is exposed in readiness for the device to be fitted. In FIG. 9C, an optical probe is placed inside the lumen of the femoral artery and the second probe is tethered to the surface of the artery via a loose surgical stitch to prevent as much alteration to blood flow as possible. In FIG. 9D, the device is fitted around the femoral artery with probes positioned. The device is closed and current is passed through the device to produce controlled heating.

In FIG. 10A, the device (6 cm length version) is placed around the femoral artery. Black optical probes have been positioned inside the lumen of the artery and on the outside of the artery. The red arrow indicates direction of blood flow. FIG. 10B depicts the heating differential between the outside femoral artery surface (blue curve) and inside the FA lumen (red curve). The black solid line placed at 1300 seconds after initiation of heating indicates when occlusion of the artery was halted. Previous to this time point there was no blood running through the artery and hence a small differential in the temperatures between the outside and inside of the artery. Two black dashed lines indicate times when the device was adjusted when placed on the artery. A constant 46° C. thermal dose was achieved between 380-840 seconds, before turning the device off (far right yellow dashed line).

FIGS. 11A-11E depict that heat destroys pancreatic stem cells and which are important cancer cells thought to play a major role in tumor cannot renew. FIG. 11A) Brightfield image of PANC-1 cancer cells before treatment (left) and with heat treatment (46° C. for 10 minutes) (right) FIGS. 11B-11E) the number of viable pancreatic cancer stem cell spheres formed at 14 days after water bath heat treatment of various temperatures (37° C., 39° C., 40° C., 42° C., 44° C. and 46° C. for 10 minutes).

FIGS. 12A-12G depict tumor heat differential and cell death in in vivo murine pancreatic cancer model. FIG. 12A) PDAC tumor is exposed in a live mouse and positioned for heat treatment. A body temperature probe is inserted rectally and a copper blanket prevents unwanted areas of the mouse body being heated. FIG. 12B) The heating device is placed onto the tumor FIG. 12C) The heat differential between tumor boundary and tumor core (mouse body core temperature is also displayed) FIGS. 12D) and 12E) tumor after treatment (yellow scale bar=2 cm, and yellow arrow represents heated side of tumor) FIGS. 12F) and 12G) Row of histological cross-sectional micrographs of tumors treated with hyperthermia (from left to right, H&E, picro Sirius and Cl-PARP histology stains, red arrows indicate heated surface, black scale bars=2 mm, one tumor per row).

FIG. 13A) Device placement around femoral artery with insertion of a fiber optic temperature probe inside artery and another probe on the artery surface (probe inserted in direction of blood flow to minimize disruption in blood flow inside artery, red arrow). FIG. 13B) Femoral artery after hyperthermia treatment (yellow arrows indicate areas where cauterization was performed to skeletonize branches from main vessel) FIG. 13C) Heating differential between the outside femoral artery surface (black curve) and inside the femoral artery lumen (grey curve). (Red arrow indicates time-point when hyperthermia was halted) (FIG. 13D) Simulation of tissue heating using an embodiment of the device on a 1 mm positive cancer margin and (FIG. 13E) simulation of tissue heating using an embodiment of the device on a 10 mm positive cancer margin. The solid horizontal line indicates 46° C., the desired tissue temperature. The vertical dotted lines are the innermost edge of the blood vessel wall, the vertical dashed line is the outermost edge of the tissue and the vertical dash-dot line is the interface between the blood vessel and the tissue. Tumor tissue thicknesses are: FIG. 13D) 1 mm, FIG. 13E) 10 mm.

(FIG. 14A) Untreated femoral artery (FIG. 14B) femoral artery exposed to 46° C. for 10 mins and (FIG. 14C) femoral artery exposed to 55° C. for 10 mins (positive control). FIG. 14H) Adipose tissue surrounding the treated portion of a SMA artery in a swine 48 hours after heat treatment (FIG. 14G) Muscle wall and endothelial layer of the treated portion of the artery in a swine 48 hours after heat treatment. (FIG. 14H) Small intestine (right hand images are zoomed in images) in a swine 48 hours after heat treatment.

FIGS. 15A-15D show staging of patients in resectable, borderline resectable and unresectable pancreatic cohorts and schematic of artery-tumor system. FIG. 15A) CT scan of resectable pancreatic (large arrows); patient had no distant metastases, a clear fat plane is visible around the celiac, hepatic and mesenteric arteries (light blue arrows) and there is no abutment of superior mesenteric vein or portal vein. FIG. 15B) CT scan of borderline resectable PDAC; there is some tumor-SMA interaction (dark blue arrows) but <180 degrees. FIG. 15C) CT scan of unresectable PDAC; patient's tumor has totally encasing the SMA (>180 degrees) (Primary tumor mass indicated by large green arrows). FIG. 15D) Schematic overview of one device of the disclosure including artery, tumor and device. Surgeons can typically remove tumor but have to leave 1-3 mm of positive margin, in at least some cases. Device heats outside of the SMA, which is the main tumor layer with endothelial tissue and smooth muscle lying underneath.

FIG. 16A) Hierarchical clustering of RPPA data of untreated cells versus treated cells 24 h after treatment (differentially expressed proteins, t test P value <0.05 and fold change>than 1.25 for up-regulation or <0.8 for down-regulation). FIG. 16B) Activated or suppressed canonical pathways due to heat treatment data are displayed as the Z-score value for each pathway. See Table 1.

FIGS. 17A-17B) Tumor, device and probe orientation FIG. 17C) Schematic describing tumor, device and probe orientation during testing (one probe is placed on tumor-device boundary and another probes is inserted into tumor at a 2 mm distance from Probe on the outside surface) FIGS. 17D, 17E, 18F) Heating differential between the tumor boundary in contact with the device (black curve) and 2 mm inside the PDAC tumor (grey curve) for as a model for positive margin left after surgical resection, with tumor core heated to 42° C., 44° C. and 46° C., respectively. Red arrow represents time point when the device is turned off and cooling of tumor boundary and inside tumor occurs.

FIGS. 19A and 19B show images of a device used for tight anatomical spaces along with an IR camera image of the heating surface (FIG. 19C). While FIGS. 19D-19F show computer generated schematic of the device for use in less tight anatomical positions and FIG. 19G shows a prototype of a device (red arrow indicates total length, in this case it is approximately 3.5 cm and the orange arrow represents the heating zone that is 3 cm in width. The flexible heating element curves completely around the cancer-encased artery. The insulated back of the device keeps heat from non-target tissues.

DEFINITIONS

Figure 1:
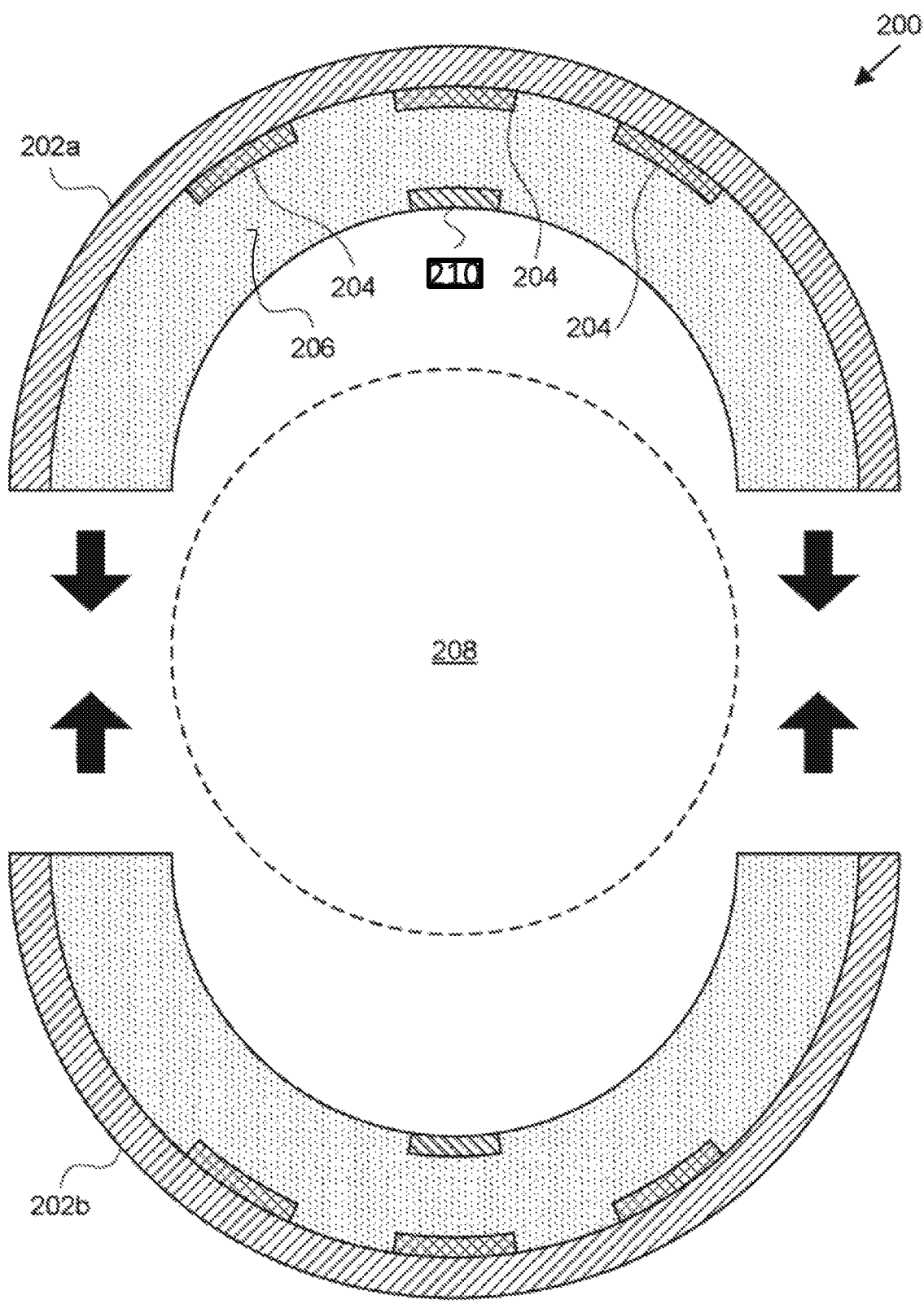
FIG. 1 depicts a cross-section of a hyperthermic vessel treatment device according to an embodiment of the disclosure.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein. As used in the specification and claims, the terms "comprises," "comprising," "containing," "having," and the like can have the meaning ascribed to them in U.S. patent law and can mean "includes," "including," and the like.

The term "cylinder" not only includes three-dimensional shapes having a circular cross-section, but also any surface consisting of each of the straight lines that are parallel to a given straight line and pass through a given curve.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

A "subject" shall be understood to include any mammal including, but not limited to, humans. The term "subject" can include all subsets of individuals within a particular class of subjects, e.g., males, females, infants, children, adolescents, adults, male adolescents, female adolescents, male adults, female adults, and the like.

DETAILED DESCRIPTION

Embodiments of the disclosure provide devices that can be used intra-operatively to treat patients who have tumors, including that would be currently deemed "borderline unresectable" or "unresectable", thus hopefully moving their prognosis into the "resectable" group. As an example only, patients placed in "borderline unresectable" or "unresectable" groups constitute approximately 20-30% of patients newly diagnosed with PDAC; the remainder have metastatic disease. Embodiments of the disclosure are particularly useful for targeting the SMA, which is the most frequently involved vessel in PDAC because of its intimate relationship with the head, the uncinate process, and body of the pancreas. Embodiments of the disclosure can also be used, for example, in patients with celiac axis or hepatic artery encasement or where surgical resection of a vein is not seen as possible. Embodiments of the invention can also be used to treat other cancers where resection is not favorable, such as sarcomas in the limbs where arterial resection would mean amputation. In specific embodiments, one or more devices of the disclosure are utilized to treat cancers that may or may not display positive margins.

Some embodiments of the disclosure can deliver controlled and targeted mild hyperthermia to diseased loci at the time of surgery, e.g., via radiofrequency electromagnetic waves or via a thin film-heating element that can be encased in an insulated cylinder. The insulated cylinder, which can encase the heating element, protects adjacent tissues and, therefore, limits collateral heating damage. The device can be used as part of a planned surgical procedure and/or can be used if vascular involvement is discovered once the patient is in the operating theatre, as vascular abutment maybe discovered only when the operation is already quite advanced (e.g., in transection of the pancreas or digestive transection).

Hyperthermic Vessel Treatment Devices

Embodiments of the disclosure provide multiple devices for the treatment of tumors at, around, or adjacent to a vessel of a mammal using hyperthermia. One embodiment of the device is illustrated in FIGS. 1, 2A-2E5 and FIGS. 19A-19C, and this device may be employed for tumors that are anatomically easily accessible, for example. As described herein, for this device the studies concerned pancreatic cancer because such a cancer commonly associates with vessels, although other types of cancers also associate with vessels and may be the target of the devices described herein.

Figure 20:
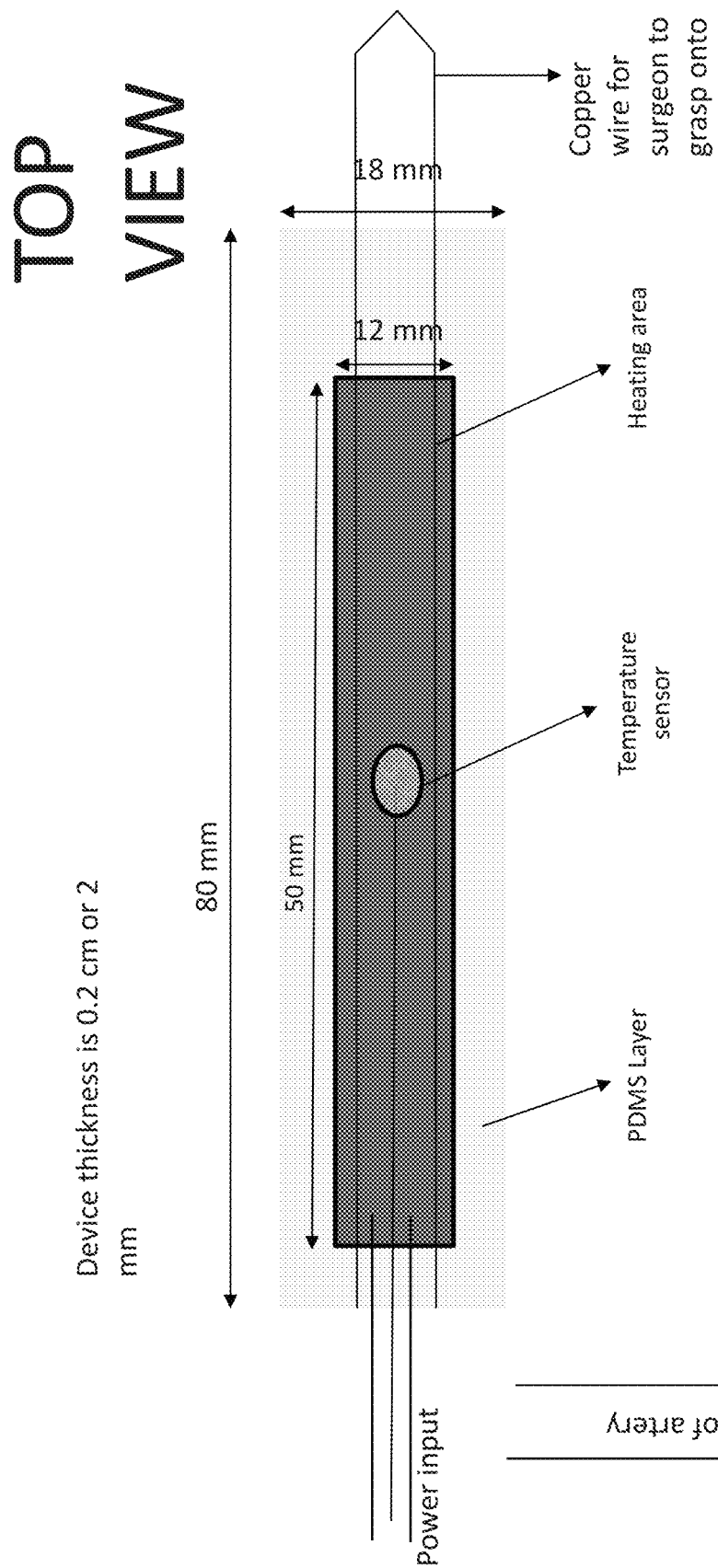
FIG. 20 depicts a top view of one embodiment of a device of the disclosure (for example, the device depicted in FIG. 19A).

Another embodiment of the device is illustrated in FIGS. 19D-19G and also in FIG. 20, and this device may be employed for tumors that are not anatomically easily accessible, as an example. Either device can be utilized for any type of cancer, any cancer of any origin, any stage of cancer, and any type of margins associated with any cancer. The cancer may be primary, metastatic, benign malignancy, sensitive to one or more therapies, refractory to one or more therapies, and so forth.

Sizes and dimensions of any device design embodiment encompassed herein can be adjusted according to patient and tumor section size.

Referring now to FIG. 1, one embodiment of the disclosure provides a hyperthermic vessel treatment device 200. The hyperthermic vessel treatment device 200 can include one or more semi-cylindrical shells 202a, 202b and one or more energy sources 204.

Hyperthermic vessel treatment device 200 can be fabricated in a variety of sizes to accommodate a variety of clinical situations.

In one embodiment, hyperthermic vessel treatment device 200 has a length (extending perpendicular from the page) of between about 2 cm and about 7 cm (e.g., between about 2 cm and 6 cm, between about 2 cm and 5 cm, between about 2 cm and 4 cm, between about 2 cm and 3 cm, between about 2.5 cm and about 3.5 cm, between about 3.5 cm and about 4.5 cm, between about 4.5 cm and about 5.5 cm, between about 5.5 cm and about 6.5 cm, and the like). In specific embodiments, a device can be tailored to fit from predicted positive cancer margins from patient scans, or different sizes, such as small, medium and large, can be utilized during surgery. Some methods of the disclosure encompass the step of determining the appropriate size and/or type of a device to be utilized.

Likewise, inner lumen 208 can have a variety of cross-sectional dimensions (e.g., diameters in circular cross-sections). The inner lumen 208 is the region occupied by the artery. For example, the inner lumen 208 can have a diameter of between about 0.5 cm and about 4 cm, such as between about 0.5 cm and 3.75 cm, 0.5 and 3.5 cm, 0.5 and 3 cm, 0.5 and 2.5 cm, 0.5 and 2.5 cm, 0.5 and 2 cm, 0.5 and 1.5 cm, 0.5 cm and 1.4 cm, 0.5 cm and 1.3 cm, 0.5 cm and 1.2 cm, 0.5 cm and 1.0 cm, 0.5 cm and 0.75 cm, 0.6 cm and 4 cm, 0.6 and 3.75 cm, 0.6 and 3.5 cm, 0.6 and 3 cm, 0.6 and 2.5 cm, 0.6 and 2 cm, 0.6 cm and 1.5 cm, 0.6 cm and 1.4 cm, 0.6 cm and 1.3 cm, 0.6 cm and 1.2 cm, 0.6 cm and 1.0 cm, 0.6 cm and 0.75 cm, 0.7 cm and 4 cm, 0.7 cm and 3.75 cm, 0.7 cm and 3.5 cm, 0.7 cm and 3.0 cm, 0.7 cm and 2.5 cm, 0.7 cm and 2.0 cm, 0.7 cm and 1.5 cm, 0.7 cm and 1.4 cm, 0.7 cm and 1.3 cm, 0.7 cm and 1.2 cm, 0.7 cm and 1.0 cm, 0.7 cm and 0.9 cm, 0.8 cm and 4.0 cm, 0.8 cm and 3.75 cm, 0.8 cm and 3.5 cm, 0.8 cm and 3.0 cm, 0.8 cm and 2.5 cm, 0.8 cm and 2.0 cm, 0.8 cm and 1.5 cm, 0.8 cm and 1.4 cm, 0.8 cm and 1.3 cm, 0.8 cm and 1.2 cm, 0.8 cm and 1.1 cm, 0.8 cm and 1.0 cm, 0.9 cm and 4.0 cm, 0.9 cm and 3.75 cm, 0.9 cm and 3.5 cm, 0.9 cm and 3.0 cm, 0.9 cm and 2.5 cm, 0.9 cm and 2.0 cm, 0.9 cm and 1.75 cm, 0.9 cm and 1.5 cm, 0.9 cm and 1.4 cm, 0.9 cm and 1.3 cm, 0.9 cm and 1.2 cm, 0.9 cm and 1.1 cm, 0.9 cm and 1.0 cm, 1.0 cm and 4.0 cm, 1.0 cm and 3.75 cm, 1.0 cm and 3.5 cm, 1.0 cm and 3.0 cm, 1.0 cm and 2.5 cm, 1.0 cm and 2.0 cm, 1.0 cm and 1.5 cm, 1.0 cm and 1.4 cm, 1.0 cm and 1.4 cm, 1.0 cm and 1.3 cm, 1.0 cm and 1.2 cm, 1.0 cm and 1.1 cm, 1.1 cm and 4.0 cm, 1.1 cm and 3.5 cm, 1.1 cm and 3.0 cm, 1.1 cm and 2.5 cm, 1.1 cm and 2.0 cm, 1.1 cm and 1.5 cm, 1.1 cm and 1.4 cm, 1.1 cm and 1.3 cm, 1.1 cm and 1.2 cm, 1.2 cm and 4.0 cm, 1.2 cm and 3.5 cm, 1.2 cm and 3.0 cm, 1.2 cm and 2.5 cm, 1.2 cm and 2.0 cm, 1.2 cm and 1.5 cm, 1.2 cm and 1.5 cm, 1.2 cm and 1.4 cm, 1.2 cm and 1.3 cm, 1.3 cm and 4.0 cm, 1.3 cm and 3.5 cm, 1.3 cm and 3.0 cm, 1.3 cm and 2.5 cm, 1.3 cm and 2.0 cm, 1.3 cm and 1.5 cm, 1.4 cm and 4.0 cm, 1.4 cm and 3.5 cm, 1.4 cm and 3.0 cm, 1.4 cm and 2.5 cm, 1.4 cm and 2.0 cm, 1.4 cm and 1.5 cm, 1.5 cm and 4.0 cm, 1.5 cm and 3.5 cm, 1.5 cm and 3.0 cm, 1.5 cm and 2.5 cm, 1.5 cm and 2.0 cm, 1.6 cm and 4.0 cm, 1.6 cm and 3.5 cm, 1.6 cm and 3.0 cm, 1.6 cm and 2.5 cm, 1.6 cm and 2.0 cm, 1.7 cm and 4.0 cm, 1.7 cm and 4.0 cm, 1.7 cm and 3.5 cm, 1.7 cm and 3.0 cm, 1.7 cm and 2.5 cm, 1.7 cm and 2.0 cm, 1.8 cm and 4.0 cm, 1.8 cm and 3.5 cm, 1.8 cm and 3.0 cm, 1.8 cm and 2.5 cm, 1.8 cm and 2.0 cm, 1.9 cm and 4.0 cm, 1.9 cm and 3.5 cm, 1.9 cm and 3.0 cm, 1.9 cm and 2.5 cm, 1.9 cm and 2.0 cm, 2.0 cm and 4.0 cm, 2.0 cm and 3.5 cm, 2.0 cm and 3.0 cm, 3.0 cm and 4.0 cm, 3.5 cm and 4.0 cm, and so forth.

Shells

Semi-cylindrical shells 202a and 202b can be sized to surround or substantially surround an anatomical vessel such as a blood vessel. Shells 202a and 202b can be fabricated from a variety of materials including metals (e.g., stainless steel), plastics, and the like using a variety of techniques including casting, molding, machining, thermomolding, thermosetting, injection molding, vacuum forming, additive manufacturing (also known as 3D printing), and the like.

Figures 2C, 2D:
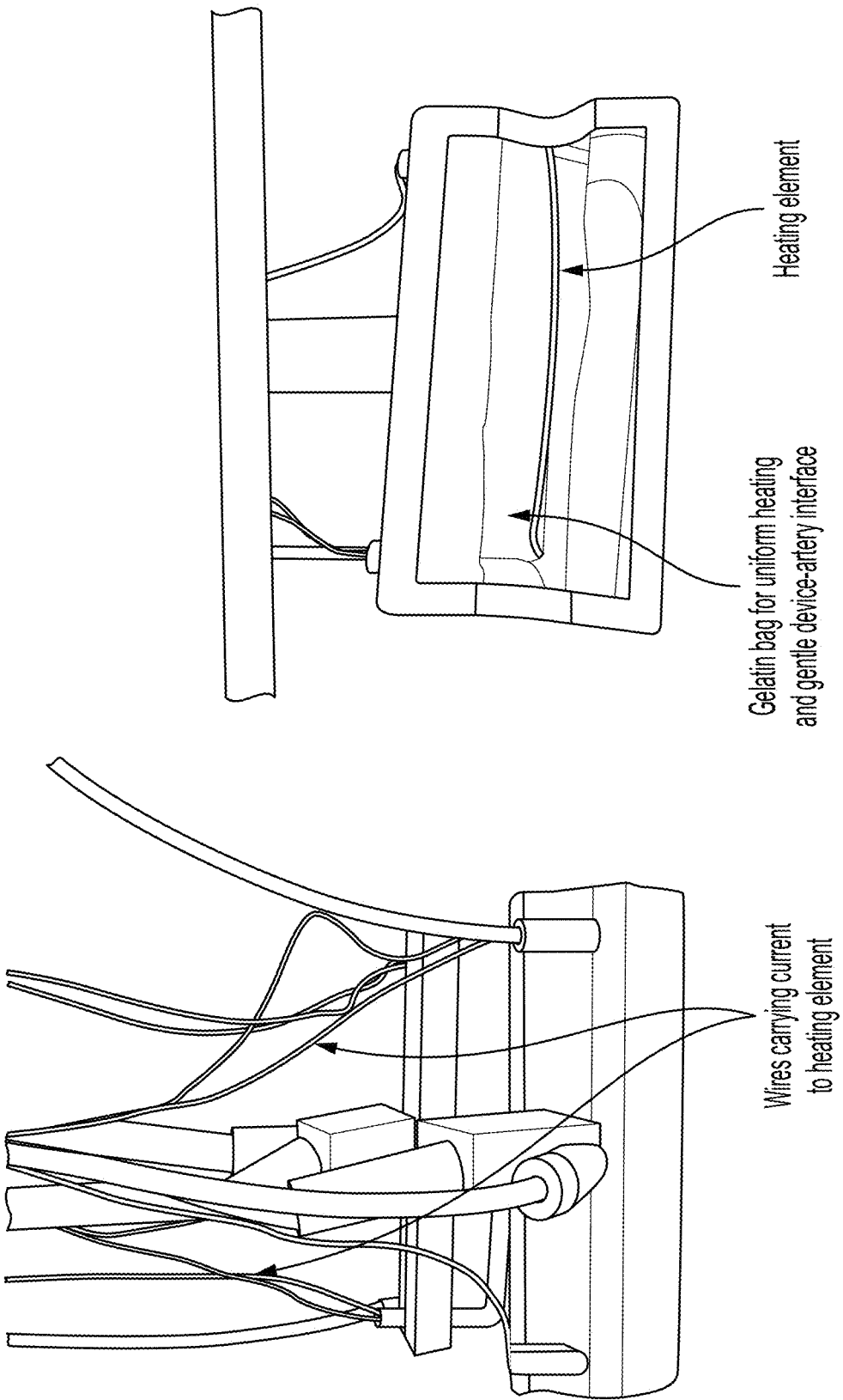
FIG. 2C is an image of the head of the device showing wires for incoming current, which can be used to adjust a heating rate of the artery via the heating element placed inside the device as depicted in FIG. 2D. A gelatin bag can be used to enable a gentle artery-device interface as well as consistent heating along the length of the device.

Shells 202a and 202b can be mounted on forceps as depicted in FIGS. 2A-2E5.

Energy Sources

Energy sources 204 can include any device capable of providing sufficient energy to heat tissue within the device to a hyperthermic temperature sufficient to diminish or prevent future tumor growth. One can incorporate RF and LED lights within the device, given that RF affects cancer cells and we are currently studying effect of LED light on cancer cells.

In one embodiment, the energy source 204 is a resistive (ohmic) heater.

In other embodiments, the energy source(s) 204 are radiofrequency (RF) energy generating units that can be adapted, configured, and/or programmed to generate monopolar, bipolar, capacitively coupled, and/or conductively coupled RF energy. The RF energy can have a frequency between about 0.3 MHz and about 100 MHz, such as between about 0.3 MHz and 90 MHz, between about 1 MHz and 75 MHz, between about 5 MHz and 50 MHz, between about 10 MHz and 50 MHz, between about 25 MHz and 100 MHz, between about 25 MHz and 75 MHz, between about 25 MHz and 50 MHz, between about 50 MHz and 100 MHz, between about 50 MHz and 75 MHz, and between about 75 MHz and 100 MHz.

Other suitable energy sources include coherent light sources, incoherent light sources, heated fluid sources, microwave generators (e.g., producing frequencies between about 915 MHz and about 2.45 GHz, between about 1 GHz and 2 GHz, and ultrasound generators (e.g., producing frequencies between about 300 KHZ and about 3 GHz, between about 500 KHz and 3 GHz, between about 1 MHz and 3 GHz, between about 500 MHz and 3 GHz, between about 1 GHz and 3 GHz, and so forth).

In particular, in FIG. 1, which encompasses one embodiment of a device of the disclosure, the device may include one or more diffusers, sensors, and/or control units. Any device of the disclosure may include one or more diffusers, sensors, and/or control units.

Diffusers

In FIG. 1, one or more diffusers 206 can be positioned inwardly between energy sources 204 and a central lumen 208 (which is occupied by the artery when in use) defined by the device 200 when shells 202a and 202b are closed. Diffusers 206 can be matched to energy sources 204 to promote even distribution of energy produced by energy sources 204. For example, diffuser 206 can act as a buffer and/or heat sink to smooth out fluctuations in energy produced by a resistive (Ohmic) heating element. Diffuser 206 can also scatter or refract energy produced by energy sources 204. In one embodiment, the diffuser 206 comprises gelatin.

Diffuser(s) 206 can comprise a liquid or a gel. The diffuser may be gelatin, such as in a gelatin bag. Suitable diffuser materials include at least water, heavy water, oil, peanut oil, glycerol, glycol, polypropylene glycol (PPG), polyethylene glycol (PEG), propylene glycol, ethylene glycol, dimethyl sulfoxide (DMSO), alcohol, ethanol, propanol, iso-propanol, carboxyl polyethylene polymer, hydroxyethyl xylose polymer, carboxyl methylcellulose, hydroxyethyl cellulose (HEC), the like, and combinations thereof. Exemplary diffuser materials are described in U.S. Patent Application Publication Nos. 2007/255362, 2010/0280582, and 2011/0300079 and U.S. Pat. No. 6,041,787, which are incorporated by reference herein in their entirety.

The diffusing material can be encapsulated or can be molded within shells 202. In one embodiment, at least the inner surface of the diffuser has a non-stick coating 206 such as polytetrafluoroethylene (PTFE) (e.g., TEFLON®, available from The Chemours Company of Wilmington, Delaware).

Sensors

One or more sensors 210 can be mounted inward toward a central lumen 208 defined by the device 200 when shells 202a and 202b are closed. Sensors 210 can include temperature sensors such as thermometers (e.g., infrared or non-contact thermometers), thermistors, thermocouples, optical temperature sensors, and the like that can measure a temperature at an outer surface of the diffuser 206, within diffuser 206, between diffuser 206 and energy sources 204, and/or at the outer surface of an anatomical vessel (and any tumor adjacent thereto). Sensors 210 can span part or the entirety of the inner surface of the semi-cylinders adjacent to the lumen 208. A variety of suitable sensors are described in U.S. Patent Application Publication Nos. 2005/0251120 and 2007/0010861.

Control Unit

Sensors 210 and/or energy sources 204 can be coupled to a controller. There may be control units that can be adapted, configured, and/or programmed to control operation of the one or more energy sources 204 to heat at least a portion of the anatomical vessel or a tumor adjacent thereto to a hyperthermic temperature sufficient to diminish or prevent future tumor growth.

In one embodiment, sensors 210 and/or energy sources 204 are communicatively coupled (e.g., through wired or wireless communication equipment and/or protocols) with the control unit. The control unit can be an electronic device programmed to control the of the one or more energy sources 204 to regulate the amount of heating of the anatomical vessel (and any tumor adjacent thereto). The control unit can be programmed to autonomously control energy sources 204 without the need for input from a medical professionals or can incorporate such inputs.

Control unit can be a computing device such as a microcontroller (e.g., available under the ARDUINO® OR IOIO™ trademarks), general purpose computer (e.g., a personal computer or PC), workstation, mainframe computer system, and so forth. Control unit can include a processor device (e.g., a central processing unit or "CPU"), a memory device, a storage device, a user interface, a system bus, and a communication interface.

Processor can be any type of processing device for carrying out instructions, processing data, and so forth.

Memory device can be any type of memory device including any one or more of random access memory ("RAM"), read-only memory ("ROM"), Flash memory, Electrically Erasable Programmable Read Only Memory ("EEPROM"), and so forth.

Storage device can be any data storage device for reading/writing from/to any removable and/or integrated optical, magnetic, and/or optical-magneto storage medium, and the like (e.g., a hard disk, a compact disc-read-only memory "CD-ROM", CD-Re Writable "CDRW", Digital Versatile Disc-ROM "DVD-ROM", DVD-RW, and so forth). Storage device can also include a controller/interface for connecting to system bus. Thus, memory device and storage device are suitable for storing data as well as instructions for programmed processes for execution on processor.

User interface can include a touch screen, control panel, keyboard, keypad, display, or any other type of interface, which can be connected to system bus through a corresponding input/output device interface/adapter.

Communication interface can be adapted and configured to communicate with any type of external device, including sensors. Communication interface can further be adapted and configured to communicate with any system or network, such as one or more computing devices on a local area network ("LAN"), wide area network ("WAN"), the Internet, and so forth. Communication interface can be connected directly to system bus or can be connected through a suitable interface.

Control unit can, thus, provide for executing processes, by itself and/or in cooperation with one or more additional devices, that can include algorithms for controlling energy sources 204 in accordance with the present invention. Control unit can be programmed or instructed to perform these processes according to any communication protocol and/or programming language on any platform. Thus, the processes can be embodied in data as well as instructions stored in memory device and/or storage device or received at user interface and/or communication interface for execution on processor.

Control unit can control the operation of the energy sources 204 in a variety of ways. For example, the control unit can modulate one or more parameters of electrical power provided the energy sources 204 such that less current will produce less energy. Alternatively, the control unit can transmit instructions and/or parameters to the energy sources 204 for implementation by the energy sources 204.

The principles of how to use feedback (e.g., from a temperature sensor) in order to modulate operation of a component are described, for example, in Karl Johan Åström & Richard M. Murray, *Feedback Systems: An Introduction for Scientists & Engineers* (2008). *Hyperthermic Treatment of Vessels and Surrounding Tumors*

Embodiments of the disclosure can heat at least a portion of the anatomical vessel or a tumor adjacent thereto to a hyperthermic temperature sufficient to diminish or prevent future tumor growth. In one embodiment of the invention, at least a portion of the anatomical vessel or a tumor adjacent thereto are heated to a temperature sufficient to diminish or prevent future tumor growth without destroying the anatomical vessel. Without being bound by theory, it is believed that heating of the anatomical vessel or a tumor adjacent thereto to a temperate between about 370° C. and 46° C. achieves this result. In one embodiment, the controller is programmed to deliver a thermal dose sufficient to produce a boundary temperature between about 44° C. and about 46° C. for about 10 minutes or less or longer. Longer dwell times or cooling-warming cycles can also be utilized, such as 1, 2, 3, 4, 5, 6, 7, 8, 9, 11, 12, 13, 14, 15, 16, 17, 18, 19, 20, or more minutes, for example.

In specific cases, the device provides a temperature of the anatomical vessel or a tumor adjacent thereto to about 35° C., 36° C., 37° C., 38° C., 39° C., 40° C., 41° C., 42° C., 43° C., 44° C., 45° C., 46° C., 47° C., 48° C., 49° C., or more. In certain cases, the device provides a temperature of the anatomical vessel or a tumor adjacent thereto to a range of about 35° C. to 49° C., 35° C. to 48° C., 35° C. to 47° C., 35° C. to 46° C., 35° C. to 45° C., 35° C. to 44° C., 35° C. to 43° C., 35° C. to 42° C., 35° C. to 41° C., 35° C. to 40° C., 35° C. to 39° C., 35° C. to 38° C., 35° C. to 37° C., 35° C. to 36° C., 36° C. to 49° C., 36° C. to 48° C., 36° C. to 47° C., 36° C. to 46° C., 36° C. to 45° C., 36° C. to 44° C., 36° C. to 43° C., 36° C. to 42° C., 36° C. to 41° C., 36° C. to 40° C., 36° C. to 39° C., 36° C. to 38° C., 36° C. to 37° C., 37° C. to 49° C., 37° C. to 48° C., 37° C. to 47° C., 37° C. to 46° C., 37° C. to 45° C., 37° C. to 44° C., 37° C. to 43° C., 37° C. to 42° C., 37° C. to 41° C., 37° C. to 40° C., 37° C. to 39° C., 37° C. to 38° C., 38° C. to 49° C., 38° C. to 48° C., 38° C. to 47° C., 38° C. to 46° C., 38° C. to 45° C., 38° C. to 44° C., 38° C. to 43° C., 38° C. to 42, 38° C. to 41° C., 38° C. to 40° C., 38° C. to 39° C., 39° C. to 49° C., 39° C. to 48° C., 39° C. to 47° C., 39° C. to 46° C., 39° C. to 45° C., 39° C. to 44° C., 39° C. to 43° C., 39° C. to 42° C., 39° C. to 41° C., 39° C. to 40° C., 40° C. to 49° C., 40° C. to 48° C., 40° C. to 47° C., 40° C. to 46° C., 40° C. to 45° C., 40° C. to 44° C., 40° C. to 43° C., 40° C. to 42° C., 40° C. to 41° C., 41° C. to 49° C., 41° C. to 48° C., 41° C. to 47° C., 41° C. to 46° C., 41° C. to 45° C., 41° C. to 44° C., 41° C. to 43° C., 41° C. to 42° C., 42° C. to 49° C., 42° C. to 48° C., 42° C. to 47° C., 42° C. to 46° C., 42° C. to 45° C., 42° C. to 44° C., 42° C. to 43° C., 43° C. to 49° C., 43° C. to 48° C., 43° C. to 47° C., 43° C. to 46° C., 43° C. to 45° C., 43° C. to 44° C., 44° C. to 49° C., 44° C. to 48° C., 44° C. to 47° C., 44° C. to 46° C., 44° C. to 45° C., 45° C. to 49° C., 45° C. to 48° C., 45° C. to 47° C., 45° C. to 46° C., 46° C. to 49° C., 46° C. to 48° C., 46° C. to 47° C., 47° C. to 49° C., 47° C.-48° C., or 48° C. to 49° C., for example.

In specific cases, a thermal dose is provided for about, for at least, or for no more than 0.5, 1, 1.5. 2. 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, or more minutes.

EXAMPLES

The following examples are presented in order to more fully illustrate the preferred embodiments of the disclosure. They should in no way, however, be construed as limiting the broad scope of the disclosure.

Example 1

Embodiments of Hyperthermic Vessel Treatment Device Methods
Cell Lines

Human PDAC lines, PANC-1 and AsPc-1, cells were obtained from American Type Culture Collection (ATCC). PANC-1 and AsPc-1 cells were maintained in DMEM with 10% FBS.

Human umbilical vein endothelial cells (HUVEC) were maintained in vascular cell basal medium supplemented with 0.2% Bovine Brain Extract, 5 ng/mL rh EGF, 10 mM L-glutamine, 0.75 units/mL Heparin sulfate, 1 µg/mL Hydrocortisone hemisuccinate and 2% Fetal Bovine Serum, and 50 µg/mL Ascorbic acid.

Human microvascular endothelial cells (HMVEC) (Lonza, Walkersville, MD, USA) were incubated in endothelial cell basal medium (EBM, Lonza) supplemented with endothelial cell growth medium (EGM) microvascular bullet kit containing 25 ml FCS, 0.5 ml hEGF, 0.5 ml hydrocortisone, 0.5 ml gentamicin, 0.5 ml bovine brain extract (Lonza). Cells were grown to confluence in T75 flasks at 37° C. in humidified air with 5% $CO_2$ prior to being harvested with trypsin-EDTA (Lonza). Cells were maintained in a 95% humidified atmosphere of 5% $CO_2$ at 37° C. and 2% penicillin-streptomycin solution was added to the media of all cell lines.
Animal Models Female Yucatan miniature swine (Sinclair Bioresources, Auxvasse, MO) were housed and raised according to Institutional Animal Care and Use Committee (IACUC) guidelines at the Baylor College of Medicine. No special diet was given. At the time of testing, pigs were 12 months of age and weighed 62-70 kg.

Scanning Electron Microscopy (SEM)

Cells were fixed by washing thrice with 0.1 M sodium cacodylate buffer (CDB) followed by incubation in 2.5% glutaraldehyde for 25 min at room temperature. Cells were washed twice in 0.1 M CDB and subjected to an ethanol series for dehydration. The cells were then incubated in 1:1 t-butanol:ethanol mixture for 5 min and mounted on carbon tape upon an SEM stub. Immediately before imaging the samples were sputter coated with 50% platinum/50% palladium at a thickness of 5±0.2 nm to ensure good electrical conductivity.

Immunohistochemical Evaluation

Tissue samples were fixed in formalin and processed in paraffin blocks and sectioned using standard techniques. Tissue slides were stained with H&E, Verhoeff-Van Gieson (Elastic fibers) and Cleaved PARP (apoptosis). Histology slides were imaged using a NIKON® ECLIPSE® TE2000-U microscope fitted with a NIKON® digital sight DS-Fi1 video camera. All slides were imaged at a fixed 167 ms exposure time.

In Vitro Time-Resolved Cytotoxicity Testing

Cytotoxicity was quantified using DRAQ7® dye (Biostatus Ltd, UK) staining, which is a far-red fluorescent dye. Cells were seeded at a concentration of 100,000 cells per well in GREINER BIO-ONE® CELLSTAR® tissue culture 6-well plate for 24 h. Plates were then placed into a water bath and heated to the given thermal dose. After 10 mins of water bath hyperthermia, 3 µM concentration of DRAQ7 was placed in the cell medium before being gently pipetted to ensure thorough mixing. High throughput, time-lapse-based experiments were performed within 10 min of adding the DRAQ7® dye using an IMAGEXPRESS® Micro XL microscope (GE Healthcare, USA). Images were obtained once every hour for 24 h of over 4,000 cells at each time point. Cells were imaged at 20× magnification in two channels: the DRAQ7® channel (Far red) and the brightfield channel. At the end of the time-lapse experiment, the cells were placed in hot water to induce 100% cell death before an additional set of images was then collected, from which a measure of the total number of cells in each well was obtained. Cell death was quantified by the automated measure of the DRAtQ7® signals at each time point using METAXPRESS® 5.3.0.5 and METAXPRESS® POWERCORE™ 1.3.0.3 software (Molecular Devices, USA) and was displayed as a percentage of the total cells within each well.

Device Design

In certain embodiments, a device designed for tight anatomical positions is provided as follows:

A thin electrical heating pad and a thin temperature sensor were placed in liquid PDMS or silicone and the polymers were allowed to dry. The temperature sensor was placed near the surface which will be in contact with the cancer layer. A thin sheet of aluminum and a thicker PDMS or silicon layer was incorporated on the non-heating side to limit the amount of heat given out to anatomy which does not require heating. The end device is flexible and can be positioned easily on cancer layers where there is little space.

An embodiment of the device was designed using AUTOCAD® 2016 software (Autodesk, USA) and printed using Form 1+High-Resolution 3-D printer (Formlabs, USA) using a polymer containing a mixture of (meth)acrylated monomers, (meth)acrylated oligomers and photoinitiators. Applicant integrated the novel head design with a commonly used surgical cauterizing instrument for familiar handling of the device. The head of the device was designed to be as streamlined as possible so that easy placement of the device could occur as the SMA is a deep-seated vessel which is surrounded by many important anatomical structures.

Figure 4A:
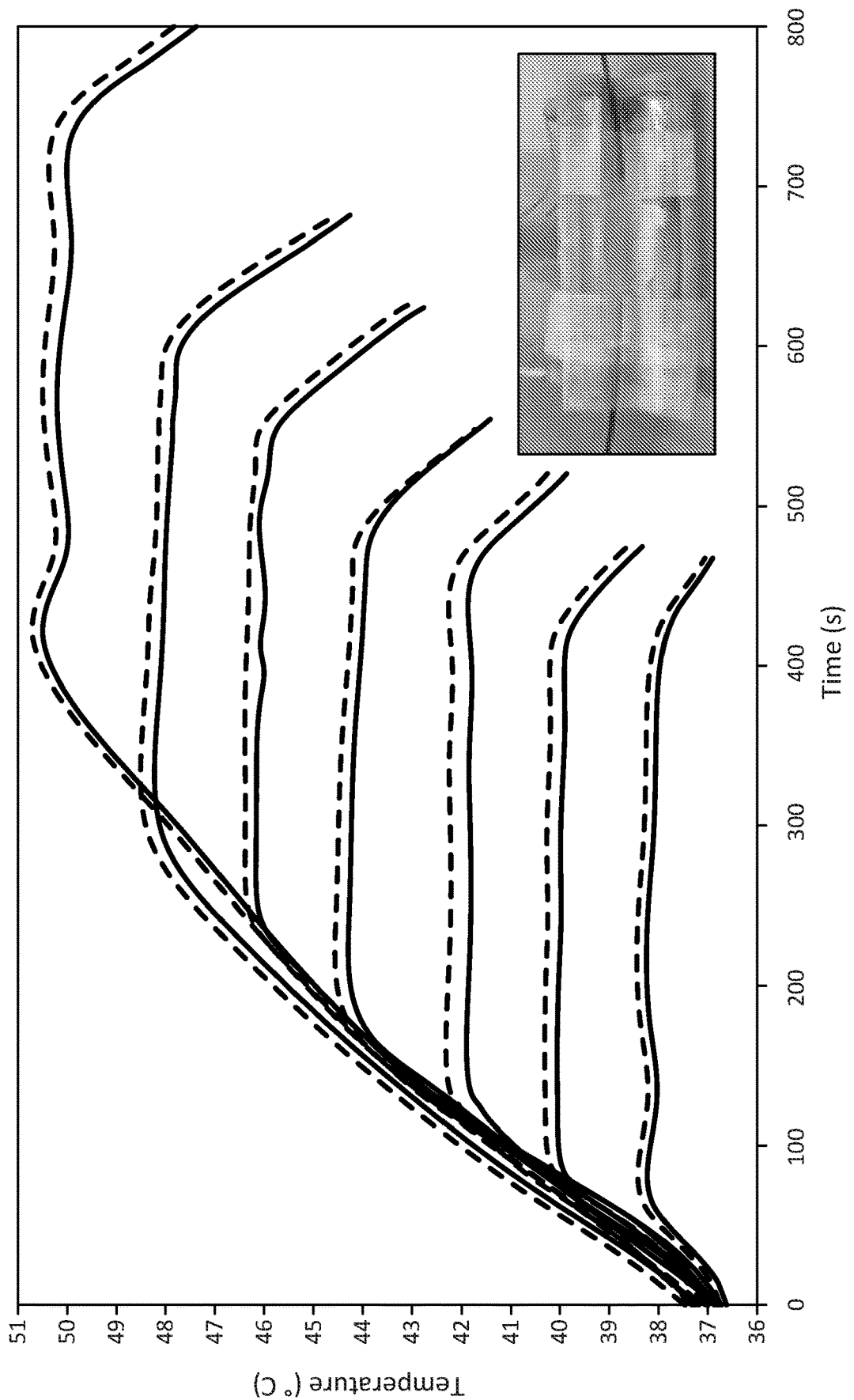
FIGS. 4A and 4B depict heating control and consistency in heating according to an embodiment of the invention.
Figure 4B:
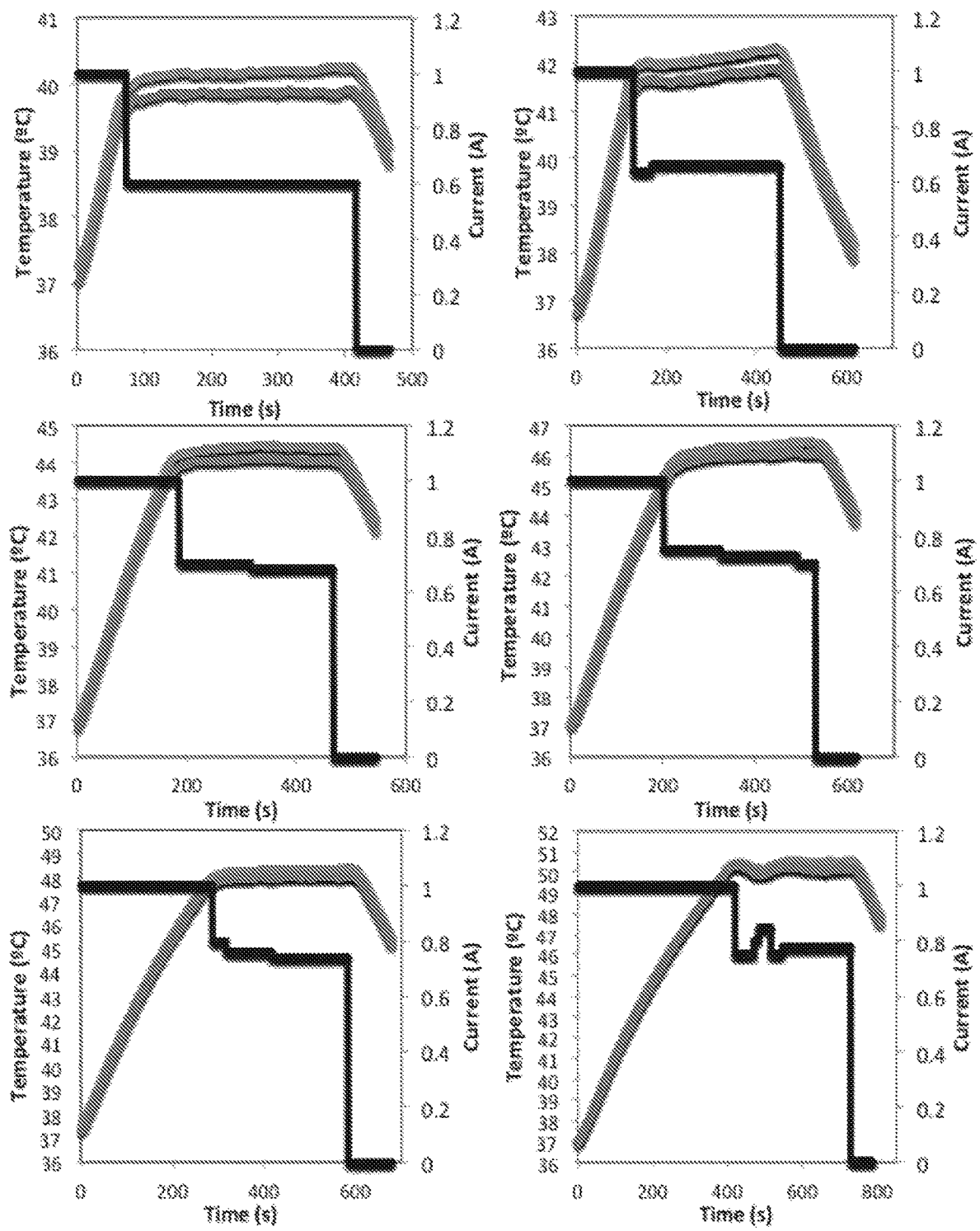

The device head was designed to be large enough to accommodate a heating element and a gelatin bag. This ensured excellent temperature modulation via alternating the current passed through the electric heating element and also even heat distribution across length of the device as depicted in FIGS. 4A and 4B. The device head was designed to be 6 cm in length, as an example, as this is the approximate width of the pancreas overlying the SMA. Hence, the device would be able to heat the whole length of the SMA likely to be encased by tumor during a single treatment cycle as depicted in FIGS. 2A-2E5. However, Applicant also envisages that various sizes of the device can be provided for patients of different sizes and that multiple uses of the device on the tumor site may occur. Applicant recently designed a smaller device that incorporates a 3 cm length heating head to test if this allowed for greater maneuverability and positioning of the device during surgery and also if it would lower the chance of blood heating in the artery, as it has less of a distance to travel under potential hyperthermic conditions.

Examples of Results

Embodiments of the device are used to heat the tumor that remains after positive-margin resection on the SMA during surgery. The phenomenon of cancer cells having an increased susceptibility to heat when compared to normal cells aids in cancer cell killing, which is supported by data provided at least in FIGS. 3A-3F. It shows high susceptibility and drastic morphological alterations of cancer cells when exposed to various temperatures (37° C. to 46° C., for example). Non-malignant cell lines, such as endothelial cells display less drastic responses. Furthermore and without being bound by theory, Applicant considers that the arterial blood flow is advantageous in providing a heat sink to dissipate heat away from the inside lumen of the artery and, therefore acts as a protective mechanism for the artery when undergoing treatment with the device.

The Effect of Hyperthermia on the Cells of the PDAC-Mesenteric Artery Environment In vitro investigation was carried out to establish an approximate thermal dose that eliminated PDAC cell lines whilst minimizing the effects on healthy tissues.

1. Temperature-Dependent Cell Death

Initial in vitro studies allow the determination of thermal doses needed for the application of embodiments of the invention. The percentage of cell death induced by thermal doses of 42° C., 44° C. and 46° C. for 10 minutes after an initial thermal increase from 35° C. (which took 5 minutes) were investigated and are depicted in FIG. 3A-3F.

In-vitro population wide cytotoxicity studies involving numerous cells involved in the PDAC-SMA environment indicated that a thermal dose of 44° C.-46° C. for 10 min would induce the greatest cytotoxicity in cancer cell lines whilst limiting the effects seen in normal cell lines as depicted in FIG. 3A-3F. These studies approximate the true biological environment, which includes arterial blood flow and the extra-cellular environment, and provide some insight into the thermal dose required for greatest differential in cell death between malignant and healthy cells.

Device Placement in In Vivo Swine Models

The device was designed so it can be positioned on the SMA after palpation at the time of the Kocher maneuver (which permits exposure of structures behind duodenum and pancreatic head). An additional dedicated skeletonization of the SMA after the Kocher maneuver would be also employed, in specific embodiments. These are commonly performed techniques used by surgeons to assess the relationship of a pancreatic head tumor to the superior mesenteric artery, and experimental pancreatic surgeons will be trained in the surgical techniques to accurately place the device intra-operatively.

1. Thermal Dynamics of Device in Ex Vivo and Deceased Swine Model In Situ

Insight into thermal dynamics within the system provides valuable information to enable optimal thermal dose administration to the cancer layer whilst simultaneously minimizing unwanted damage to the intima and lumen of the SMA. Device testing on ex vivo and deceased in situ porcine models will determine the heat differential in "dry" tissue, where blood flow is removed as a variable. Additionally, the design can be tested to see if it enables accurate placement of the device around the SMA.

2. Thermal Dynamics of Device in an Ex Vivo Model

Figure 6A:
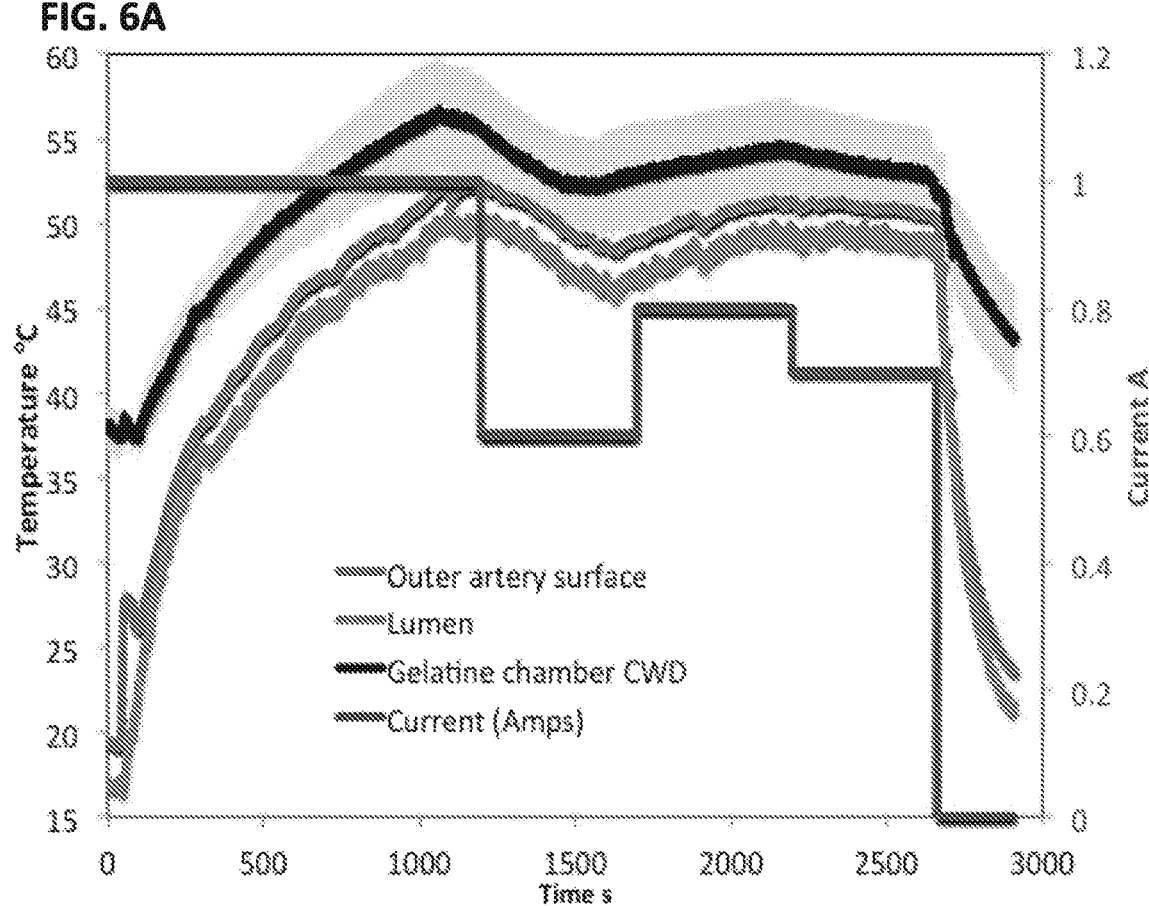
FIGS. 6A-6B depict heating dynamics of the device and aorta ex vivo.
Figure 6B:
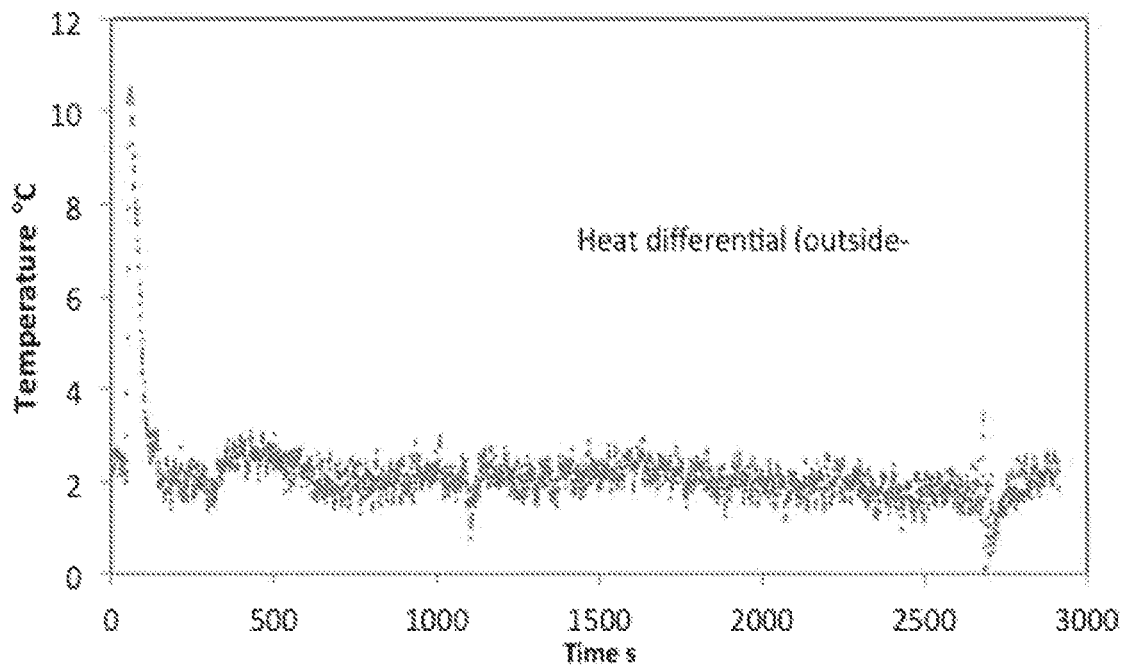
Figure 7C:
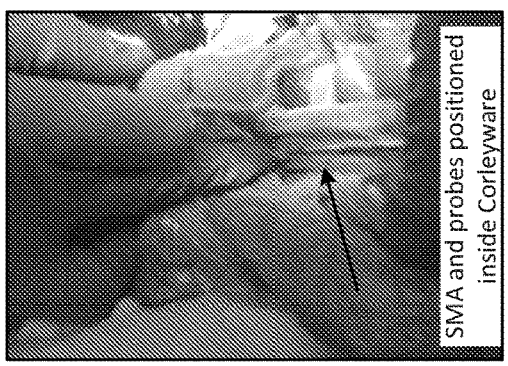
FIGS. 7A-7E depict in vivo testing in a deceased swine model.
Figure 7B:
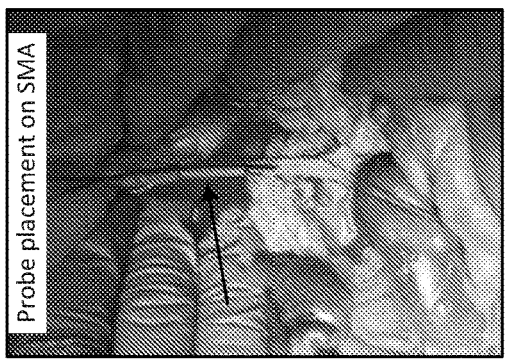
Figure 7A:
Figure 7E:
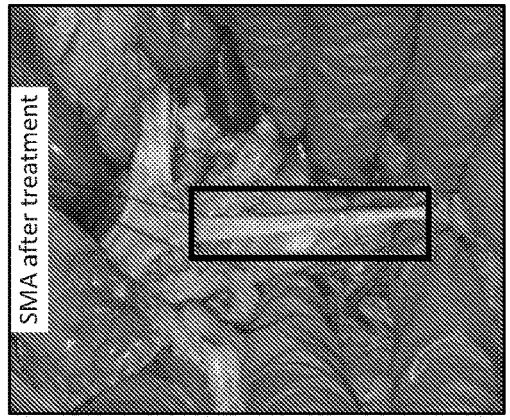
Figure 7D:
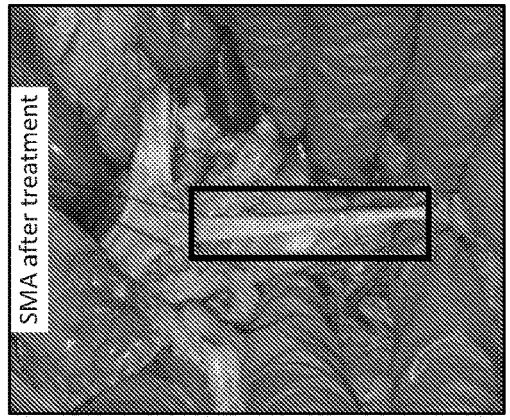
Figure 8:
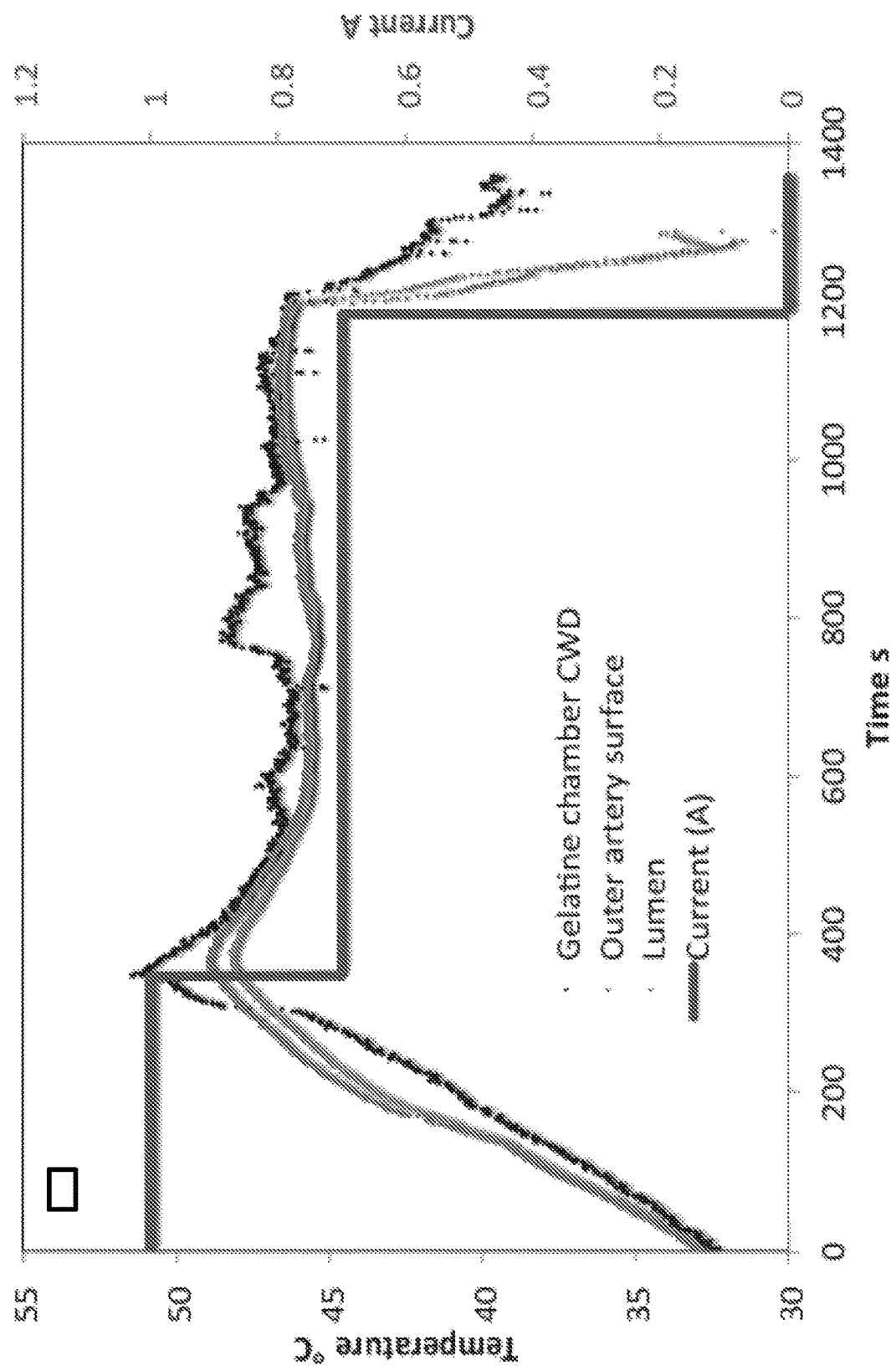
FIG. 8 depicts heating dynamics of devices according to embodiments of the invention and SMA in a deceased swine model in situ. The black curve represents a heating rate of a gelatin chamber inside the device. The dark red curve and blue curve show a heating differential between the outside SMA surface (red curve) and inside the SMA lumen (blue curve). The bright red line shows current adjustment throughout treatment to heat to 46° C. between 0-400 seconds and then to produce constant 46° C. temperature between 400-1200 seconds, before turning the device off at 1200 seconds. The black curve displays fluctuations due to the device losing heat when outer surfaces of the device are in contact with surrounding tissues.

The aorta was used in the ex vivo experiments as it represents a good model for cancer encasement of the SMA. The aorta is 1-2 mm thicker than the SMA, which models the extra thickness tumor encasement would create. Without blood flow present, which is expected to increase the heat differential between outside surface and lumen of artery even further, there is a constant differential of approximately 2° C. as depicted in FIGS. 6A and 6B, which is primarily due to the thick artery wall of the aorta.

3. Thermal Dynamics of Device in Deceased Swine Model In Situ

The next step was to establish whether the current design of the device enabled accurate placement of the device around the SMA. This is best established in in situ, where the SMA needs to be exposed and several proximal anatomical structures, such as the pancreas, duodenum and connective tissue need to be negotiated in order to achieve accurate placement of the device. Additionally, the moist in situ environment would allow more accurate SMA heating data to be obtained.

Firstly, accurate placement of the device was achieved with the current design of the device. A heat differential of 0-0.8° C. was observed during device heating. This differential was lower than what was achieved in aorta ex vivo testing, most probably due to the thinner SMA wall. The appearance of the SMA was unchanged from before treatment as depicted in FIG. 7. There are also no observable differences between the appearances of SMA artery that had been inside the device when compared to regions of the same artery that had not undergone hyperthermia. Elasticity before and after was tested via pulling forces being applied and no observable differences were seen. The moist in situ environment kept the SMA moist throughout and after the procedure.

Effect of the Blood Heat Sink on Heating Dynamics in an In Vivo Swine Model

Experiments testing heating dynamics of the device-SMA system until now have been performed either in ex vivo SMA samples or in deceased in situ swine models. Although these studies were informative regarding issues such as how the current design of the device is positioned in situ, one can consider the important effect of pulsatile blood flow that is seen in a live patient. Therefore, Applicant exposed the femoral artery in a live swine model to perform testing when pulsatile blood flow is present.

A shortcoming of current various heating techniques in cancer therapy devices, such as RF ablation, is the limited performance adjacent to large blood vessels (diameter >3 mm). When the heating occurs near large vessels, the blood flow drags thermal energy away from the target tissue. This is a heat sink effect that can change both the shape and maximum volume that can be treated. In fact, the distance of the blood vessels from the tumor determines the location of the maximal tissue temperature. As a result, tumors in the vicinities of large vessels are associated with high recurrence rates. Without being bound by theory, Applicant considers that blood flow through the SMA lumen is advantageous in this instance, as it will increase heat differential between outside cancer layer and inside healthy vasculature.

In addition to obtaining information regarding the effect of the heat sink, experiments in live porcine models determine whether the device can be accurately fitted to a vessel without major occlusion. Late effects, such as delayed thrombosis or ischemic colitis will be investigated during upcoming pig survival studies. Investigating the heating dynamics with specific consideration of blood flow characteristics along with the size of the patient and their SMA, and the thickness of the remaining positive margin provides powerful insight into the heat dynamics within a given system and will enable personalized treatment for various patients. Applicant investigated the action of the device when in contact with several major arteries in a porcine model to obtain temperature profiles of cancer and vessel interfaces as a function of time.

Figure 9A:
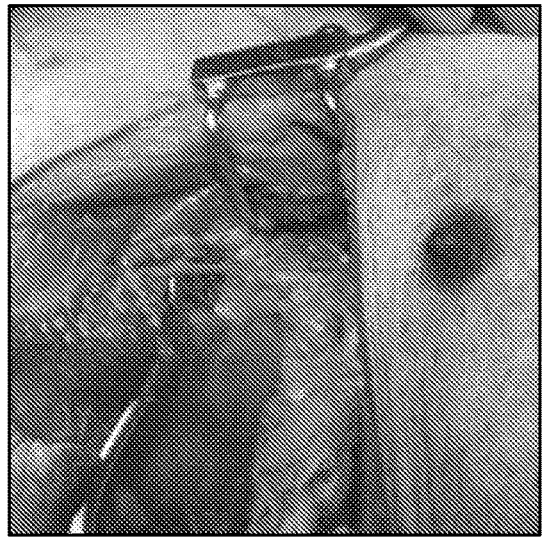
FIGS. 9A-9D depict the positioning of an embodiment of a hyperthermia device to investigate the effect of the blood heat sink on device heating dynamics.
Figure 9B:
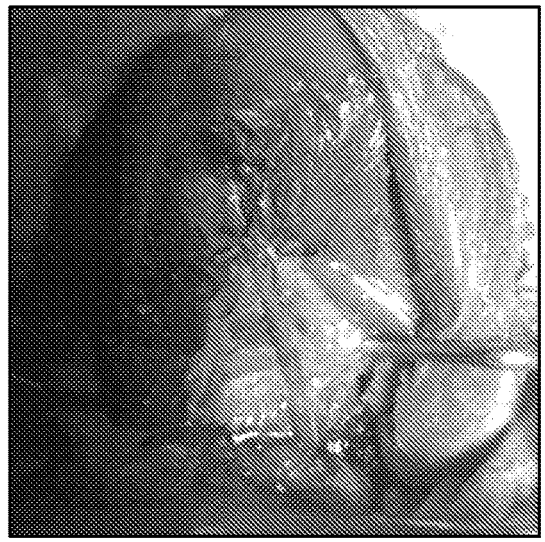

The femoral artery (FA) of a 62-70 kg female Yucatan miniature swine under anesthesia was exposed for device placement as depicted in FIGS. 9A and 9B. The femoral artery was chosen for device testing, as it is more superficial than the SMA and also similar in size to the SMA in humans and will be sufficient to provide proof of principle regarding the blood flow "heat sink" effect.

Figure 9C:
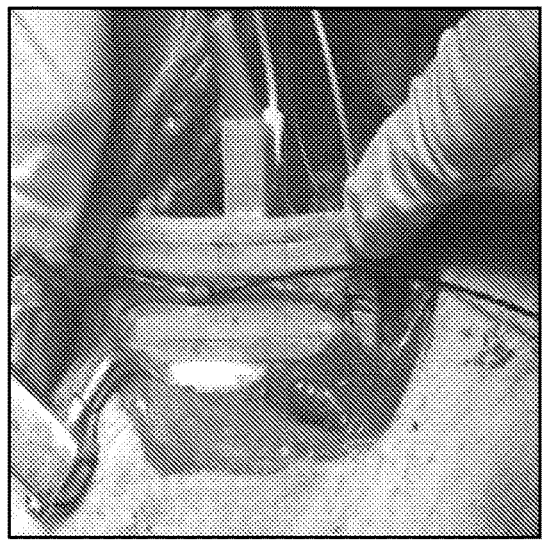
Figure 9D:
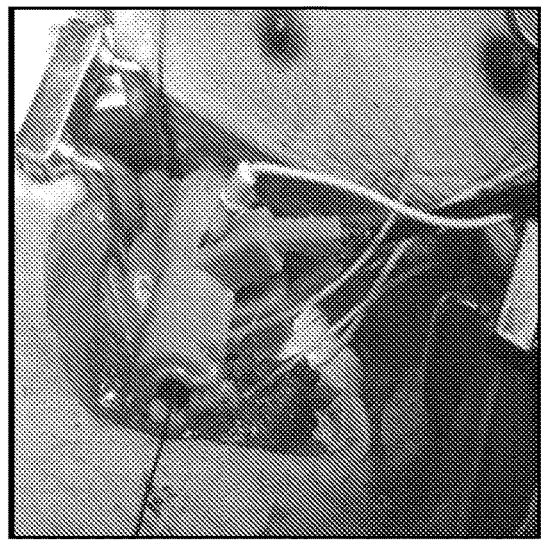
Figure 10A:
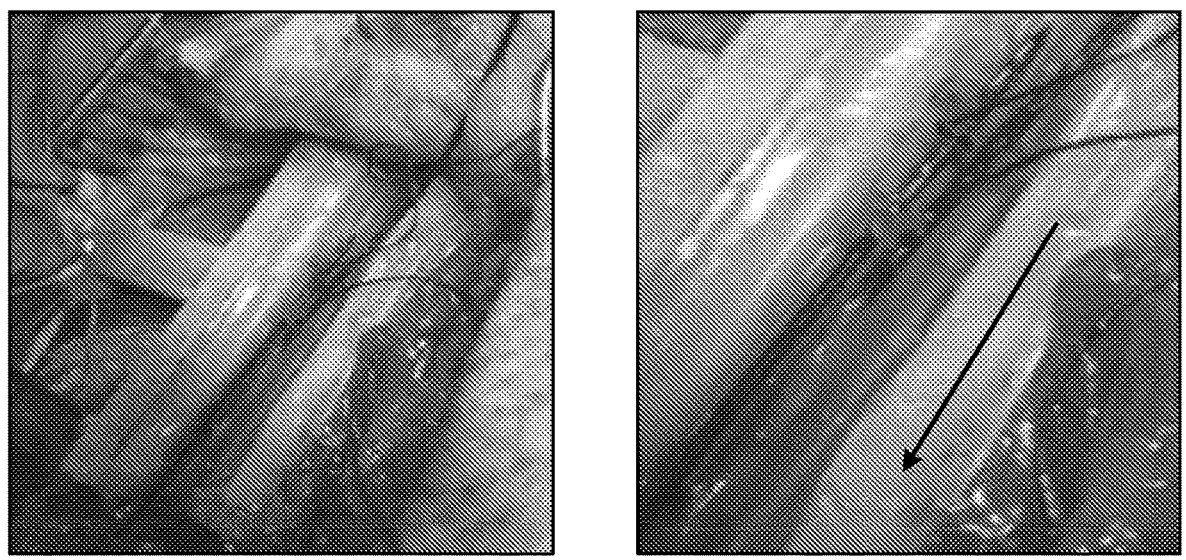
FIGS. 10A-10B depict the effect of the blood heat sink on heating dynamics in the femoral artery in vivo.
Figure 10B:
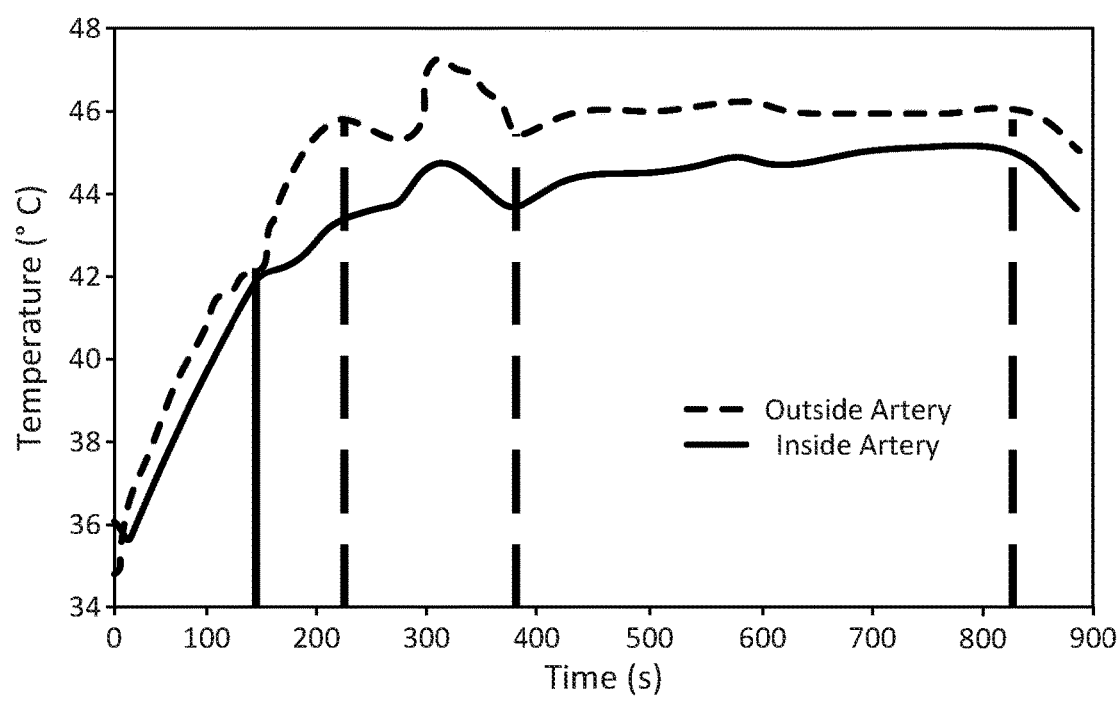

An optical temperature probe was loosely stitched onto the outside surface of the artery to ensure minimal movement during testing. A second probe was inserted into the lumen of the artery before the device was placed around the artery as depicted in FIGS. 9C and 9D and current was passed through the device to induce a local thermal dose.

The differential between the inside lumen and outside surface of the FA when blood is flowing was shown to be greater (~1.5-2° C. when the outside surface of the FA was heated to 46° C.) when compared to the differential in a deceased swine (0-0.8° C. differential at 46° C. in SMA) or in an ex vivo swine sample (~2° C. differential at 46° C. in an aorta sample where the differential is expected to be larger due to a greater thickness of vessel wall). These results indicate that the heat sink provided by blood flow in major arteries will enable a protective effect for the inside lumen whilst the outside cancer layer is heated. This will mean that the outside cancer layer can possibly be exposed to higher thermal doses, increasing kill efficacy during device treatment.

The effect of the blood "heat sink" can be further enhanced with the use of a localized blood cooling aid upstream of the device and/or a systemic dose of adrenalin to increase SMA blood flow.

An additional design of the device was also tested that incorporated a 3 cm length heating head rather than the traditional 6 cm head. Applicant considered that this shorter distance through which blood traveled under hyperthermia would reduce blood heating and would enhance the heat sink even further. This more streamlined design would also allow surgeons increased intra-operative maneuverability of the device. FIGS. 13A-13E show that a shorter device allowed for increased ease in positioning onto the femoral artery and also allowed for an enhanced heat sink effect.

Arterial Pathological Analysis

One embodiment of the disclosure is to intra-operatively deliver a thermal dose to the outside tumor layer that is sufficient to destroy cancer cells and to delay or eliminate recurrence of the tumor while avoiding significant damage to the underlying artery in order to maintain the function of downstream tissues and organs. Additionally, thrombosis of the blood traveling through the device should be avoided. The existence of arterial pathology following inventive treatment was evaluated by histology following the excision of the femoral artery after treatment.

FIGS. 14A-14H show a histology section through a FA of a pig that includes areas that had and had not undergone hyperthermia (46° C. for 10 mins). No obvious pathological features exist in the tunica intima, media, or adventitia immediately after treatment at this thermal dose. SEM imaging was also performed on the tunica intima layer of the vessel and no significant differences were observed immediately after treatment when compared to untreated FA sections. These are useful results, as this system does not contain the cancer layer and, therefore, the outside of the FA was in near direct contact with the gelatin bag. To test delayed onset of thrombosis, Applicant administer a systemic dose of heparin to prevent immediate or delayed thrombosis due to heating in pig survival studies.

Significance of Certain Embodiments

Vascular, and in particular arterial, invasion is a key factor in the resectability of PDAC tumors and, therefore, often dictates a patient's prognosis and survival. Applicant described the specific design and functionality of an innovative new device to treat PDAC patients with tumors with arterial involvement, and thus aim to move their treatment placement from "borderline resectable" and "unresectable" into the "resectable" group.

The data indicates that a more mild hyperthermia, e.g., in the range of about 46° C. for 10 minutes on tumors enclosing the SMA in PDAC patients may be one useful thermal dose that results in a longer period of time between surgery and tumor recurrence. This provides more recovery time before being able to commence chemotherapy regimens and a greater probability of achieving surgical result commensurate with curative intent.

In some embodiments, one can consider techniques to increase the blood cooling effect by introducing a localized cooling aid such as a cooling pack (e.g., between about 33° C. and about 36° C.) upstream of the hyperthermia, which would cool the encased artery as the device is heating the outside cancer layer. Applicant considers that upstream cooling can increase the heat differential between the cancer layer outer surface and the lumen of the vessel, in specific embodiments.

The efficacy of the device may be improved by the incorporation of chemotherapeutic drugs into the inner surface of the device. Incorporation of various heating moieties (such as metallic nanoparticles) will enhance the heating effect seen on contact with the tumor. Both drugs and nanoparticles can be delivered homogeneously on the tumor section encompassing the artery via the use of micro-needles or sponge delivery system, such as intercalated chemotherapeutics into various polymers such as PLA or biocompatible silk scaffolds.

Example 2

Mild Hyperthermia Device to Treat Vascular Involvement in Cancer Surgery

Surgical margin status in cancer surgery represents an important factor affecting the overall prognosis of the patient. The risk of adverse patient outcomes and surgical-margins recurrence is usually greatly minimized if the surgeon is able to achieve a grossly and pathologically negative margin during cancer surgery (Pawlik, et al., 2005). Unfortunately, there are many cancers for which negative margins cannot be surgically achieved at the time of diagnosis due to various factors, including tumor involvement of critical anatomical structures (Molina, et al., 2017; Miyazaki, et al., 2007; Mokdad, et al., 2017; Schmalbach, et al., 2016; Rich, et al., 2011; Waked, et al., 2017; Kato, et al., 2012; DeWitt, et al., 2004; Soriano, et al., 2004; Yeo, et al., 1997; Bottger, et al., 1998). Such locally advanced invasion may constitute a contraindication to surgery, and if surgery is attempted, patients stand at high risk for early tumor recurrence and further disease progression.

Any device designs of this disclosure may be utilized for the treatment of all cancers, although pancreatic cancer is employed as a model in the disclosed studies. Tumor involvement of major vasculature represents a perplexing problem that increases both surgical and oncologic risks for poor outcomes, with significant likelihood of a positive surgical margin (Molina, et al., 2017; Miyazaki, et al., 2007; Mokdad, et al., 2017; Schmalbach, et al., 2016; Rich, et al., 2011; Waked, et al., 2017; Kato, et al., 2012; DeWitt, et al., 2004; Soriano, et al., 2004; Yeo, et al., 1997; Bottger, et al., 1998). This is seen in a wide range of cancers including, but not limited to, paragangliomas (Schmalbach, et al., 2016), hepatocellular carcinoma (Hemming, et al., 2004), pancreatic ductal adenocarcinoma (PDAC) (Arslan, et al., 2001; Megibow, et al., 1995), perihilar cholangiocarcinoma (Molina, et al., 2017; Miyazaki, et al., 2007), neuroblastoma (Rich, et al., 2011), leiomyosarcoma (Kato, et al., 2012), retroperitoneal sarcoma (Schwarzbach, et al., 2006) and Kaposiform hemangioendothelioma (Kato, et al., 2012). Venous involvement can sometimes, but not always, be addressed by surgical resection and reconstruction of the vessels affected, such as in the case of hepatocellular carcinoma which has invaded the portal vein, hepatic vein or inferior vena cava (Waked, et al., 2017). However, these procedures come with an increased risk to the patient (Hemming, et al., 2004). PDAC (Arslan, et al., 2001; Megibow, et al., 1995), neuroblastoma (Rich, et al., 2011), Kaposiform hemangioendothelioma (Kato, et al., 2012), gastrointestinal neuroendocrine tumors (Norton, et al., 2003), and metastatic squamous cell carcinoma (Lore, et al., 1981) represent some cancers that commonly display arterial involvement. Arterial resection and reconstruction represent an even greater risk and often represent a contraindication to surgery.

The work herein uses in vitro and in vivo models to investigate the use of applied hyperthermia to intra-operatively treat patients when a positive surgical margin is enountered. Applicants use PDAC as a cancer model for these studies as PDAC commonly displays involvement with major mesenteric vessels, in particular the superior mesenteric artery (SMA) (Arslan, et al., 2001; Megibow, et al., 1995). However, the method may be used for any type of solid tumors. The method for applying hyperthermia was through a novel device that may be referred to herein as the 'CorleyWare' device (CWD). The device is a resistive heating device designed to facilitate a uniform heating profile around the tumor and is based on the phenomenon of cancer cells being especially sensitive to hyperthermia (Paula, et al., 2012). A schematic overview of a specific embodiment of the device is highlighted in FIG. 16D. Furthermore, in specific embodiments this form of intra-operative hyperthermia treatment targets a dangerous subpopulation of cancer cells, namely cancer stem cells (CSCs) (Oei, et al., 2017), which are implicated in tumor resistance and recurrence. CSCs are defined as cells within a tumor that can self-renew and drive tumorigenesis. It is considered that CSCs may generate tumors through stem cell processes of self-renewal and differentiation into multiple cell types. Although some studies have shown that certain agents, such as siRNA, can somewhat reduce CSCs populations (Jaganathan, et al., 2014; Dave, et al., 2012), there are currently no approved treatments that specifically target CSCs, which contributes to slow advancements in patient outcome over the last four decades when an intravenous cytotoxic or biological agent approach has been taken.

This present example provides insight into the effects of mild hyperthermia on cancer, stromal and endothelial cells in vitro 2D monolayer settings, including CSCs renewability potential. One determines hyperthermia gradients in tumor tissue due to localized heating and subsequent intra-tumoral cellular damage because of hyperthermia in vivo murine and swine models. Finally, the results are validated with a mathematical model of hyperthermia dissipation in tumor encased SMA tissues when exposed to CWD heating.

Examples of Methods

Cell Lines

Human PDAC lines, PANC-1 and AsPc-1, cells were obtained from American Type Culture Collection (ATCC). PANC-1 and AsPc-1 cells were maintained in DMEM with 10% FBS. Human umbilical vein endothelial cells (HUVEC) (Lonza, Walkersville, MD, USA) were maintained in vascular cell basal medium supplemented with 0.2% bovine brain extract, 5 ng/mL rh EGF, 10 mM L-glutamine, 0.75 units/mL heparin sulfate, 1 µg/mL hydrocortisone hemisuccinate and 2% fetal bovine serum and 50 µg/mL ascorbic acid.

Human microvascular endothelial cells (HMVEC) (Lonza, Walkersville, MD, USA) were incubated in endothelial cell basal medium (Lonza) supplemented with endothelial cell growth medium (EGM) microvascular bullet kit containing 25 ml FCS, 0.5 ml hEGF, 0.5 ml hydrocortisone, 0.5 ml gentamicin, 0.5 ml bovine brain extract (Lonza). Cells were grown to confluence and when needed harvested with trypsin-EDTA (Lonza). All cells lines were maintained in a 95% humidified atmosphere of 5% $CO_2$ at 37° C. and 2% penicillin-streptomycin solution was added to the media of all cell lines.

In-Vitro Time-Resolved Cytotoxicity Testing

Cytotoxicity was quantified using DNA-binding DRAQ7 (Biostatus Ltd, UK) staining, which is a far-red fluorescent dye. Cells were seeded at a concentration of 100,000 cells per well in Greiner Bio One Cellstar® tissue culture 6-well plate for 24 h. Plates were then placed into a water bath and heated to the given thermal dose. An optical probe was inserted into a cell free well that contained 2 ml of media so that accurate thermometry of the plate bottom could be achieved. After 10 mins of water bath hyperthermia, 3 µM concentration of DRAQ7 was placed in the cell medium before being gently pipetted to ensure thorough mixing. High throughput microscopy was performed within 10 min of adding the DRAQ7 using the ImageXpress Micro XL microscope (GE Healthcare, USA). Images were obtained which included 10,000 cells at 0 h and 24 h time points in triplicate for statistically robust findings. Cells were imaged at 20× magnification in two wavelengths: the DRAQ7 (Cy5, Absorbance 600 nm emission 697 nm) and the bright-field wavelengths. At the end of the time-lapse experiment the cells were placed in 52° C. water for 10 minutes to induce 100% cell death before an additional set of images was collected, from which a measure of the total number of cells in each well was obtained. Cell death was quantified by the automated measure of the DRAQ7 signals at 0 h and 24 h time points using MetaXpress 5.3.0.5 and MetaXpress PowerCore 1.3.0.3 software (Molecular Devices, USA) and was displayed as a percentage of the total cells within each well.

Reverse-Phase Protein Array Assay

Reverse phase protein array (RPPA) assays were performed as described previously (Holdman, et al., 2015; Welte, et al., 2016) with minor modifications. Protein lysates were prepared from the cell culture samples with Tissue Protein Extraction Reagent (TPER; Pierce) supplemented with 450 mM NaCl and a cocktail of protease and phosphatase inhibitors (Roche Life Science). Protein lysates at 0.5 mg/ml of total protein were denatured in SDS sample buffer (Life Technologies) containing 2.5% 2-mercaptoethanol at 100° C. for 8 min. Protein lysates were arrayed onto nitrocellulose-coated slides (Grace Bio-labs, Bend, OR, USA) using an Aushon 2470 Arrayer (Aushon BioSystems, Billerica, MA, USA) with an array format of 960 (experimental and controls) lysates per slide with each sample spotted as technical triplicates (2,880 spots per slide). Slides were blocked for 1 h with I-Block reagent (Applied Biosystems) followed by a 15 min incubation with Re-Blot reagent (Dako) and were loaded on an automated slide stainer Autolink 48 (Dako, Carpinteria, CA, USA) for incubation with primary antibodies. Antibody binding was detected by fluorescence with a Vectastain-ABC Streptavidin-Biotin Complex (Vector, PK-6100) followed by incubation with the TSA-plus Biotin Amp Reagent diluted at 1:250 (Perkin Elmer, NEL749B001KT) and a 1:50 dilution of LI-COR IRDye 680 Streptavidin (Odyssey) as the detection probe. The total protein content of each spotted lysate was assessed by fluorescent staining with Sypro Ruby Protein Blot Stain for selected subsets of slides (Molecular Probes). Fluorescent-labelled slides were scanned on a GenePix AL4400 scanner, and the images were analyzed with GenePix Pro 7.0 (Molecular Devices). For normalization, raw image intensity of each spot was subtracted from that of negative controls and then divided by total protein values. Tumors with different genetic backgrounds were analyzed separately. Of the 212 validated antibodies included in the RPPA, 143 antibodies detect total protein and 69 detect specific phosphorylated states known to be markers of protein activation. The validated antibodies represent proteins in various signaling pathways and cell functional groups including growth factor receptors, cell cycle, cell proliferation, apoptosis, EMT, stem cells, DNA damage, cell stress, autophagy, cytokines, protein translation and gene transcriptional activators and repressors. For a complete list of validated antibodies see https://www.bcm.edu/centers/cancer-center/research/shared-resources/antibody-based-proteomics. Significantly differentiated antibodies between experimental groups were determined using a cutoff of $P<0.05$ (by two-sided Student's t-tests) and FC (fold change) $>1.25$ (or $<1/1.25$).

Pancreatic Cancer Stem Cells Sphere Forming Assay

Cells were seeded at a concentration of 100,000 cells per well in Greiner Bio One Cellstar® tissue culture 6-well plate for 24 h. Plates were then placed into a water bath and heated to the target thermal dose. An optical probe was inserted into a cell free well that contained 2 ml of media so that accurate thermometry of the plate bottom could be achieved. After 10 mins of water bath hyperthermia, the media was collected and the cells were trypsanised before being added to the supernatant media before spinning down and reseeding in six-well ultra-low attachment plates (Corning) with 2 ml of serum-free mammosphere medium. Fresh mammosphere medium was added to the wells every 3 days. The number of viable PDAC spheres at 14 days were imaged using ImageXpress Micro XL microscope (GE Healthcare, USA) and counted using MetaXpress 5.3.0.5 software (Molecular Devices, USA).

Scanning Electron Microscopy (SEM)

Cells were fixed by washing thrice with 0.1M sodium cacodylate buffer (CDB) followed by incubation in 2.5% glutaraldehyde for 25 min at room temperature. Next, cells were washed twice in 0.1M CDB and subjected to an ethanol series for dehydration. The cells were then incubated in 1:1 t-butanol:ethanol mixture for 5 min and mounted on carbon tape upon an SEM stub. Immediately before imaging the samples were sputter coated with 50% platinum 50% palladium at a thickness of 5.0±0.2 nm to ensure good electrical conductivity.

Generation of Orthotopic PDAC Tumors in Mice

Animal studies were performed in accordance with the guidelines of the Animal Welfare Act and the Guide for the Care and Use of Laboratory Animals based on approved protocols by Baylor College of Medicine Institutional Animal Care and Use Committee (IACUC). Mice were kept in standard housing conditions and diet with free access to water. Orthotopic pancreatic tumors were grown in 6-7 week old athymic nude (FOXn1 nu) female mice (Harlan Sprague Dawley, USA). Under sterile conditions a 1 cm incision was made in the left flank to expose the pancreas. PANC-1 cells ($1 \times 10^6$ in 40 µL of 1:1 PBS:Matrigel) were injected into the pancreas. The abdominal wound was closed in two layers. Tumors were allowed to grow for 6 weeks before being used for experimentation.

For ex vivo measurement of heating differentials and tumor damage due to hyperthermia, tumor were excised from the mice after euthanization and then exposed to various thermal doses with optical temperature probes place on their surface and within their core before immediate fixation in 4% formaldehyde for histology preparation.

The measurement of in vivo heat differential and tumor damage due to hypethermia involved non-survival surgery where under anesthesia the tumor was gently removed from the abdomen of the mouse before probes were positioned on the tumor surface and into the core of the tumor. Hyperthermia involving various target thermal doses was then administered. After the treatment, the peritoneum and skin layers were gently closed and the mouse was kept sedated for two hours under anesthesia before being euthanized. The tumor was then excised and immediately fixed in 4% formaldehyde for histology preparation.

Large Animal Models

Female Yucatan miniature swine (Sinclair Bioresources; Auxvasse, MO) were housed and raised according to Institutional Animal Care and Use Committee (IACUC) guidelines at the Baylor College of Medicine. No special diet was given. At the time of Corleyware testing, pigs were 12 months of age and weighed 70-75 kg.

For femoral artery heat differential measurements, a Yucatan miniature swine was sedated and anesthetized without complications for non-survival surgery. Their femoral artery was exposed for the delivery of a localized thermal treatment. All animals were stable throughout the procedure.

For survival surgery when investigating any delayed onset of pathology associated with hyperthermia administration to the SMA, a female Yucatan swine was sedated and anesthetized without complications. The SMA was exposed and further skeletonized before being given a localized thermal dose of 41° C. for 10 mins. Pain medications (75 mcg/hr fentanyl patch and 0.4 mg/kg Meloxicam SQ) and perioperative antibiotics were provided (1 gram Cefazolin IV). The animal stable throughout the procedure with 1300 mL of IV LRS administered. A local anesthetic (5 mL lidocaine, 5 mL bupivacaine and 5 mL saline) was injected after closure. The swine was euthanized 48 h after the procedure, where a gross pathological assessment and a subsequent histological assessment of relevant tissues were performed.

Immunohistochemical Evaluation

Tissue samples were fixed in formalin and processed in paraffin blocks and sectioned using standard techniques. Tissue slides were stained with H&E, Verhoeff-Van Gieson (Elastic fibers) and Cleaved PARP (apoptosis). Histology slides were imaged using Nikon Eclipse TE2000-U microscope fitted with a Nikon digital sight DS-Fi1 video camera. All slides were imaged at a fixed 167 ms exposure time.

Computer Simulation of CWD

Simple simulations of the Corleyware device were performed using the software Sim4Life (ZMT Zurich MedTech AG, Zurich, Switzerland) (Maiques, et al., 2014). The model for all simulations consisted of a cylindrical blood vessel (inner diameter 4.5-7 mm, with 1 mm vessel walls), partially enclosed by a cylindrical section of pancreatic tissue of thickness 1-10 mm. The Pennes Bioheat Transfer Equation[29] was used for all simulations:

$$ps\frac{\partial T}{\partial t} = \nabla \cdot k \nabla T - p_{bl}s_{bl}w_{bl}(T - T_{bl}) + Q_m$$

Where T is the temperature of the tissue of interest, t is time, P is the density, s is the specific heat, k is the thermal conductivity, and $Q_m$ is the rate of metabolic heat production for a specific tissue type. The constants $\rho_{bl}$, $s_{bl}$ and $w_{bl}$ are the density, specific heat and perfusion rate of blood through the tissue, and $T_{bl}$ is the temperature of blood. Note that the electric field heating term of the Pennes equation was omitted since it was not needed in this case. Values for all physical constants were taken from the IT'IS Database for Thermal and Electromagnetic Parameters of Biological Tissues (Hasgall, et al., 2015). For all simulations, blood temperature was fixed at 37° C. and the background temperature was set to 25° C.

Flow of blood through the SMA was not explicitly modeled. Instead, blood flow was treated as constant, not pulsed, flow by the blood flow term of the Pennes equation ($\rho_{bl}s_{bl}w_{bl}(T-T_{bl})$). The Pennes equation was also used for non-biological materials. If the blood perfusion and metabolic terms are set to zero, the Pennes equation is reduced to the three-dimensional heat equation (Crank, et al., 1947). Heating of the Corleyware device was achieved by using a non-zero rate of metabolic heat production ($Q_m$), where the value of $Q_m$ was chosen to produce the desired temperature.

Examples of Results and Significance Thereof

One embodiment for the use of CWD is to heat the tumor that remains after positive-margin resection on the SMA during PDAC surgery. Cancer cells have an increased susceptibility to heat when compared to normal cells, which is supported by the data presented in FIGS. 12A-12G. It shows high susceptibility and drastic morphological alterations of cancer cells when exposed to various temperatures (37-46° C.). Non-malignant cell lines, such as endothelial cells, display less drastic responses. Furthermore, in specific embodiments the arterial blood flow is advantageous in providing a heat sink to dissipate heat away from the inside lumen of the artery and will therefore act as a protective mechanism for the artery when undergoing treatment with the CWD.

The Effect of Hyperthermia on PDAC and Endothelial Cells

In-vitro investigation was carried out to establish an approximate thermal dose that eliminated PDAC cell lines while minimizing the effects on healthy tissues. In specific embodiments, the device will operate within an optimal thermal dose, in particular embodiments, where there is sufficient hyperthermia to enable tumor destruction while simultaneously limiting damage to healthy vascular tissue, as local thrombosis may occur leading to ischemia in the tissues downstream of the SMA and cause major complications in the patient. At the same time, weakening of the arterial wall can cause pseudoaneurysmal dilation and rupture, an equally catastrophic outcome. Initial in-vitro studies allow the determination of thermal doses needed for application of a device of the disclosure. The percentage cell death induced by thermal doses of 42° C., 44° C. and 46° C. for 10 minutes after an initial thermal increase from 35° C. which took 5 minutes were investigated (FIGS. 3A-3F).

Figure 3A:
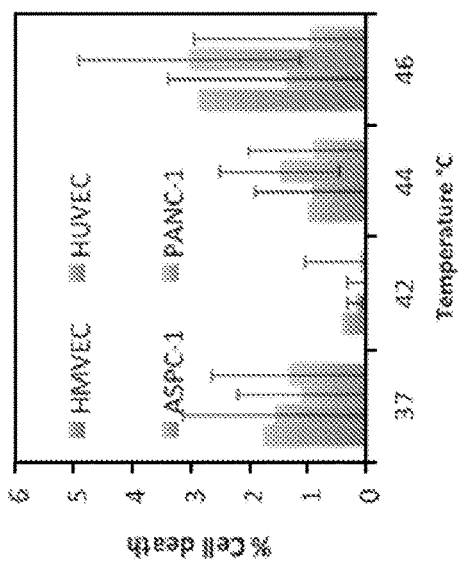
FIGS. 3A-3F depict heating and cell viability.
Figure 3B:
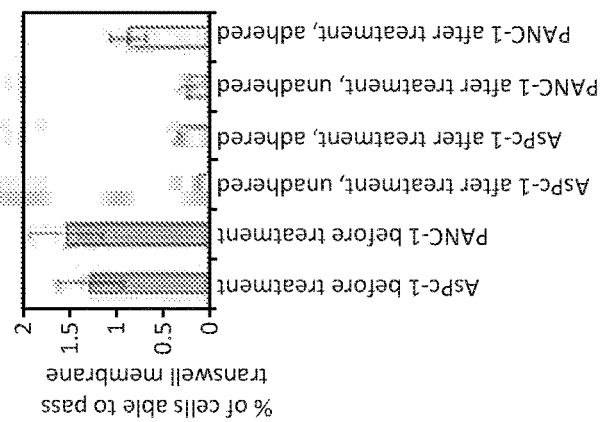
Figure 3C:
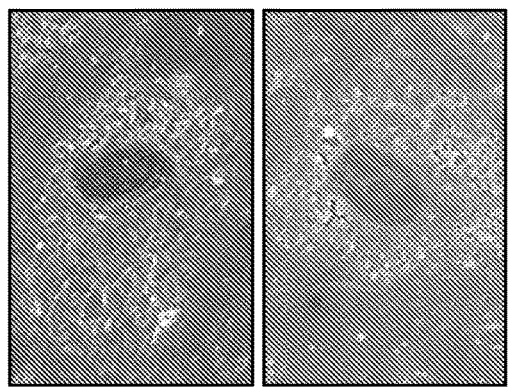
Figure 3D:
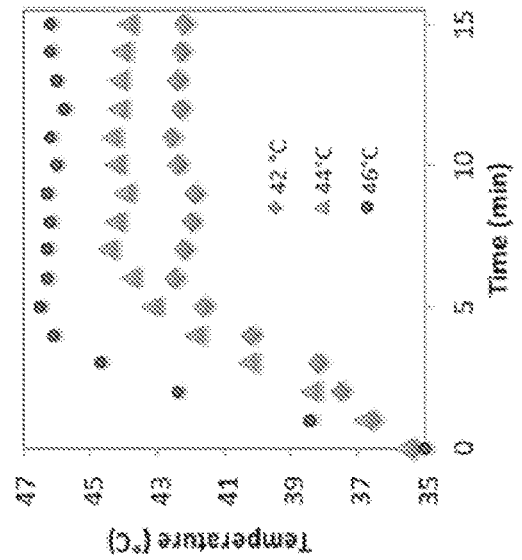
Figure 3E:
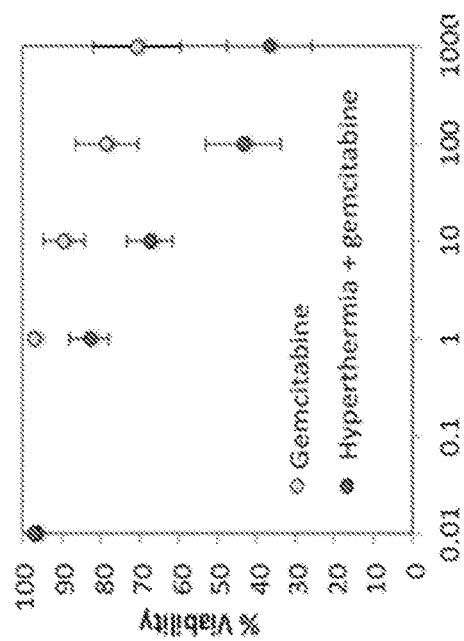
Figure 3F:
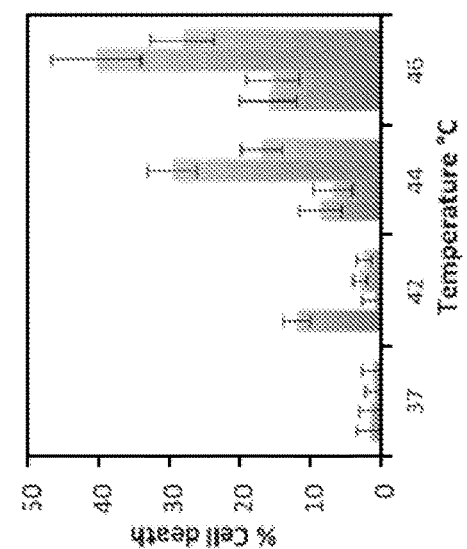

The benefit of in-vitro population-wide high throughput cytotoxicity studies have previously been described (Ware, et al., 2014). This analysis was performed using numerous relevant cell lines to the PDAC-SMA environment and indicated that a thermal dose of 44-46° C. for 10 min (as merely an example) would induce the greatest cytotoxicity in cancer cell lines while minimizing the effects seen in normal vascular endothelial cell lines (FIG. 3B-3D). Other hyperthermia effects on PDAC cells, such as cytoplasmic retraction and alterations in cell metabolism have also previously been reported (Ware, et al., 2015). Importantly, Applicants have found that hyperthermia pretreatment means an increase in susceptibility of cancer cells to chemotherapy (FIG. 3E). This is a clinically relevant finding, as intraoperative hyperthermia administration via the device induces the positive margin left after surgery to be more chemo-sensitive in later patient chemotherapy regimens, in particular embodiments. Although these studies approximate the true biological environment, which includes arterial blood flow and the extra-cellular environment, they provide insight into the thermal dose required for greatest differential in cell death between malignant and healthy cells.

In addition to the treatment of the bulk of the tumor remaining after surgery, Applicants consider that hyperthermia administered to PDAC cells encompassing the outer surface of the SMA will target specific cell populations that are particularly relevant to tumor drug resistance and regrowth, which include CSCs. Water bath heating of several cancer cell lines destroyed the viability and renewability of CSCs within these cancer cell populations (FIGS. 11A-11E). The tumor sphere formation assay is a functional test that assesses the self-renewal potential of untreated and treated CSCs and is seen as a measure of the number of viable CSCs residing in a cancer cell population. Sphere formation 14-days after heat treatment was quantified to rule out the possibility of heat-treated CSCs remaining dormant for a length of time, only to develop at a later date, which prompts recurrence of a tumor. FIGS. 11A-11E show that a single heat treatment eliminates (>95%) of CSCs in PDAC cell populations, as it abolished the tumor sphere forming ability of the treated cells in-vitro. This effect was present in a wide range of different PDAC cell lines; AsPc-1, PANC-1, and MIA-PaCa-2. Although responses observed were thermal dose dependent, effects were observed even at the lowest thermal doses.

All PDAC cell lines showed a complete disruption of CSC viability when given a thermal dose of 46° C. for 10 minutes (FIGS. 11A-11E). This indicates that collateral thermal damage to healthy tissues during heat treatment can be minimized as 46° C. for 10 minutes is not classed as ablation which causes inflammation and damage to healthy tissues surrounding the diseased loci.

Figures 16A, 16B:
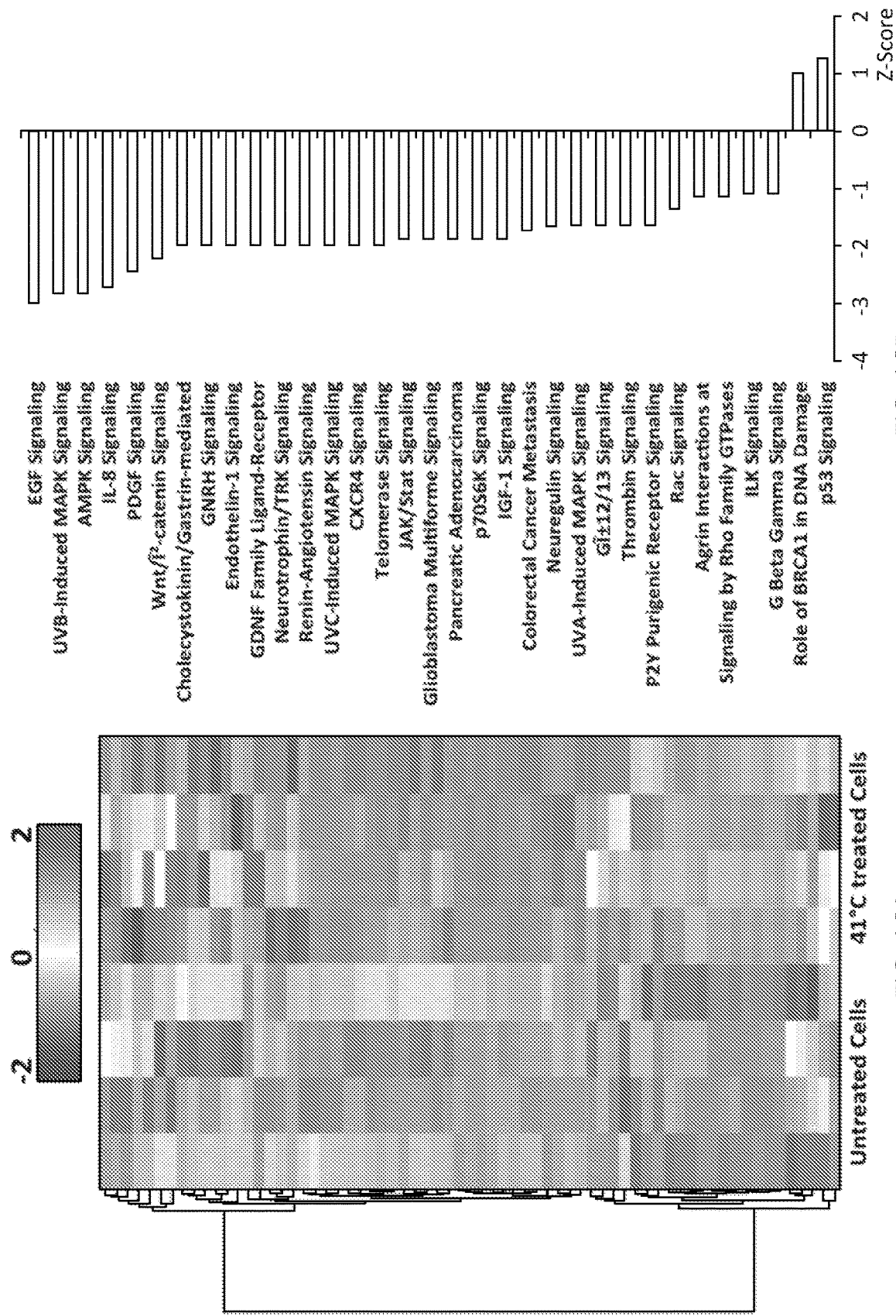
FIGS. 16A-16B show proteomic analysis of pancreatic cells exposed to mild hyperthermia (41° C. for 10 mins).

Applicants further investigated the effects of hyperthermia on PDAC cells by exploring the changes in protein expression induced by mild hyperthermia (41° C. for 10 mins) via the reverse-phase protein array (RPPA). The antibody panel used for the RPPA included 212 proteins covering major cellular signaling pathways involved in numerous aspects of cancer development and progression. The Student's t-test was used to identify significantly differentiated levels of total or phosphoproteins with p-value <0.05 and fold-change >1.25 (or <1/1.25). Mild hyperthermia induced the expression of 23 up-regulated proteins and 44 down-regulated proteins when compared to untreated cells (FIGS. 16A and 16B, Table 1). Further analysis using Ingenuity pathways analysis identified several significantly (Z-score >1 or <−1) associated canonical pathways, most of which were down-regulated after hyperthermia treatment (FIG. 16B).

TABLE 1

List of altered genes when PDAC cells were exposed to 41° C. for 10 mins

| Altered genes after 41° C. hyperthermia Gene Symbol | Relative effect (Fold change, + denotes up-regulation and − denotes down regulation) | p-value |
| --- | --- | --- |
| RRM2 | +2.35 | 9.90E−09 |
| Integrin b3 | +2.06 | 5.18E−04 |
| Hexokinase II | +1.67 | 7.09E−07 |
| p-Rb | +1.34 | 2.57E−07 |
| Laminin 5 | +1.28 | 2.53E−07 |
| Slug | +1.15 | 4.53E−08 |
| Vimentin | +0.99 | 8.53E−05 |
| 14-3-3zeta, gamma, eta | +0.85 | 3.25E−03 |
| AuroraA/AIK | +0.84 | 9.66E−07 |
| DKK1 | +0.72 | 8.04E−04 |
| FGFR1 | +0.69 | 1.91E−06 |
| BRCA1 | +0.66 | 3.63E−05 |
| Integrin a5 | +0.63 | 3.88E−04 |
| GSK-3a/b | +0.54 | 2.89E−03 |
| Integrin b4 | +0.47 | 2.11E−05 |
| Caveolin-1 | +0.47 | 1.27E−05 |
| Claudin-1 | +0.41 | 2.27E−04 |
| p-Stat2 | +0.38 | 2.99E−02 |
| LC3A | +0.38 | 3.92E−03 |
| BRCA 2 | +0.38 | 2.23E−03 |
| Ki67 | +0.37 | 6.10E−03 |
| CHAF1A | +0.35 | 5.90E−05 |
| Annexin1 | +0.33 | 5.31E−03 |
| p-Aurora A | −0.33 | 2.07E−03 |
| Zeb1 | −0.34 | 1.69E−02 |
| p70S6K | −0.34 | 2.36E−02 |
| p-EGFR | −0.34 | 3.95E−03 |
| Bak | −0.35 | 6.59E−03 |
| PR | −0.37 | 1.04E−02 |
| PI3Kp110a | −0.38 | 4.58E−03 |
| p-AMPKb1 | −0.39 | 1.79E−04 |
| AMPKa | −0.39 | 2.90E−03 |
| Caspase-3 | −0.4 | 2.01E−03 |
| p-Tuberin/TSC2 | −0.4 | 8.75E−04 |
| p-ALK | −0.43 | 3.95E−04 |
| Bcl-xL | −0.43 | 3.19E−04 |
| FoxK2 | −0.44 | 1.46E−06 |

TABLE 1-continued

List of altered genes when PDAC cells were exposed to 41° C. for 10 mins

| Altered genes after 41° C. hyperthermia Gene Symbol | Relative effect (Fold change, + denotes up-regulation and − denotes down regulation) | p-value |
|---|---|---|
| HER2/c-ErbB2-P185 | −0.46 | 3.84E−02 |
| FSP1/S100A4 | −0.49 | 2.58E−05 |
| p-PTEN | −0.5 | 1.18E−04 |
| p-AMPKa1 | −0.5 | 3.28E−03 |
| ILK1 | −0.51 | 5.82E−04 |
| MED12-Abcam | −0.51 | 1.20E−04 |
| p-EGFR | −0.51 | 3.68E−04 |
| p-p70S6K | −0.56 | 9.82E−06 |
| p-Beta-Catenin | −0.56 | 2.74E−06 |
| PTEN | −0.59 | 9.49E−05 |
| mTOR | −0.63 | 4.88E−04 |
| Stat1 | −0.64 | 4.18E−05 |
| HER2/c-ErbB2 | −0.65 | 6.77E−04 |
| p-AMPKa | −0.67 | 1.73E−06 |
| HER3/ErbB3 | −0.67 | 1.28E−04 |
| Caspase-7 | −0.72 | 1.04E−03 |
| p-c-Fos | −0.77 | 3.75E−07 |
| p-p70S6K | −0.79 | 3.57E−05 |
| LRP6 | −0.8 | 4.49E−05 |
| p21 | −0.86 | 1.39E−05 |
| p-c-Jun | −0.89 | 7.08E−05 |
| p-mTOR | −0.94 | 5.70E−09 |
| E-Cadherin | −0.97 | 1.84E−04 |
| Bad | −1.15 | 1.75E−07 |
| p-Akt | −1.17 | 7.07E−05 |
| p-Bad | −1.75 | 1.08E−07 |
| c-Jun | −1.87 | 8.88E−08 |
| HIF-2A | −2.08 | 5.49E−04 |
| p-p44/42MAPK | −2.48 | 1.60E−07 |
| c-Fos | −2.57 | 1.08E−08 |

Examples of hyperthermia-altered proteins are listed in Table 1. Briefly, canonical pathway analysis, which correlates altered protein expression with specific pathways and disease states and bio-functionality highlighted many signaling pathways altered in hyperthermia treated cells (FIG. 16B). Specifically, the most significant down-regulated pathways were pathways related to epidermal growth factor receptor (EGF), mitogen-activated protein kinase (MAPK), adenosine monophosphate-activated protein kinase (AMPK) and interleukin-8 (IL-8) signaling. The EGFR belongs to the ErbB group of receptor tyrosine kinases and previous studies have shown that it is involved in the pathogenesis and progression of various types of carcinoma (Normanno, et al., 2006). The MAPK pathways are activated by various intra- and extra-cellular stimuli, such as cytokines, hormones, and cellular stressors such as endoplasmic reticulum stress and oxidative stress. MAPK pathways control a variety of cellular functions that include proliferation, differentiation, survival, and cell death. Deviation from the precise regulation of MAPK signaling pathways has been shown to play a role in the progression of various cancers (Kim, et al., 2010) and has been associated in immune evasion (Sumimoto, et al., 2006) of melanoma cells. AMPK is a key energy sensor which is activated by increases in adenosine monophosphate (AMP)/adenosine triphosphate (ATP) ratio and/or adenosine diphosphate (ADP)/ATP ratio, and increases various metabolic pathways including mitochondrial biogenesis, fatty acid oxidation and glucose transport (Zhou, et al., 2017). The activation of AMPK-autophagy pathway plays a role in drug resistance in colorectal cancer (Zhou, et al., 2017). IL-8 is a chemoattractant cytokine produced by various tissues (Bickel, et al., 1993) and its up-regulation is implicated in pancreatic cancer invasion and metastasis (Wang, et al., 2017). p53 signaling was shown to be the most significantly up-regulated canonical pathway. The p53 homolog is crucial in multicellular organisms, where it prevents cancer formation, thus, functions as a tumor suppressor (Surget, et al., 2013).

To summarize, the in vitro data determines that a more mild hyperthermia, in the range of 46° C. in for 10 minutes (as an example) is sufficient to cause cancer cell cytotoxicity, induce alterations in protein expression associated in various signaling pathways in PDAC cells and destroys CSC renewability potential.

In Vivo Hyperthermia Differential

Investigation into the heating kinetics of PDAC and vascular tissue provided valuable information to enable optimal thermal dose administration to the cancer layer whilst simultaneously minimizing unwanted damage to the intima and lumen of the SMA. CWD testing on ex-vivo and deceased in-situ porcine models determined the heat differential in 'dry' tissue, where blood flow is removed as a variable.

The porcine aorta was used in the ex-vivo experiments as it represents a good comparison to the human SMA due to a more consistent size. Without blood flow present, which is expected to increase the heat differential between outside surface and lumen of artery even further, there is a constant differential of approximately 2° C. (FIG. 7) which is primarily due to the wall of the aorta.

In addition to a healthy aorta, Applicants investigated the heat differential through an orthotopic murine PDAC tumor sample. The positive margin involved with the SMA will undoubtedly deviate from patient to patient, however we choose to investigate the heat differential across a 2 mm distance, as 2 mm represents a fairly realistic positive margin after surgery. An optical probe was place on the tumor boundary (FIG. 5A) and another approximately 2 mm inside an ex vivo mouse orthotopic PDAC tumor (FIG. 5B).

Figure 17A:
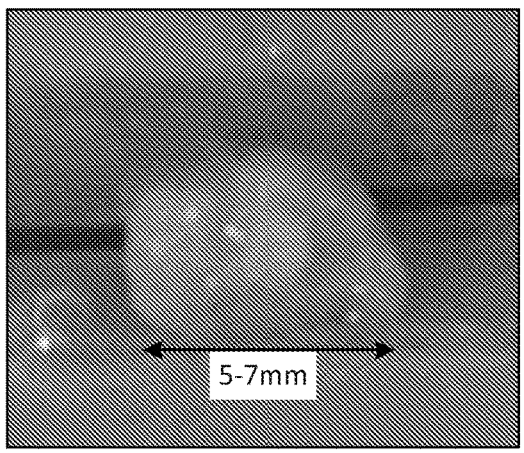
FIGS. 17A-17F depict heating differential of device and pancreatic tumor ex-vivo.
Figure 17B:
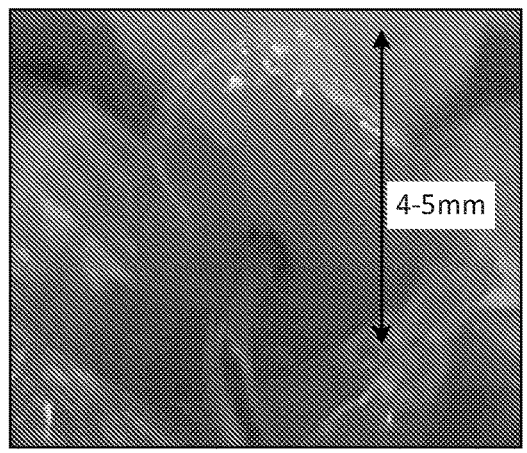
Figure 17C:
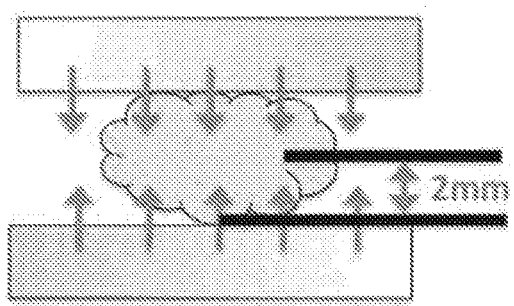
Figure 17D:
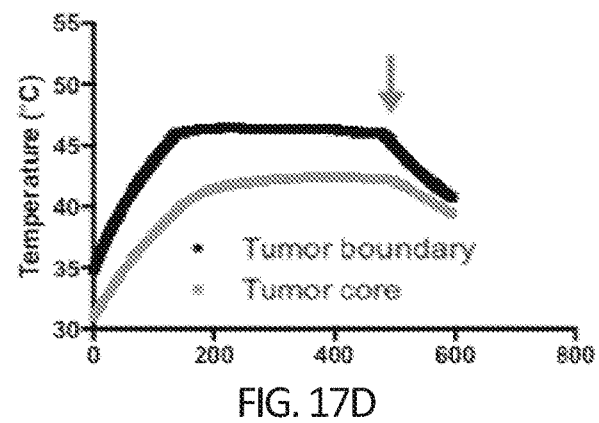
Figure 17E:
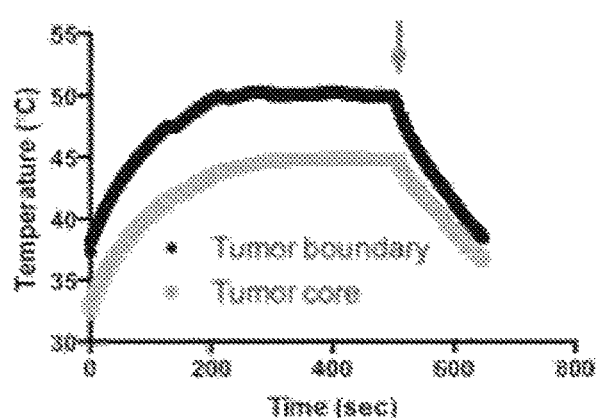
Figure 17F:
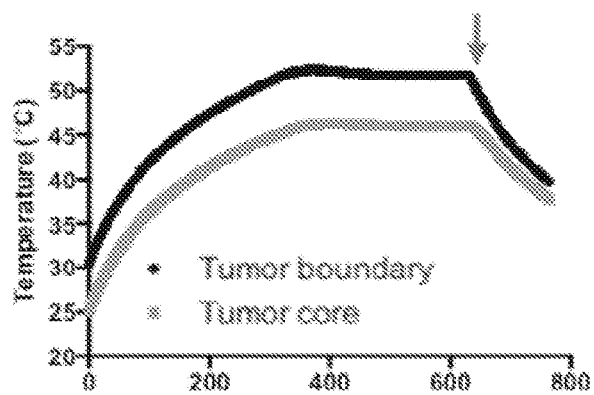
Figure 18A:
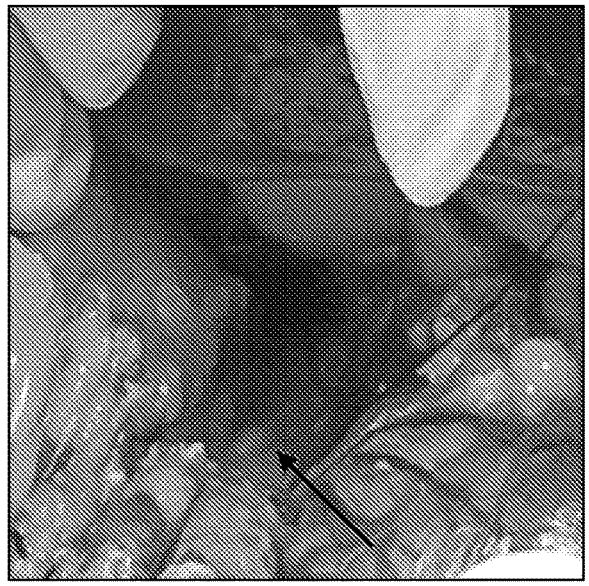
FIGS. 18A-18D depict placement of the device (device design for tight anatomical positions shown in figure), gross evaluation of tissues after surgery (FIG. 18A) in a swine. The exposed SMA prior to hyperthermia treatment (FIG. 18B) the CWD placed around SMA during hyperthermia treatment (FIG. 18C) the SMA post treatment (Yellow arrows indicate position of SMA) that shows no signs of pathology, (FIG. 18D) the small intestine immediately after treatment, which shows normal blood flow and no signs of pathology.
Figure 18B:
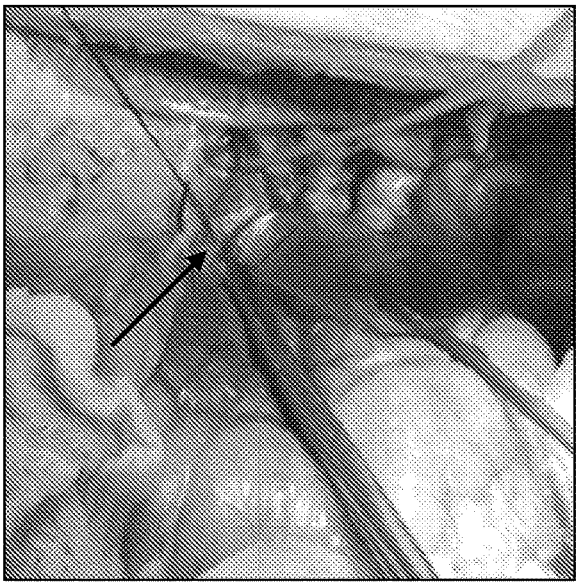
Figure 18C:
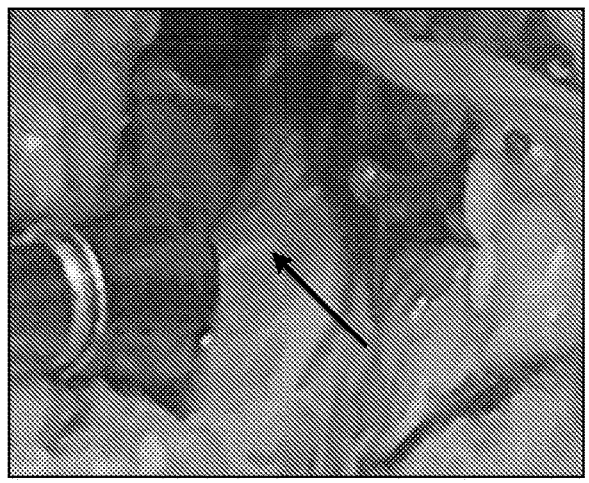
Figure 18D:
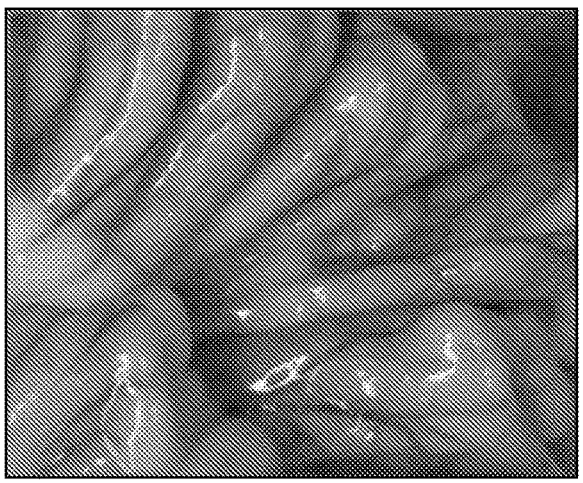
Figure 19A:
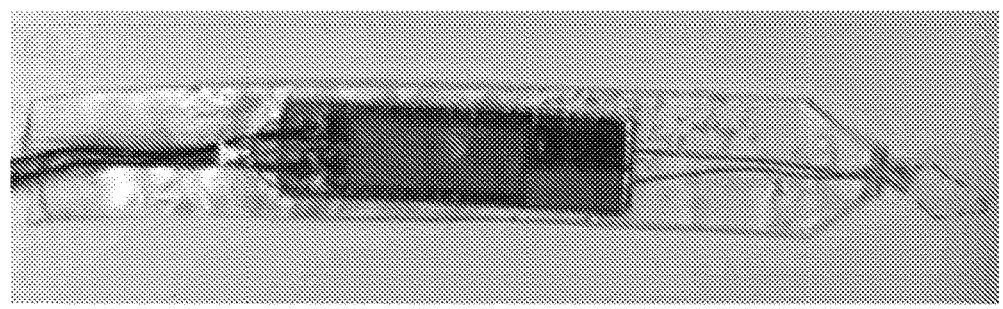
FIGS. 19A-19G.
Figure 19B:
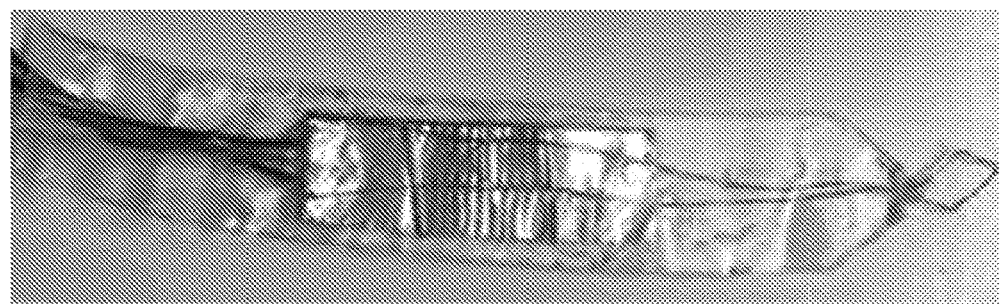
Figure 19C:
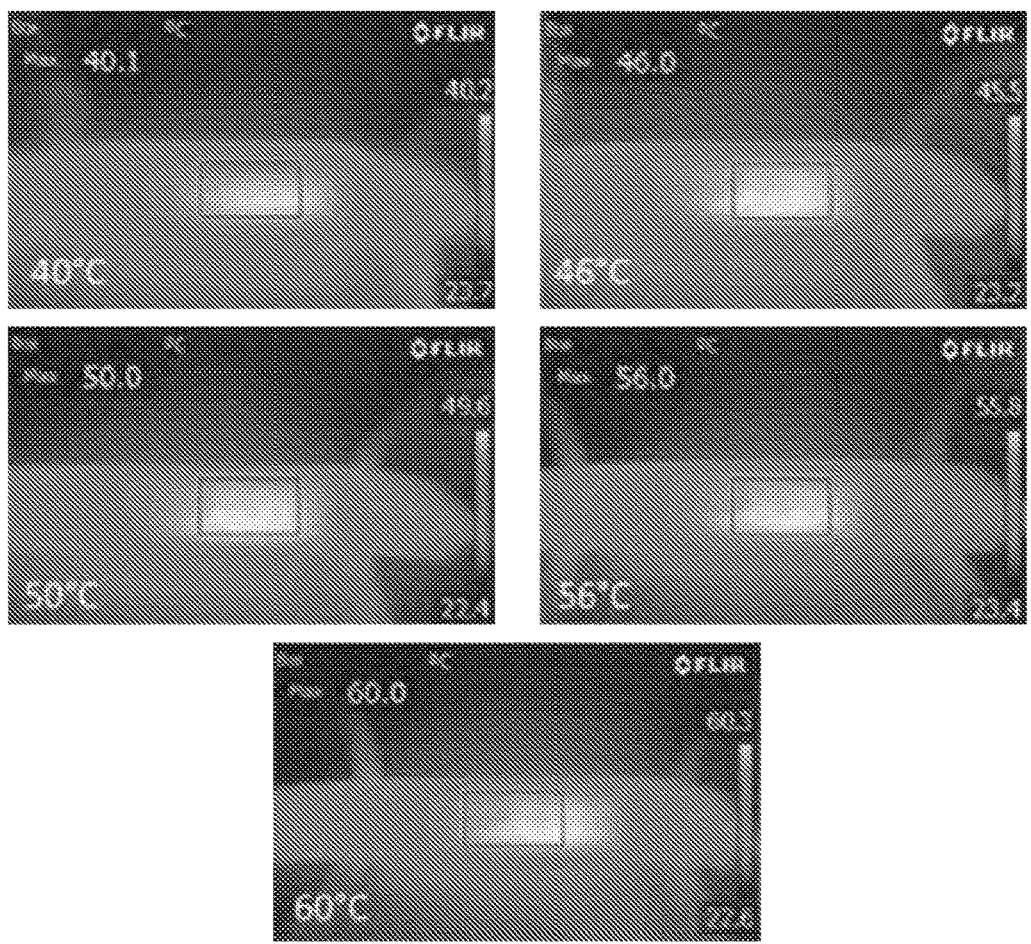
Figure 19D:
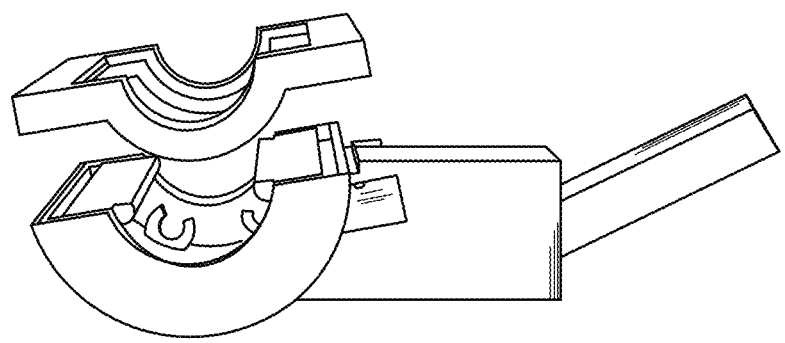
Figure 19E:
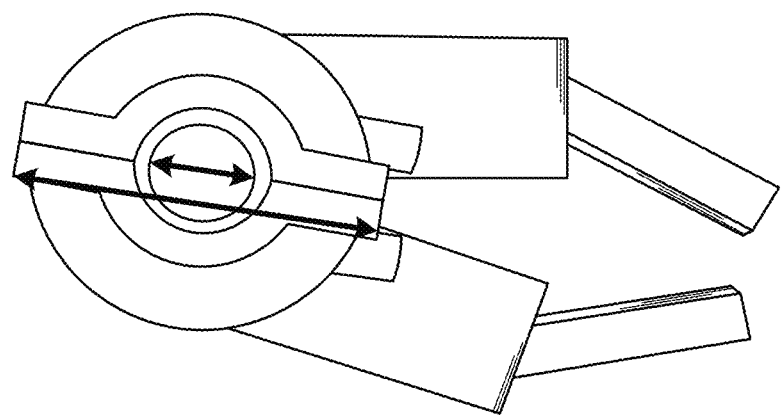
Figure 19F:
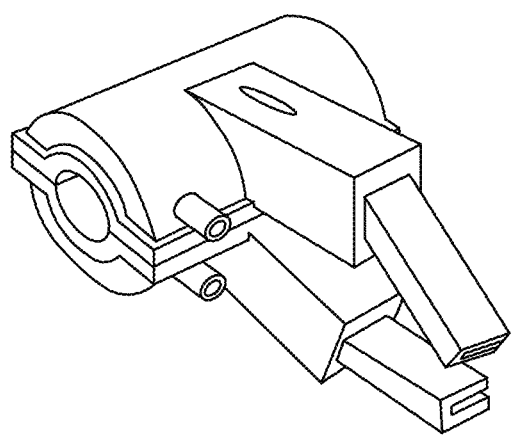
Figure 19G:
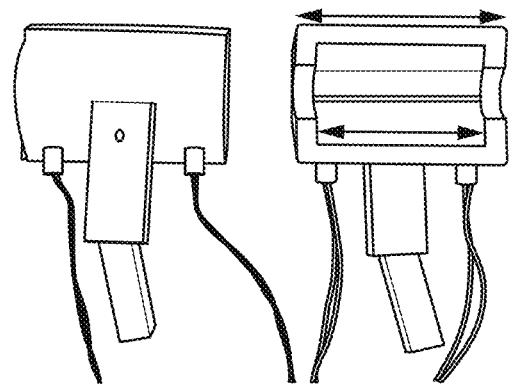

The quantification of heat differentials through artery and PDAC tumor tissue is useful for optimizing the thermal dose needed to destroy cancer cells throughout a 2-4 mm PDAC tumor positive margin while preserving the endothelium and smooth muscle found in the underlying artery. Failure to give an adequate thermal dose will mean low efficacy of the treatment whilst a thermal dose which is too high will cause damage to arterial tissues and could result in downstream ischemia in the gut or blood clotting, which are both dangerous to the patient and can be fatal. FIGS. 17D-17F indicates the temperatures 2 mm inside an orthotopically grown PDAC tumor when the tumor-CWD boundary is heated to various temperatures. In specific cases, a tumor-CWD boundary of 52° C. is necessary to achieve the proposed temperature gradient of at least 46° C. through a 2 mm thick tumor tissue.

Figure 12A:
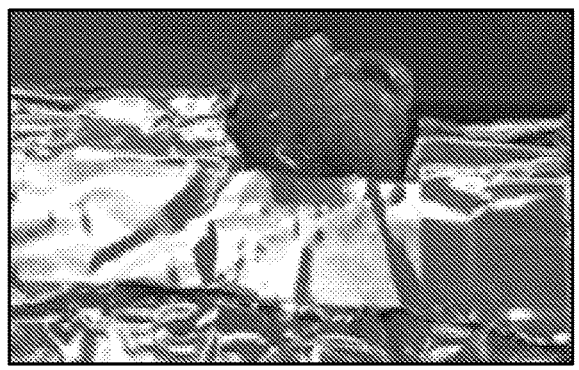
Figure 12B:
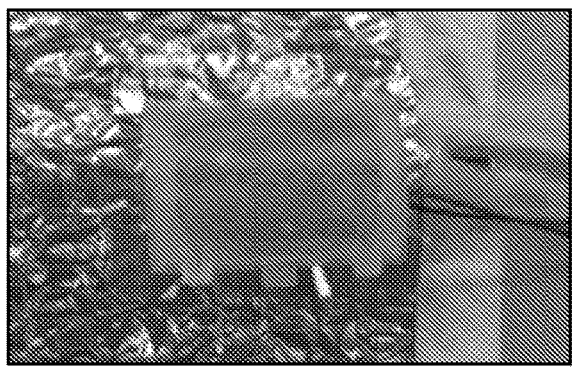
Figure 12C:
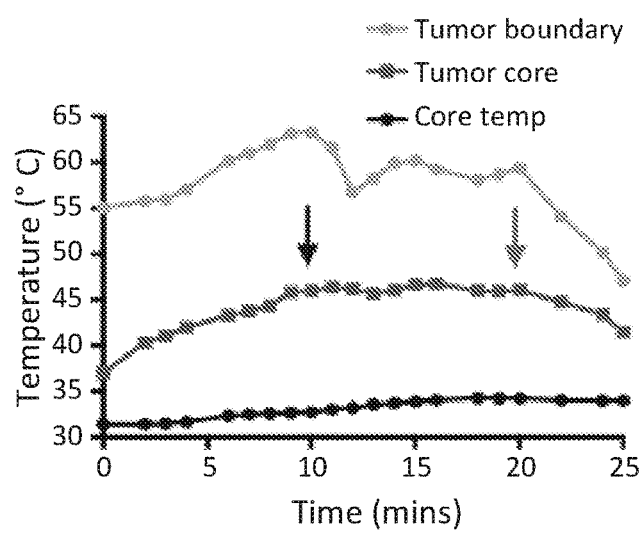
Figure 12D:
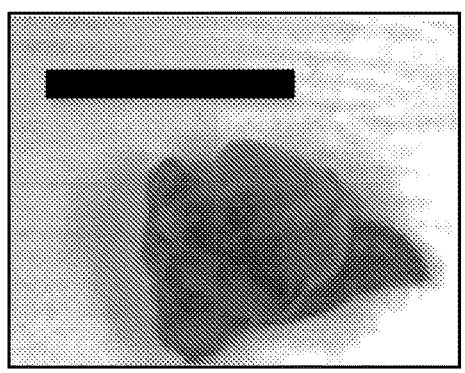
Figure 12E:
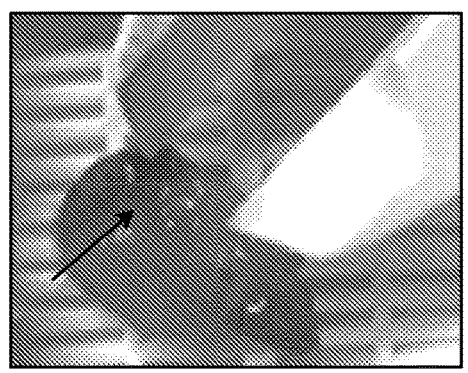

The heat differential in PDAC in a live mouse was investigated where blood flow was present within the PDAC tumor (FIGS. 12A-12G). Once again, an optical temperature probe was placed on the surface of the tumor and inserted a second probe approximately 2 mm intra-tumorally. A rectal probe was also placed to record body core temperature to ensure the mouse was not subject to total body hyperthermia. As expected, the heat differential was increased (between 10-15° C.) when compared to the ex vivo tumor sample. The differentials seen here are substantial considering the tumor in this experiment is only fed by disorganized and small tortuous tumor vessels in a small animal model. Clinically, these differentials are underestimations when compared to the tumor under hyperthermia in PDAC human patients as the tumor tissue in the clinical setting will be proximal to a much higher blood flow from the SMA that is approximately 7 mm in diameter. Nevertheless, histological analysis of various tumor samples revealed excessive cell death between the border of the treated tumor and 2 mm inside the tumor as indicated by Cl-PARP histology staining (FIGS. 12F, 12G). Collagenous extra cellular proteins, as indicated by picro sirius staining, did not show any significant alteration.

Effect of the Blood Heat Sink on Heating Dynamics

Figure 13A:
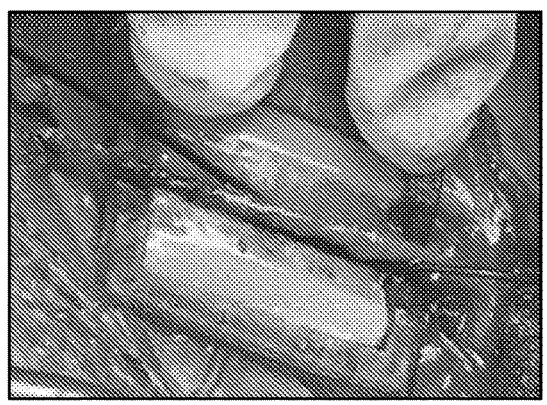
FIGS. 13A-13E depict the effect of the blood heat sink on device heating dynamics in the femoral artery in-vivo using a device which is 3 cm in length (6 cm device results are shown in FIGS. 10A and 10B).
Figure 13B:
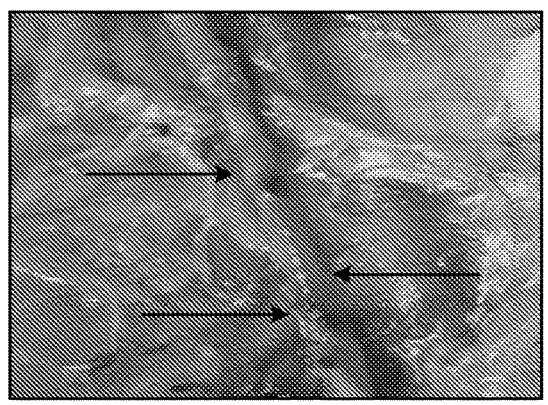
Figure 13C:
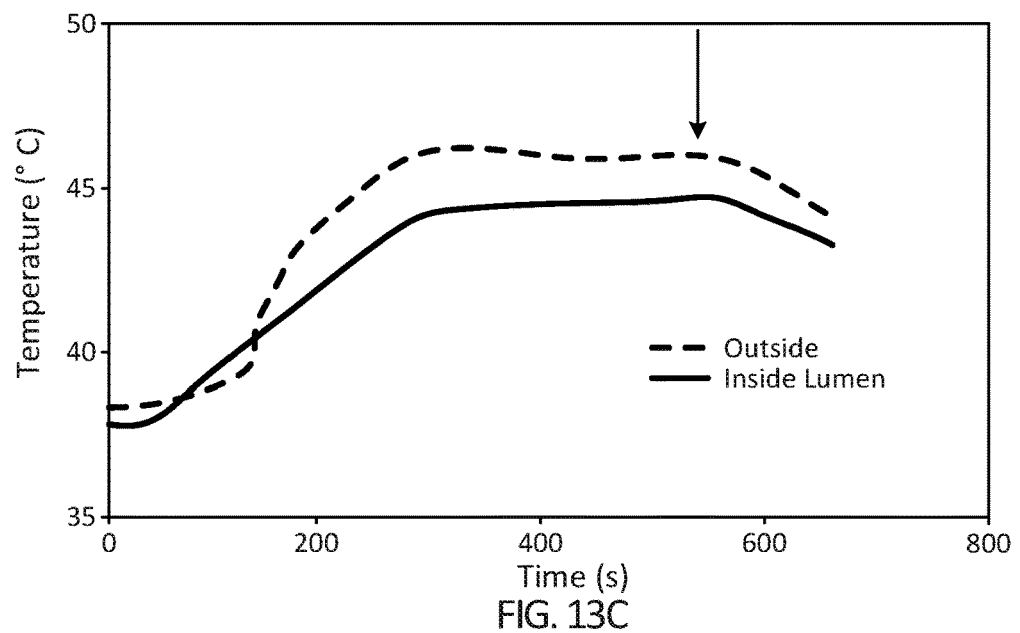

Experiments regarding testing heating dynamics of the CWD-SMA system until now have been performed in ex-vivo SMA samples, in deceased in-situ porcine models or in in vivo murine models which do not recapitulate the heavy pulsatile blood flow that would be present in human patients. A shortcoming of current various heating techniques in cancer therapy devices, such as radiofrequency ablation, is the limited performance adjacent to large blood vessels (diameter >3 mm). When the heating occurs near large vessels, the blood flow dissipates thermal energy away from the target tissue (Tungjitkusolmun, et al., 2002). This is a heat sink effect that can change both the shape and maximum volume that can be treated. In fact, the distance of the blood vessels from the tumor determines the location of the maximal tissue temperature. As a result, tumors in the vicinities of large vessels are associated with high recurrence rates from incomplete thermal desctruction (Lu, et al., 2002). In specific embodiments, one can mitigate these challenges by investigating the heating dynamics with specific consideration of blood flow characteristics along with the size of the patient and their SMA, and the thickness of the remaining positive margin enables a powerful tool to achieve insight into the heat dynamics within a given system. These details, in theory, will enable the surgeon to tune the CWD temperature to personalize the thermal dose given to a particular patient. However, in specific embodiments blood flow through the SMA lumen will be advantageous in this instance as it will increase heat differential between outside cancer layer and inside healthy vasculature. The heating dynamics of the CWD were investigated when placed around the femoral artery (FA) in a live swine model to perform CWD testing when a high pulsatile blood flow is present and obtain temperature profiles of vessel interfaces as a function of time (FIG. 13). The FA was chosen for testing, as it is superficial for easier surgical access and also similar in size to the SMA in humans and is intended to provide proof of principle regarding the blood flow heat sink effect. An optic temperature probe was secured onto the outside surface of the artery, and a second probe was inserted into the lumen of the artery before the CWD was placed around the artery (FIG. 13A) and current was passed through the device to produce a localized thermal dose. This test confirmed the CWD could be accurately fitted to a vessel without major occlusion, which is particularly relevant because SMA occlusion can result in a downstream ischemic insult in the intestine (Ypsilantis, et al., 2015). The differential between the inside lumen and outside surface of the FA (artery wall is approximately 0.5-1 mm thick) when blood is flowing is ~1.5-2° C. when outside surface was heated to 46° C. (FIG. 13C). The vessel after heating showed minimal signs of thermal damage (FIG. 13B).

Figure 13D:
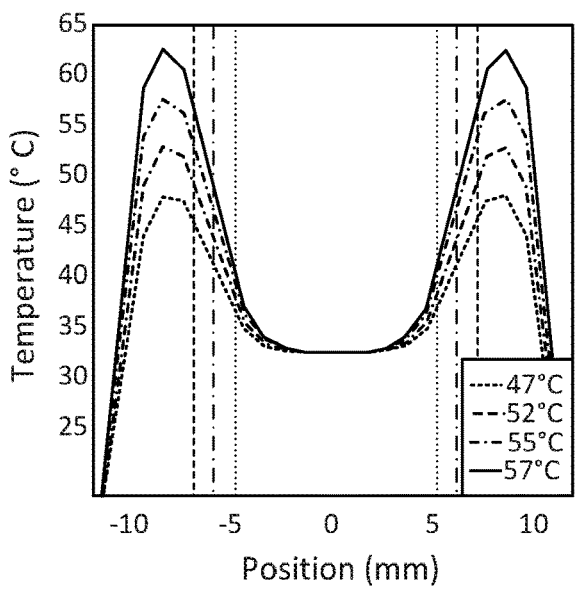
Figure 13E:
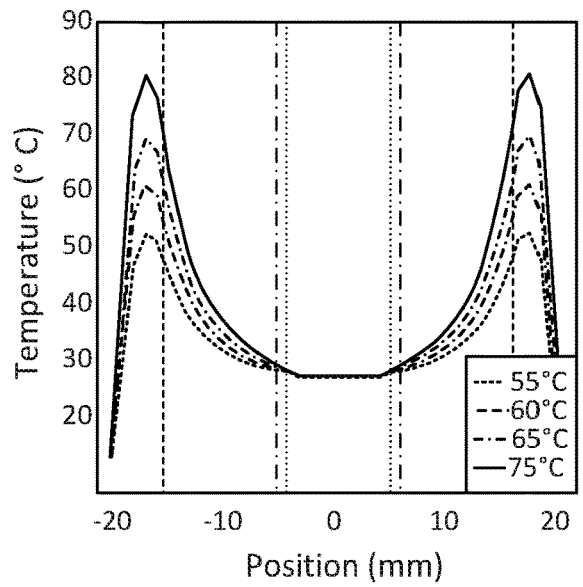

To complement the experimental findings, Applicants developed a simple simulation to provide some information of the heating differentials seen through the whole tumor-vessel system (FIGS. 13D, 13E). This simple simulation of the CWD utilized the Pennes bioheat transfer equation (Molina, et al., 2017) and used Sim4Life software (Pawlik, et al., 2005). The model for all simulations consisted of a cylindrical blood vessel (inner diameter 10 mm, with 1 mm vessel walls), partially enclosed by a cylindrical section of pancreatic tumor tissue of thickness between 1-10 mm. One embodiment was to heat the full thickness of the tumor tissue to at least 46° C. while limiting the temperature at the artery interface. The simulation displayed large thermal differentials even through small thicknesses of tissues. For instance, to achieve a temperature of at least 46° C. with a tumor tissue layer of only 1 mm, a device embodiment would have to heat the tumor boundary to at least 52° C. (FIG. 13D). For a 10 mm tumor layer, one device tumor boundary temperatures in excess of 80° C. only achieved 46° C. through half of the tumor tissue (FIG. 13E).

Figure 14A:
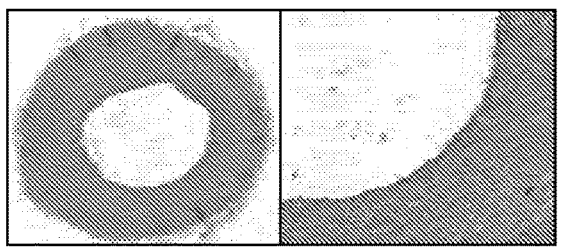
FIGS. 14A-14E depict femoral artery pathology after device treatment. Planar view of a femoral artery with corresponding zoomed in view of the endothelium (right).
Figure 14B:
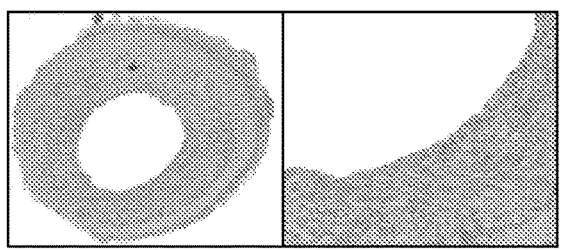
Figure 14C:
Figures 14D, 14E:
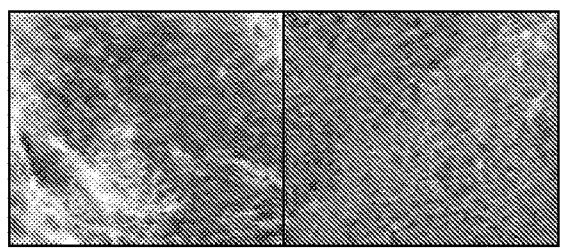

One embodiment of at least one of the devices is to deliver a thermal dose intra-operatively to the outside tumor layer that is sufficient enough to destroy cancer cells and to delay or eliminate recurrence of the tumor. It is useful that at the same time the prevention of significant damage to the underlying artery is achieved and hence the function of downstream tissues and organs can be maintained. Additionally, thrombosis or weakening of the heated artery needs to be avoided. The arterial viability following hyperthermia treatment was evaluated by histology following the excision of the FA straight after treatment. FIGS. 14A, 14B and 14C show a planar view of an untreated, a device-treated FA and a FA that has undergone extensive heating, respectively, (55° C. for 10 mins) to act as a positive control. No obvious pathological features exist in the tunica intima, media or adventitia immediately after device treatment at this thermal dose. Alternatively, the positive control shows a ruffled endothelium and shrinkage in the width of the tunica media. SEM imaging performed on the tunica intima layer of the vessel showed no observable pathology (FIGS. 14D, 14E).

One can consider any delayed onset of pathological conditions relating SMA hyperthermia treatment, such as structural compromise of the vessel, ruffled endothelial layers or downstream abdominal ischemia. For this consideration, Applicants exposed the anterior mesenteric artery (AMA, which is the quadruped analogue of SMA) of a live pig to 41° C. for 10 minutes and a necropsy was scheduled for 48 h after treatment. An inspection of the AMA, surrounding tissues, including the proximal vessels and the small intestines found no obvious damage to any of the organs immediately after hyperthermia treatment. The animal was monitored throughout the day and into the evening by veterinary staff. A heat lamp was provided to aid in thermoregulation after surgery. Postoperative antibiotics were administered (5 mg/kg enrofloxacin IV twice, 5 mg/kg ceftiofur IM once, 1 gram cefazolin IV once, 1 L of lactated ringers saline IV twice, 60 mL D5W IV once) in the time between surgery and necropsy. At the 48 h time-point, the animal was euthanized after sedation. The animal was euthanized after 48 h because it showed signs of distress and abdominal discomfort, which on gross pathologic examination was due to an inadvertently retained laparotomy sponge at the initial surgical procedure. There was post-operative peritonitis from the foreign body but there was no observed evidence of ischemic necrosis in the stomach, small intestine, or large intestine. The AMA appeared patent with no observed thrombosis or dilation; all bowel appeared viable without evidence of vascular compromise (FIGS. 14A-14H and 18A-18D). There was an extensive foreign body reaction and localized fibrinopurulent peritonitis with an accumulation of a large amount of ascitic fluid in the peritoneal cavity as a result of the extensive manipulation of the abdominal organs and the dissection and isolation of the AMA, as well as fibrinous adhesions between loops of intestine commensurate with the recent laparotomy and reaction to the foreign body.

Figure 14F:
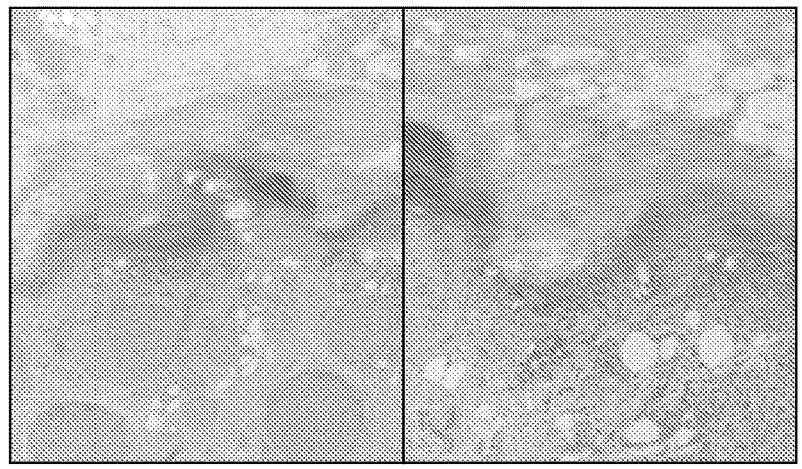
FIGS. 14F-14H) depict various tissues that can be possibly affected by SMA hyperthermia 48 hours after heat treatment.
Figure 14G:
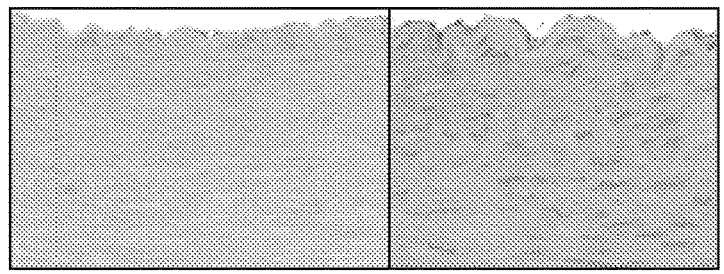
Figure 14H:
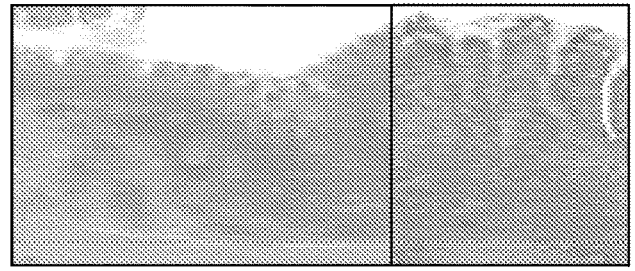
Figures 15A, 15B, 15C:
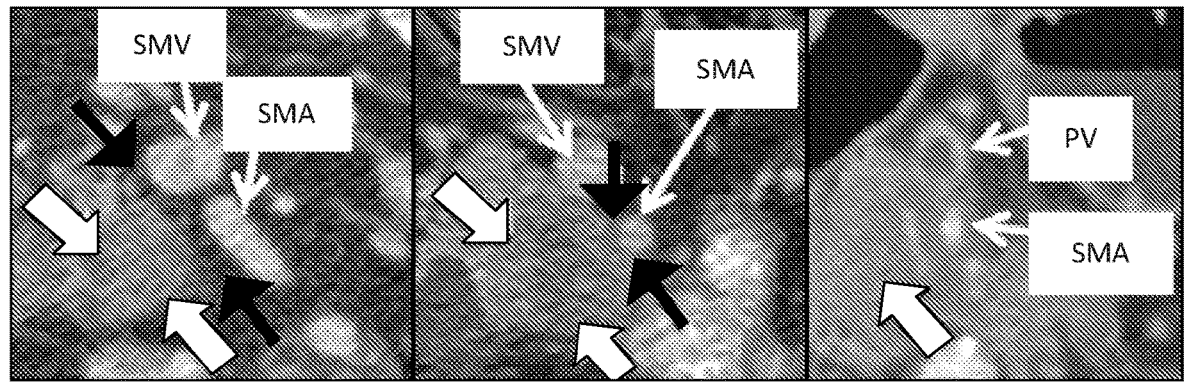
Figure 15D:
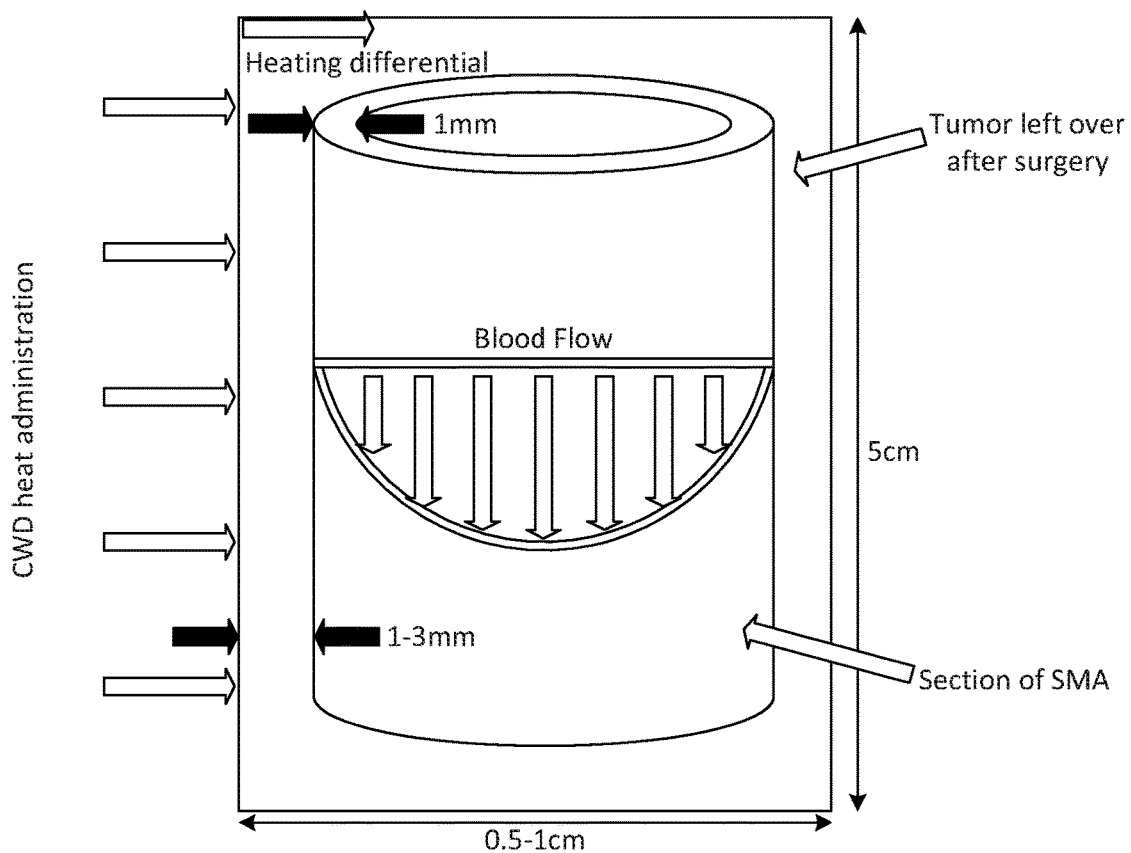
(FIG. 15D) Scanning electron micrograph of the tunica intima of an untreated and (FIG. 14E) 46° C. for 10 mins treated tunica intima of the femoral artery.

Histological analysis revealed acute marked fibrinopurulent inflammation and coagulative necrosis around the isolated treated segment of the artery that is consistent with a surgical procedure that reportedly involved extensive manipulation of the abdominal viscera (FIG. 14A-14H). The isolated segment of the artery consisted of a centrally located artery surrounded by a 4-6 mm thick zone of soft tissue composed of numerous peripheral nerves, mesenteric adipose tissue, and fibrovascular tissue. The coagulonecrotic tissue observed microscopically was located primarily in a layer on the surface of the treated portion of the artery and is likely a result of thermal necrosis associated with the thermal therapy applied to the artery (FIG. 14F). The coagulative necrosis appears to primarily affect the mesenteric adipose tissue resulting in saponification of the adipose tissue. There was coagulative necrosis of a few isolated peripheral nerve bundles near the treated surface of the tissue surrounding the mesenteric artery. Importantly, there was no observed damage to the AMA in the center of the bundle of treated tissue and neither in the intestines (FIGS. 14G and 14H).

Significance of Certain Embodiments

Vascular and in particular arterial invasion, is a key aspect in the resectability of a range of tumors, and therefore often dictates a patient's prognosis and survival. Here, the inventors describe the functionality of an innovative new device to treat tumors with arterial involvement. Embodiments of the device provides an intra-operative tool to deliver localized, mild and controlled hyperthermia to cancer margins that cannot be surgically resected due to them laying close to an unresectable vessel. Applicants used PDAC as a model for the studies as it commonly associates with mesenteric vasculature during its local advancement. In vitro data suggests that mild hyperthermia, in the range of 46° C. for 10 minutes is an optimal thermal dose to induce high levels of cancer cell death when compared to non-malignant cells and eliminate the renewability function of CSCs. In vivo and in silico data supports the well-known phenomena of a blood heat sink that causes high temperature differentials through tissues undergoing hyperthermia. Additionally, the tissues themselves, especially tumor tissue, have high temperature differentials over relatively short distances representing common positive margins that may be due to the tissue characteristics such as the dense stromal reaction found in PDAC.

In particular embodiments, hyperthermia treatment of the positive margin left on vessels such as the SMA during surgery in patients whose tumors are to date considered borderline or unresectable allow a longer period of time between surgery and tumor recurrence, hence increasing patient recovery time before being able to commence chemotherapy regimens and improving the probability of achieving surgical result commensurate with curative intent.

Additionally, in certain embodiments the heat differential provided by blood flow in the vessel will enable a protective effect for the inside lumen whilst the outside cancer layer is heated. This will mean that the outside cancer layer can be exposed to higher thermal doses increasing kill efficacy during hyperthermia treatment, in at least specific cases. The effect of the blood heat sink may be further enhanced with the use of a localized blood cooling aid upstream of the device and/or a splanchnic vasodilator to increase arterial blood flow; however these were not tested herein. Previous device designs encased larger portions of the artery and we noticed that the slimmer design enabled the blood heat sink to be maintained for longer periods. In certain embodiments, this is due to the slim design of the later device meant that blood had a shorter distance to travel under hyperthermia and hence would not have a time to substantially increase in temperature and would therefore conserve the heat sink effect to a greater degree.

The simulations of a simplified model of pancreatic tumor tissue surrounding a blood vessel predicted a large thermal differential through a relatively thin section of tissue. These large thermal differentials were validated by the in vivo and ex vivo experiments. Future simulations will be more sophisticated, including pulsed arterial flow, variable heart rate, and explicit simulation of blood flow. These simulations provide an important tool for the surgeon when deciding the thermal doses warranted for patients of different sizes and weights with varying positive margin thicknesses.

In particular embodiments, one can employ techniques to increase the blood cooling effect by introducing a localized cooling aid such as a cooling pack (33° C. and 36° C., as anything below 30° C. may introduce vasoconstriction) upstream of the tissue undergoing hyperthermia, cooling the encased artery as the device is heating the outside cancer layer and thus hypothetically increase the heat differential between the cancer layer outer surface and the lumen of the vessel. The efficacy of the device may be improved by the incorporation of chemotherapeutic drugs into the inner surface of the device. Drugs can be delivered homogeneously on the tumor section encompassing the artery via the use of micro-needles or sponge delivery system, such as intercalated chemotherapeutics into various polymers such as PLA or biocompatible silk scaffolds. Finally, it is noteworthy that while the work herein used PDAC as a model cancer, one can use the device to treat other cancers where resection is not accessible.

Example 3

Embodiments of Devices for Space-Limited Treatment

FIG. 20 illustrates certain embodiments of a device useful for locations in which space for treatment with devices is limited. As an example, space may be limited because of little of the surrounding tissue has been removed by surgery.

An embodiment of a design for the device to treat cancer margins in tight anatomical spaces is illustrated in FIG. 20. In specific cases the profile of the device is generally rectangular, although other shapes may be utilized. In specific cases, the device is generally in the shape of a stick of gum, wherein the length of the device is much greater than the thickness of the device, on the order of a 1:4 ratio (or 1:3 or 2:5, and so forth) of width to length. In specific embodiments the device is about 18 mm in width and about 80 mm in length, although the dimensions are modifiable. For example, in certain cases a range of size of devices are available to a medical practitioner and are selected based on the size of the tumor(s) in question or the space surrounding the tumor(s) in question. In some cases, analyses (for example, MRI or CT scan) are performed prior to providing access to the tumor(s) to determine a course of action and size of the device to be selected. However, the selection of the particular sized device may occur after the tumor and surrounding space is directly visualized, for example; in specific cases structure of the tumor and/or surrounding the tumor are not apparent until direct visualization. In specific cases, the medical practitioner or a colleague thereof makes necessary modifications to the device at the time of care. In specific embodiments, the length of the device is 1, 2, 3, 4, 5, 6, 7, 8, 9, 10, 12, 13, 14, 15, or more cm. In specific embodiments the width of the device is 0.5, 0.75, 1, 1.2, 1.4. 1.5, 1.6, 1.7, 1.8, 1.9, 2.0, 2.1, 2.2, 2.3, or more cm in width. The thickness of the device may be 0.05 cm, 0.1 cm, 0.15 cm, 0.2 cm, 0.25 cm, 0.3 cm, and so on.

In particular embodiments, a device such as in FIG. 20 is positioned generally perpendicular to the length of a vessel having a tumor surrounding it or nearby. In specific embodiments, the device is held in position after placing near or around the tumor, and it may be held by any particular closing or clamping means. In specific embodiments, the device is guided into placement under the artery prior to clamping around the artery. A guiding mechanism may be a structure that is able to be grasped for guidance or assistance for ease of positioning. In specific embodiments, the guiding mechanism is a wire (for example, flexible) that is suitable enough in length to be able to grasp (for example with surgical tweezers or forces). In particular cases, the wire here acts to enable the surgeon to grasp the device and pull from under the artery. In cases wherein the guiding mechanism is a wire, the wire may be comprised of any surgically suitable metal, such as copper, steel, titanium, etc. The wire may be of a material strong enough to allow an individual to clasp onto the device to pull it under the artery during the positioning of the device in surgery. The end of the guiding mechanism may be shaped, such as a generally pointed end to ease placement of the device around the artery.

At least part of the device may be comprised of a transparent material so as to visualize the device around the vessel. In specific embodiments the device is comprised of a polymer so long as the polymer is flexible. In specific cases, the polymer is silicone or PDMS or an already FDA approved flexible clear polymer, for example. The devices comprises a heating area for heating the tumor and/or its surrounding tissue to a desired temperature. In particular embodiments, the device comprises a first side that emanates heat through a heating area and an opposing second side that does not emanate heat. In specific cases, the heating area does not include the entirety of one side of the device but a portion thereof. In specific cases, the side of the rectangular device from which heat is delivered comprises the heating area and one or more temperature sensors. In specific cases, the one or more temperature sensors are evenly distributed on the heating area. In particular aspects, the sensor senses the heat of the tumor and not the heat of the heating area, although in alternative cases a sensor senses the heat of the heating area; in such cases, the sensor is placed on or near the surface of the heating area-side of the device. The sensor may or may not be present within the material of the device, such as within the polymer itself. The device may be electrically powered.

The particular design illustrated in FIG. 20 incorporates a flexible heater (shaded rectangular area of FIG. 20) and at least one temperature sensor that has been contained in a flexible and transparent polymer. In specific embodiments, the device comprises a copper wire for the practitioner to use during the positioning of the device. i.e., the device needs to be placed around and artery or vessel and therefore the wire enables a contact for the surgeon to grasp when placing it under a vessel. The device is purposely thin to allow for accurate positioning during surgery, although it can be made in various sizes to suit the particular cancer margin being treated. For instance, in some embodiments a practitioner can develop or modify the device after examination of various medical imaging has occurred, such as CT or MRI scans, for example. On the non-heating side of the device, the polymer is made purposefully thicker than the heating side and a thin sheet of aluminum or another insulating material, such as Teflon® or silicone, can prevent the device from giving off heat in any unwanted directions.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

Apte, M. V. et al. Desmoplastic reaction in pancreatic cancer: role of pancreatic stellate cells. Pancreas 29, 179-187 (2004).

Arslan, A., Buanes, T. & Geitung, J. T. Pancreatic carcinoma: MR, MR angiography and dynamic helical CT in the evaluation of vascular invasion. Eur J Radiol 38, 151-159 (2001).

Bachem, M. G. et al. Pancreatic carcinoma cells induce fibrosis by stimulating proliferation and matrix synthesis of stellate cells. Gastroenterology 128, 907-921 (2005).

Bickel, M. The role of interleukin-8 in inflammation and mechanisms of regulation. Journal of periodontology 64, 456-460 (1993).

Bottger, T. C. et al. Diagnosing and staging of pancreatic carcinoma-what is necessary? Oncology 55, 122-129 (1998).

Crank, J., Nicolson, P. & Hartree, D. R. A practical method for numerical evaluation of solutions of partial differential equations of the heat-conduction type. Mathematical Proceedings of the Cambridge Philosophical Society 43, 50, doi:10.1017/S0305004100023197 (1947).

Dave, B. et al. Selective small molecule Stat3 inhibitor reduces breast cancer tumor-initiating cells and improves recurrence free survival in a human-xenograft model. PloS one 7, e30207, doi:10.1371/journal.pone.0030207 (2012).

DeWitt, J. et al. Comparison of endoscopic ultrasonography and multidetector computed tomography for detecting and staging pancreatic cancer. Ann Intern Med 141, 753-763 (2004).

Ene-Obong, A. et al. Activated pancreatic stellate cells sequester CD8+ T cells to reduce their infiltration of the juxtatumoral compartment of pancreatic ductal adenocarcinoma. Gastroenterology 145, 1121-1132, doi: 10.1053/j.gastro.2013.07.025 (2013).

Erkan, M. et al. Preoperative acute pancreatitis in periampullary tumors: implications for surgical management. Digestion 75, 165-171, doi:10.1159/000106799 (2007).

Hasgall, P. et al. IT'IS Database for Thermal and Electromagnetic Parameters of Biological Tissues. http://www.itis.ethz.ch/database, doi:10.13099/VIP21000-03-0. (2015).

Hemming, A. W., Reed, A. I., Langham, M. R., Fujita, S. & Howard, R. J. Combined Resection of the Liver and Inferior Vena Cava for Hepatic Malignancy. Annals of surgery 239, 712-721, doi:10.1097/01.sla.0000124387.87757.eb (2004).

Holdman, X. B. et al. Upregulation of EGFR signaling is correlated with tumor stroma remodeling and tumor recurrence in FGFR1-driven breast cancer. Breast Cancer Res 17, 141, doi:10.1186/s13058-015-0649-1 (2015).

Hwang, R. F. et al. Cancer-Associated Stromal Fibroblasts Promote Pancreatic Tumor Progression. Cancer Res 68, 918-926, doi: 10.1158/0008-5472.CAN-07-5714 (2008).

Jaganathan, H., Mitra, S., Srinivasan, S., Dave, B. & Godin, B. Design and in vitro evaluation of layer by layer siRNA nanovectors targeting breast tumor initiating cells. PloS one 9, e91986, doi:10.1371/journal.pone.0091986 (2014).

Kato, T. et al. Multivisceral Ex Vivo Surgery for Tumors Involving Celiac and Superior Mesenteric Arteries. American Journal of Transplantation 12, 1323-1328, doi: 10.1111/j.1600-6143.2011.03945.x (2012).

Kim, E. K. & Choi, E.-J. Pathological roles of MAPK signaling pathways in human diseases. Biochimica et Biophysica Acta (BBA)—Molecular Basis of Disease 1802, 396-405, doi: http://dx.doi.or/10.1016/j.b-badis.2009.12.009 (2010).

Lore, J. M., Jr. & Boulos, E. J. Resection and reconstruction of the carotid artery in metastatic squamous cell carcinoma. Am J Surg 142, 437-442 (1981).

Lu, D. S. et al. Effect of vessel size on creation of hepatic radiofrequency lesions in pigs: assessment of the "heat sink" effect. AJR Am J Roentgenol 178, 47-51, doi: 10.2214/ajr.178.1.1780047 (2002).

Maiques, M. M. Sim4Life: A Simulation Platform for Life Sciences and Medtech Applications. European Cells and Materials 27 (2014).

Megibow, A. J. et al. Pancreatic adenocarcinoma: CT versus MR imaging in the evaluation of resectability—report of the Radiology Diagnostic Oncology Group. Radiology 195, 327-332, doi:10.1148/radiology.195.2.7724748 (1995).

Miyazaki, M. et al. Combined vascular resection in operative resection for hilar cholangiocarcinoma: does it work or not? Surgery 141, 581-588, doi:10.1016/j.surg.2006.09.016 (2007).

Mokdad, A. A., Singal, A. G., Marrero, J. A., Zhu, H. & Yopp, A. C. Vascular Invasion and Metastasis is Predictive of Outcome in Barcelona Clinic Liver Cancer Stage C Hepatocellular Carcinoma. Journal of the National Comprehensive Cancer Network: JNCCN 15, 197-204 (2017).

Molina, V. et al. Surgical treatment of perihilar cholangiocarcinoma: early results of en bloc portal vein resection. Langenbeck's archives of surgery 402, 95-104, doi: 10.1007/s00423-016-1542-9 (2017).

Normanno, N. et al. Epidermal growth factor receptor (EGFR) signaling in cancer. Gene 366, 2-16, doi:http://dx.doi.org/10.1016/j.gne.2005.10.018 (2006).

Norton, J. A. et al. Morbidity and mortality of aggressive resection in patients with advanced neuroendocrine tumors. Arch Surg 138, 859-866, doi:10.1001/archsurg.138.8.859 (2003).

Oei, A. L. et al. Targeting therapy-resistant cancer stem cells by hyperthermia. International journal of hyperthermia: the official journal of European Society for Hyperthermic Oncology, North American Hyperthermia Group, 1-12, doi:10.1080/02656736.2017.1279757 (2017).

Paula, I. P. S., Isabel, M. M. F., Rui, A. G. B. N. I., Carlos, M. M. N. & Joao, P. M. R. B. Application of Hyperthermia for Cancer Treatment: Recent Patents Review. Recent Patents on Anti-Cancer Drug Discovery 7, 64-73, doi: http://dx.doi.org/10.2174/157489212798358038 (2012).

Pawlik, T. M. et al. Effect of Surgical Margin Status on Survival and Site of Recurrence After Hepatic Resection for Colorectal Metastases. Annals of surgery 241, 715-724, doi:10.1097/01.sla.0000160703.75808.7d (2005).

Pennes, H. Analysis of tissue and arterial blood temperatures in the resting human forearm. Journal of applied physiology 1, 93-122, doi:9714612 (1948).

Rich, B. S. et al. Resectability and operative morbidity after chemotherapy in neuroblastoma patients with encasement of major visceral arteries. Journal of pediatric surgery 46, 103-107, doi:10.1016/j.jpedsurg.2010.09.075 (2011).

Schmalbach, C. E. & Gourin, C. Managing Vascular Tumors-Open Approaches. Otolaryngologic clinics of North America 49, 777-790, doi:10.1016/j.otc.2016.03.001 (2016).

Schwarzbach, M. H. M. et al. Clinical results of surgery for retroperitoneal sarcoma with major blood vessel involvement. Journal of Vascular Surgery 44, 46-55, doi:http://doi.org/10.106/i.jvs.2006.03.001 (2006).

Soriano, A. et al. Preoperative staging and tumor resectability assessment of pancreatic cancer: prospective study comparing endoscopic ultrasonography, helical computed tomography, magnetic resonance imaging, and angiography. Am J Gastroenterol 99, 492-501, doi:10.1111/j.1572-0241.2004.04087.x (2004).

Sumimoto, H., Imabayashi, F., Iwata, T. & Kawakami, Y. The BRAF-MAPK signaling pathway is essential for cancer-immune evasion in human melanoma cells. The Journal of Experimental Medicine 203, 1651-1656, doi: 10.1084/jem.20051848 (2006).

Surget, S., Khoury, M. P. & Bourdon, J. C. Uncovering the role of p53 splice variants in human malignancy: a clinical perspective. OncoTargets and therapy 7, 57-68, doi:10.2147/ott.s53876 (2013).

Tang, D. et al. High expression of Galectin-1 in pancreatic stellate cells plays a role in the development and maintenance of an immunosuppressive microenvironment in pancreatic cancer. Int J Cancer 130, 2337-2348, doi: 10.1002/ijc.26290 (2012).

Tungjitkusolmun, S. et al. Three-Dimensional finite-element analyses for radio-frequency hepatic tumor ablation. IEEE transactions on bio-medical engineering 49, 3-9, doi:10.1109/10.972834 (2002).

Waked, I. et al. Transarterial chemo-embolisation of hepatocellular carcinoma: impact of liver function and vascular invasion. British journal of cancer 116, 448-454, doi:10.1038/bjc.2016.423 (2017).

Wang, T. et al. Senescent Carcinoma-Associated Fibroblasts Upregulate IL8 to Enhance Prometastatic Phenotypes. Molecular cancer research: MCR 15, 3-14, doi:10.1158/1541-7786.mcr-16-0192 (2017).

Ware, M. J. et al. Analysis of the influence of cell heterogeneity on nanoparticle dose response. ACS nano 8, 6693-6700, doi: 10.1021/nn502356f (2014).

Ware, M. J. et al. Radiofrequency treatment alters cancer cell phenotype. Scientific reports 5, 12083, doi:10.1038/srep12083 (2015).

Welte, T. et al. Oncogenic mTOR signalling recruits myeloid-derived suppressor cells to promote tumour initiation. Nat Cell Biol 18, 632-644, doi:10.1038/ncb3355 (2016).

Wilson, J. S., Pirola, R. C. & Apte, M. V. Stars and stripes in pancreatic cancer: role of stellate cells and stroma in cancer progression. Front Physiol 5, 52, doi:10.3389/fphys.2014.00052 (2014).

Xu, Z. et al. Role of pancreatic stellate cells in pancreatic cancer metastasis. The American journal of pathology 177, 2585-2596, doi:10.2353/ajpath.2010.090899 (2010).

Yeo, C. J. et al. Six hundred fifty consecutive pancreaticoduodenectomies in the 1990s: pathology, complications, and outcomes. Ann Surg 226, 248-257; discussion 257-260 (1997).

Ypsilantis, P. et al. Early hemodynamic effects after extended liver radiofrequency ablation. The Journal of surgical research 195, 204-210, doi: 10.1016/j.jss.2014.12.003 (2015).

Zhou, C. et al. AMPK-autophagy inhibition sensitizes icaritin-induced anti-colorectal cancer cell activity. Oncotarget, doi:10.18632/oncotarget.14718 (2017)

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

We claim:

1. A medical device comprising:
   a first semi-cylindrical shell and a second semi-cylindrical shell, together defining an inner lumen adapted and configured to receive an anatomical vessel;
   one or more energy sources;
   a controller programmed to control operation of the one or more energy sources to heat at least a portion of the anatomical vessel or a tumor adjacent thereto to a hyperthermic temperature sufficient to diminish or prevent future tumor growth; and
   one or more diffusers located diametrically inward from the one or more energy sources,
   wherein the one or more energy sources comprise radiofrequency (RF) energy generating units.

2. The medical device of claim 1, wherein the one or more diffusers comprise gelatin.

3. The medical device of claim 1, further comprising:
   one or more temperature sensors located on an inner surface of the one or more diffusers and communicatively coupled to the controller.

4. A medical device comprising:
   a first semi-cylindrical shell and a second semi-cylindrical shell together;
   one or more energy sources mounted on one or more inner surfaces of the first semi-cylindrical shell and on one or more inner surfaces of the second semi-cylindrical shell;
   one or more diffusers located diametrically inward from the one or more energy sources;
   one or more temperature sensors located on an inner surface of the one or more diffusers; and
   a controller communicatively coupled to the one or more temperature sensors, the controller programmed to control operation of the one or more energy sources based on feedback from the one or more temperature sensors to heat at least a portion of the anatomical vessel or a tumor adjacent thereto to a hyperthermic temperature sufficient to diminish or prevent future tumor growth,
   wherein the one or more energy sources comprise radiofrequency (RF) energy generating units.

5. A medical device comprising:
   a first semi-cylindrical shell and a second semi-cylindrical shell, together defining an inner lumen adapted and configured to receive an anatomical vessel;
   one or more energy sources; and
   a controller programmed to control operation of the one or more energy sources to heat at least a portion of the anatomical vessel or a tumor adjacent thereto to a hyperthermic temperature sufficient to diminish or prevent future tumor growth,
   wherein the one or more energy sources comprise radiofrequency (RF) energy generating units and wherein a surface of the device comprises one or more anti-cancer therapies.

6. The device of claim 5, wherein the anti-cancer therapies comprise a chemotherapeutic drug, a hormone therapy, an immunotherapy, or a combination thereof.

7. A method of treating an anatomical vessel, the method comprising:
   positioning a medical device around the anatomical vessel and/or any unresected tumor adjacent thereto; and
   actuating the medical device to heat at least a portion of an anatomical vessel or any unresected tumor adjacent thereto to a hyperthermic temperature sufficient to diminish or prevent future tumor growth,
   wherein the medical device comprises:
   a first semi-cylindrical shell and a second semi-cylindrical shell, together defining an inner lumen adapted and configured to receive an anatomical vessel;
   one or more energy sources; and
   a controller programmed to control operation of the one or more energy sources to heat at least a portion of the anatomical vessel or a tumor adjacent thereto to a hyperthermic temperature sufficient to diminish or prevent future tumor growth,
   wherein the one or more energy sources comprise radiofrequency (RF) energy generating units.

8. The method of claim 7, wherein the anatomical vessel is a blood vessel.

9. The method of claim 8, wherein the blood vessel is selected from the group consisting of celiac axis, superior mesenteric artery, and hepatic artery.

10. The method of claim 7, wherein the tumor is a pancreatic ductal adenocarcinoma (PDAC).

11. The method of claim 7, wherein at least a portion of the vessel is heated for a range of time from 0.5-30 minutes.

12. The method of claim 7, wherein the hyperthermic temperature is between 37-46° C.

13. The method of claim 7, wherein one or more cooling agents are provided to the vessel upstream of the device.

14. The method of claim 13, wherein the cooling agents comprise a cooling pack.

* * * * *